United States Patent
Ota et al.

(10) Patent No.: US 9,545,218 B2
(45) Date of Patent: Jan. 17, 2017

(54) RF COIL DEVICE AND MAGNETIC RESONANCE IMAGING APPARATUS

(75) Inventors: Miyuki Ota, Otawara (JP); Sadanori Tomiha, Nasushiobara (JP); Shinji Mitsui, Nasushiobara (JP); Mitsuo Takagi, Otawara (JP); Hiroki Motohashi, Otawara (JP); Kazuya Okamoto, Saitama (JP); Junichi Makita, Edogawa (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1366 days.

(21) Appl. No.: 13/403,315

(22) Filed: Feb. 23, 2012

(65) Prior Publication Data
US 2012/0153954 A1  Jun. 21, 2012

Related U.S. Application Data

(63) Continuation of application No. PCT/JP2011/075734, filed on Nov. 8, 2011.

(30) Foreign Application Priority Data

Nov. 17, 2010  (JP) .................................. 2010-256617

(51) Int. Cl.
*G01R 33/44* (2006.01)
*A61B 5/055* (2006.01)
*G01R 33/34* (2006.01)

(52) U.S. Cl.
CPC ....... *A61B 5/0555* (2013.01); *G01R 33/34084* (2013.01)

(58) Field of Classification Search
CPC ..... G01R 33/3415; G01R 33/30; G01R 33/32; G01R 33/34; G01R 33/34007; G01R 33/34084; G01R 33/341; G01R 33/36; A61B 5/0555
(Continued)

(56) References Cited

U.S. PATENT DOCUMENTS

| 5,143,068 A | 9/1992 | Muennemann |
| 5,343,862 A | 9/1994 | Jones |

(Continued)

FOREIGN PATENT DOCUMENTS

| JP | 06-90923 | 4/1994 |
| JP | 9-192115 | 7/1997 |

(Continued)

OTHER PUBLICATIONS

International Search Report for PCT/JP2011/075734 mailed Jan. 10, 2012.
(Continued)

*Primary Examiner* — Melissa Koval
*Assistant Examiner* — Rishi Patel
(74) *Attorney, Agent, or Firm* — Nixon & Vanderhye P.C.

(57) ABSTRACT

In one embodiment, an RF coil device includes a base board, a belt member, a first coil element, a second coil element inside the base board, and a connecting unit. Both ends of the belt member are respectively connected to mutually separated places on the base board, so that the center part of the belt member is located on the anterior surface of the base board. The belt member is curved to form airspace between the center part thereof and the anterior surface for letting an arm pass through in interdigitation state. The first coil element includes first and second partial coils inside the belt member, and becomes a loop coil element by their connection. The connecting unit detachably connects the base board (Continued)

to the belt member, and mutually connects the first and second partial coils in the interdigitation state.

20 Claims, 38 Drawing Sheets

(58) Field of Classification Search
USPC ......... 324/318, 321, 322; 600/415, 421, 422
See application file for complete search history.

(56) References Cited

U.S. PATENT DOCUMENTS

| | | | | |
|---|---|---|---|---|
| 5,351,688 | A * | 10/1994 | Jones | ............... G01R 33/34046 |
| | | | | 324/318 |
| 5,477,146 | A | 12/1995 | Jones | |
| 7,031,763 | B1 | 4/2006 | Zhang | |
| 2004/0030241 | A1 * | 2/2004 | Green | ................. A61B 5/0555 |
| | | | | 600/422 |
| 2006/0208734 | A1 | 9/2006 | Xue | |
| 2009/0121715 | A1 | 5/2009 | Guan | |

FOREIGN PATENT DOCUMENTS

| | | |
|---|---|---|
| JP | 2001-95776 | 4/2001 |
| JP | 2007-229004 | 9/2007 |
| WO | WO 2006/114923 | 11/2006 |
| WO | WO 2007/048032 | 4/2007 |

OTHER PUBLICATIONS

Yang, X et al., "An Optimized "Od-like" 6-Channel Flexible and Ergonomic Shoulder Array Coil at 1.5T", Proceedings of ISMRM-ESMRMB, Joint Annual Meeting, 2010, .5, # 3843, 1 page.

Hamamura, Y et al., "An 8 Channel Shoulder Coil for High Resolution Imaging", Proc. Intl. Soc. Mag. Reson, 14, May 2006,, # 419, 1 page.

English Translation of International Preliminary Report on Patentability issued Jun. 12, 2013 for Application No. PCT/JP2011/075734.

* cited by examiner

RF COIL DEVICE AND MAGNETIC RESONANCE IMAGING APPARATUS

This application is a continuation of International Application No. PCT/JP2011/075734, filed 8 Nov. 2011, and claims the benefit of priority from Japanese Patent Application No. 2010-256617, filed on Nov. 17, 2010;

The entire contents of which are incorporated herein by reference.

BACKGROUND OF THE INVENTION

1. Field of the Invention

Embodiments described herein relate generally to an RF (radio frequency) coil device and a magnetic resonance imaging apparatus.

2. Description of the Related Art

MRI is an imaging method which magnetically excites nuclear spins of an object set in a static magnetic field with an RF signal having the Larmor frequency and reconstructs an image based on MR signals generated due to the excitation. The aforementioned MRI means magnetic resonance imaging, the RF signal means a radio frequency signal, and the MR signal means a nuclear magnetic resonance signal.

Here, the device, that fulfills the role of transmitting an RF signal to a nuclear spin by supplying RF pulse current to a coil and the like and receiving a generated echo signal as an MR signal, is an RF coil device (for example, refer to the after-mentioned Patent Document 1 and Patent Document 2). The RF coil devices are classified into a whole body type and a local type. Various types of the RF coil devices for a local area are used according to an imaging part. For example, in the case of imaging of a shoulder joint, a dedicated RF coil device for a shoulder joint is set to the shoulder of an object.

[Patent Document 1] Japanese Patent Application Laid-open (KOKAI) Publication No. 2007-229004

[Patent Document 2] Japanese Patent Application Laid-open (KOKAI) Publication No. 2001-95776

Conventional RF coil devices for a shoulder joint are dented like a bowl so that they cover over and fit on the shoulder under the pose in which the arm of an object is down. However, for example, in the case of imaging of a shoulder joint after administration of contrast medium, imaging under the pose in which the arm of an object is raised is sometimes desired. In this case, there is airspace between the conventional RF coil device and the shoulder due to the dent, the shoulder is separated from the RF coil device by the space corresponding to the airspace, and signal intensity of received nuclear magnetic signals becomes weak.

On the other hand, if different RF coil devices are respectively set for imaging under the pose in which the arm is raised and imaging under the pose in which the arm is down, this results in an increase in cost.

Thus, a configuration, in which one RF coil device can meet both of imaging under the pose in which the arm is raised and imaging under the pose in which the arm is down, is preferable.

Therefore, as an RF coil device for a shoulder joint in MRI, technology to enable the RF coil device to be effortlessly set on the shoulder under both poses with the arm raised and down, as well as keep sufficient coil sensitivity has been desired.

DETAILED DESCRIPTION

Figure 1:
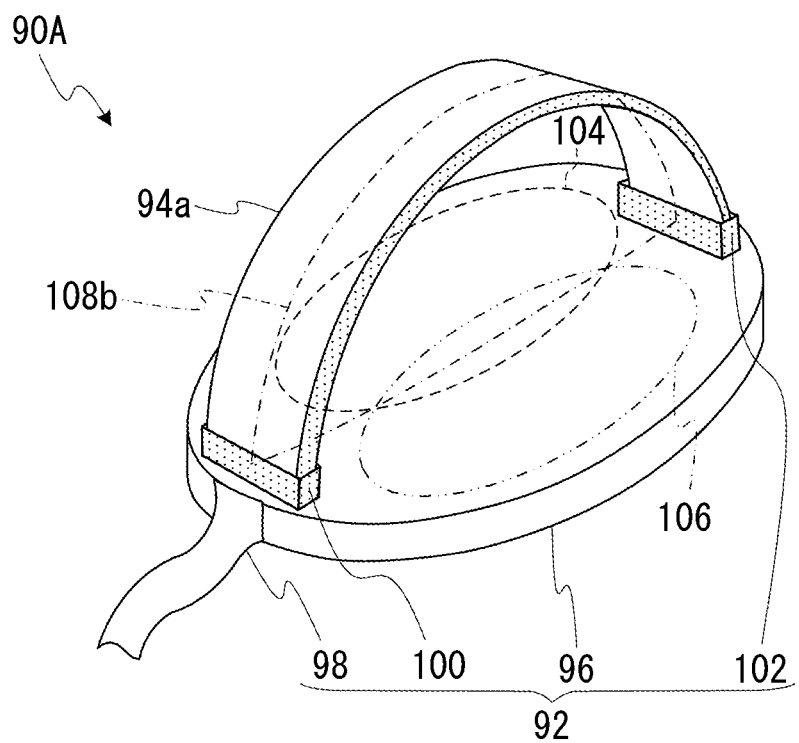
FIG. 1 is a schematic oblique perspective figure showing an outline structure of the RF coil device of the first embodiment.

In each of the following embodiments of RF coil devices as examples, each RF coil device is set on the shoulder(s) of an object and receives an echo signal in magnetic resonance imaging. Examples of aspects, which embodiments of the present invention may take, will be described below per aspect.

(1) An RF coil device in one embodiment includes a base board, a belt member, a first coil element, a second coil element and a plurality of connecting units.

The base board has a thickness between its anterior surface and its underside surface opposite to the anterior surface, and is to come into contact with the object at the anterior surface.

The belt member has a band-like shape. The belt member is connected at its one end and opposite end to the base board at different positions spaced apart from each other with a central part of the belt member being located on the side of the anterior surface of the base board. The belt member is bent so as to form a space for disposing an arm of the object between the central part and the anterior surface when the base board and the belt member are connected to each other.

The first coil element includes a first partial coil disposed in the belt member and a second partial coil disposed in the base board. The first coil element forms a loop coil, when the first and second partial coils are electrically connected to each other.

The second coil element is disposed in the base board.

The plurality of connecting units are disposed on the anterior surface of the base board at one end and the opposite end of the second partial coil. The plurality of connecting units detachably connects the base board and the belt member to each other, and electrically connects the first and second partial coils to each other when the base board and the belt member are connected to each other.

(2) An RF coil device of another embodiment includes a base board, a belt member, a overlay member, a first coil element, a second coil element, and a third coil element.

The base board has a thickness between its anterior surface and its underside surface opposite to the anterior surface, and is to come into contact with the object at the anterior surface.

The belt member has a band-like shape. The belt member is connected at its one end and the opposite end to the base board at different positions spaced apart from each other with a central part of the belt member being located on the side of the anterior surface of the base board. The belt member is bent so as to form a space for disposing an arm of the object between the central part and the anterior surface when the base board and the belt member are connected to each other.

The first coil element has a part disposed in the belt member to extend from one end to the opposite end and the remaining part disposed in the base board so as to form a loop coil.

The second coil element is disposed in the base board.

The overlay member is detachably connected to the base board to partially cover the anterior surface of the base board.

At least a part of the third coil element is disposed in the overlay member.

(3) An RF coil device of another embodiment includes a base board, a belt member, a connecting unit, a first coil element, and a second coil element.

The base board has a thickness between its anterior surface and its underside surface opposite to the anterior surface, and is to come into contact with the object at the anterior surface.

The belt member has a band-like shape, and is pivotally fixed to the base board at one end. The belt member is detachably connected to the base board at the opposite end with a central part of the belt member being located on the side of the anterior surface of the base board, when the belt member is connected to the base board. The belt member is bent so as to form a space for disposing an arm of the object between the central part and the anterior surface, when the base board and the belt member are connected to each other.

The first coil element has a part disposed in the belt member to extend from one end to the opposite end and the remaining part disposed in the base board. The first coil element forms a loop coil, when the base board and the belt member are connected to each other.

The connecting unit is disposed on the base board at one end of the first coil element, and detachably connects the opposite end of the belt member to the base board. The connecting unit electrically connects the part and the remaining part of the first coil element to each other, when the belt member and the base board are connected to each other.

The second coil element is disposed in the base board.

(4) An RF coil device of another embodiment includes a base member containing an internally disposed first coil element, a belt member, a flap member, a second coil element, and a third coil element.

The base member is to come into contact with the shoulder of the object.

The belt member is made of a flexible material in the form of a band, is partially fixed to the base member, and wraps around an arm of the object when one end and the opposite end thereof are connected to each other.

The second coil element is disposed in the belt member to extend from one end to the opposite end, and forms a loop coil when both ends of the belt member are connected to each other.

The connecting unit is disposed at one end or the opposite end of the belt member, detachably connects both ends of the belt member to each other, and electrically connects both ends of the second coil element to each other when both ends of the belt member are connected to each other.

The flap member is made of a flexible material and is partially fixed to the belt member.

The third coil element is a loop coil element. At least a part of the third coil element is disposed in the flap member.

(5) An RF coil device of another embodiment includes a base board, a first belt member, a second belt member, a first coil element, a second coil element, and a third coil element.

The base board has a thickness between its anterior surface and its underside surface opposite to the anterior surface, and is to come into contact with the back of the object including the shoulders at the anterior surface.

Each of the first and second belt members has a band-like shape, and is connected at both ends to the base board at different positions with a central part thereof being located on the side of the anterior surface of the base board. Each of the first and second belt members is bent so as to form a space for disposing a different arm of the object between the central part and the anterior surface, when the first and second belt members are connected to the base board.

The first coil element has a part disposed in the first belt member to extend from one end to the opposite end and the remaining part disposed in the base board, so as to form a loop coil.

The second coil element has a part disposed in the second belt member to extend from one end to the opposite end and the remaining part disposed in the base board, so as to form a loop coil.

The third coil element is disposed in the in the base board.

(6) An RF coil device of another embodiment includes first and second base members configured in the form of flat plates, a belt member, a rotational axis structure, a first coil element, a second coil element, and a third coil element.

The second base member is disposed so that at least a part of the second base member overlaps on the first base member.

The belt member is circularly shaped so as to let an arm of the object pass through the belt member, and a part of the outer periphery of the belt member is fixed to the first base member.

The rotational axis structure includes a rotational axis passing through the first and second base members, and rotatably (pivotally) fixes the first and second base members to the belt member.

The first coil element is disposed in the first base member, the second coil element is disposed in the second base member, and the third coil element is disposed in the belt member.

(7) An RF coil device of another embodiment includes a band member, a connecting unit, a first coil element, a second coil element, and a third coil element.

The band member is made of a flexible material in the form of a band so as to wrap around an arm of the object. The width of the central part of the band member is narrower (smaller) than the ambilateral parts of the central part. The band member is tapered at one end and the opposite end.

The first coil element is disposed in the band member to extend from one end to the opposite end, and forms a loop coil when one end and the opposite end of the first coil element are connected to each other.

The connecting unit is disposed at one end or the opposite end of the band member, and detachably connects both ends of the band member to each other. The connecting unit electrically connects both ends of the first coil element to each other, when both ends of the band member are connected to each other.

The second coil element is disposed in the band member at a position closer to the one end than the central part.

The third coil element is disposed in the band member at a position closer to the opposite end than the central part.

(8) An RF coil device of another embodiment includes a cover member, a belt member, a connecting unit, a first coil element, a second coil element, and a third coil element.

The cover member is made of a flexible material in the form of a band, so as to cover an anterior surface and a posterior surface of the shoulder of the object with the parts at one end and the opposite end thereof by being bent at its middle part in the length direction thereof. The width of the central part of the cover member is narrower than the remaining parts thereof.

The belt member is made of a flexible material, connected at its one end with the one end of the cover member. The belt member is detachably connected at its opposite end with the opposite end of the cover member.

The first coil element has a part disposed in the belt member to extend from the one end to the opposite end and the remaining part disposed in the cover member to extend from the one end to the opposite end. The first coil element forms a loop coil when the opposite end of the cover member and the opposite end of the belt member are connected to each other.

The connecting unit is disposed at the opposite end of the cover member, detachably connects the opposite end of the cover member and the opposite end of the belt member to each other. The connecting unit electrically connects both ends of the first coil element to each other, when the cover member and the belt member are connected to each other.

The second coil element is disposed in the cover member at a position closer to the one end than the central part.

The third coil element is disposed in the cover member at a position closer to the opposite end than the central part.

(9) An RF coil device of another embodiment includes a cover member, a supporting member, a first flap member, a second flap member, a first coil element, a second coil element, and a third coil element.

The cover member has an anterior surface and an underside surface opposite to each other. The cover member is bent with the underside surface positioned inside to have a U-shaped or angled-bracket-shaped transverse section in a plane perpendicular to the anterior surface and the underside surface so as to cover the shoulder of the object.

The supporting member has an aperture (opening) for letting an arm of the object pass. The supporting member is partially fixed to the underside surface of the cover member in such a manner that its aperture plane is oriented in parallel with the transverse section of the cover member.

Each of the first and second flap members is made of a flexible material in the form of a flap. The first and second flap members are partially fixed to the cover member at positions to face each other with the supporting member interposed therebetween, so as to cover a part of an anterior surface or a posterior surface of the shoulder of the object.

The first coil element is disposed in the first flap member.

The second coil element is disposed in the second flap member.

The third coil element is disposed in the supporting member so as to make a circuit on an outer side of the opening.

(10) In one embodiment, an MRI apparatus includes a signal acquisition unit and an image generation unit.

The signal acquisition unit applies a gradient magnetic field to an imaging region, transmits an RF signal for causing nuclear magnetic resonance to the imaging region, and receives an echo signal generated due to nuclear magnetic resonance as a nuclear magnetic resonance signal. The signal acquisition unit includes one of the RF coil devices of the above (1) to (9) which receives the echo signal.

The image generation unit reconstructs image data of the object based on the nuclear magnetic resonance signal.

Embodiments of the present invention will be described with reference to the accompanying drawings. The first to tenth embodiment relate to RF coil devices, and the eleventh embodiment relates to an MRI apparatus using these RF coil devices. Note that the same reference numbers are given for identical components in each figure, and overlapping explanation is abbreviated.

The First Embodiment

FIG. 1 is a schematic oblique perspective figure showing an overview of the RF coil device 90A of the first embodiment. As shown in FIG. 1, the RF coil device 90A is constituted by connecting (coupling) the belt member 94a to the base member 92.

As an example of its mounting method, the base member 92 is arranged on the back side of the shoulder of an object, and the base member 92 and the belt member 94a are arranged so as to pinch the root of one arm (axilla) of the object. The RF coil device 90A includes other belt members 94b, 94c, 94d and 94d' aside from the belt member 94a (see after-mentioned FIG. 6 to FIG. 9), and can change its coil sensitivity area and the number of coil elements by setting the appropriate one out of the belt members 94a, 94b, 94c, 94d and 94d'.

Note that the RF coil device 90A is composed as coils for receiving echo signals (nuclear magnetic resonance signals). In this point, the same applies to the RF coil devices 90B to 90N and 90x in the after-mentioned other embodiments. Additionally, an RF coil is mainly composed of a conductive wire part as a signal line and a conductive wire part as an antenna. In the following explanation, it is assumed that a "coil element" means the aforementioned conductive wire part as an antenna.

Figure 2:
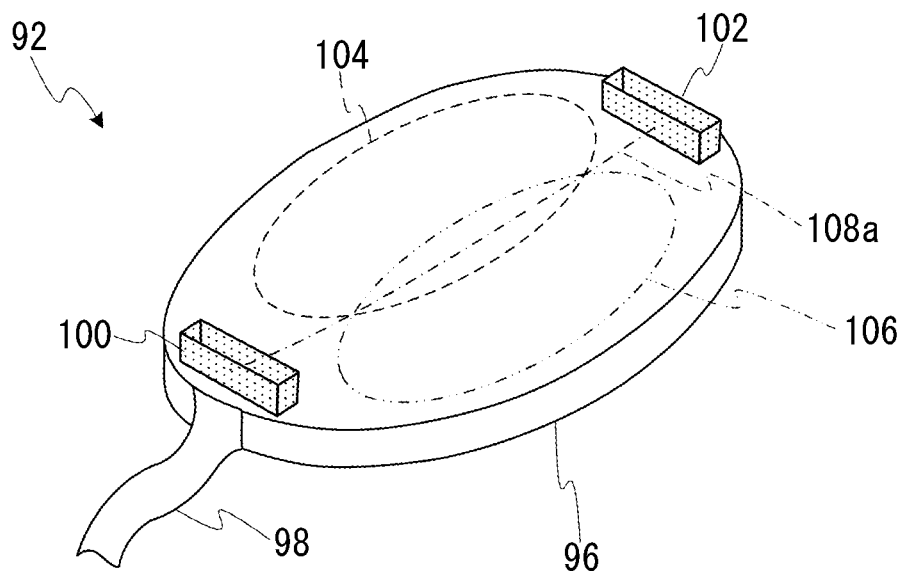
FIG. 2 is a schematic oblique perspective figure showing the structure of the base member in FIG. 1.

FIG. 2 is a schematic oblique perspective figure showing the structure of the base member 92 in FIG. 1. The base member 92 includes a disk-shaped base board 96, a cable 98 and connectors 100 and 102. The connectors 100 and 102 are respectively disposed on the side of one end of the base board 96 and the side of the opposite end of the base board 96. Inside the base board 96, a loop coil element 104 indicated as a dashed line in FIG. 2, a loop coil element 106 indicated as a two-dot chain line and a partial coil 108a indicated as a chain line are disposed (emplaced).

The cable 98 is exposed from the side surface (the surface along the thickness direction of the base board 96) near the connector 100 of the base board 96 which is flat-plate structure. By arranging the cable 98 to this position, the underside surface of the base board 96 is flatly formed. Thereby, under the state in which an object is placed supine on a bed of an MRI apparatus, the base member 92 can be smoothly placed between the bed and the back side of the object. Additionally, the cable 98 is electrically connected to an RF receiver in the MRI apparatus.

The partial coil 108a functions as a loop coil element by being electrically connected to the partial coil 108b inside the after-mentioned belt member 94a. The partial coil 108a is arranged (emplaced) along the center line which evenly bisects the disk-shaped base board 96. The one end of the partial coil 108a is connected to the connector 100, and the opposite end of the partial coil 108a is connected to the connector 102.

The coil elements 104 and 106 are disposed planarly and elliptically, so that extending ranges of their conductive wires are in parallel with the underside surface and the anterior surface of the base board 96.

For example, more than or equal to two thirds of the length of the coil element 104 is disposed on the one side of the base board 96 evenly bisected along the extending line of the partial coil 108a as a criteria. For example, more than or equal to two thirds of the length of the coil element 106 is disposed on the opposite side of the base board 96 bisected similarly.

For the sake of obtaining a decoupling effect, the coil elements 104 and 106 are disposed in such a manner that the minimum plane including the coil element 104 and the minimum plane including the coil element 106 are in parallel with each other and partially facing each other. Note that the coil elements 104, 106, and the partial coil 108a are electrically connected to discrete hard-wirings inside the cable 98, respectively, by heretofore known circuit configuration including an amplifier circuit and the like (not shown in figure) inside the base board 96.

Figure 3:
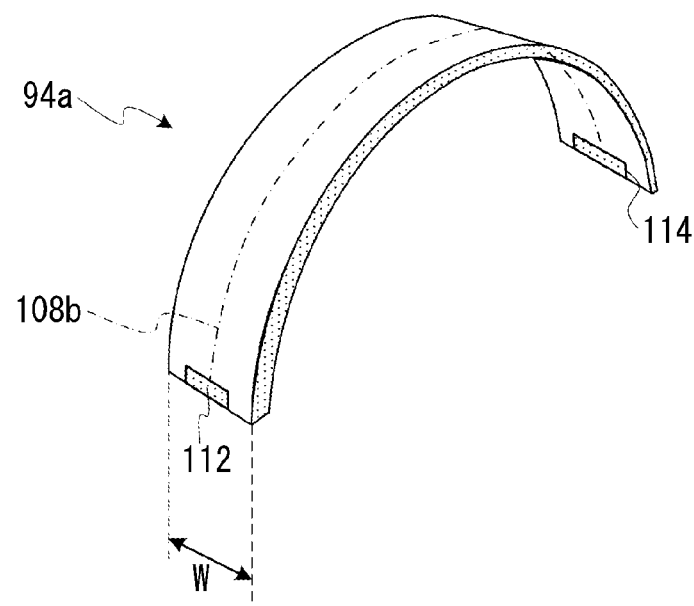
FIG. 3 is a schematic oblique perspective figure showing the structure of the belt member in FIG. 1.

FIG. 3 is a schematic oblique perspective figure showing the structure of the belt member 94a in FIG. 1. As shown in FIG. 3, the shape of the belt member 94a is obtained by semicircularly curving an elongated (band-shaped) board with a predetermined width W. The belt member 94a includes the connectors 112 and 114 respectively disposed on its both ends, and the partial coil 108b. The partial coil 108b is semicircularly arranged inside the belt member 94a along the extending direction of the belt member 94a, extending from its one end to the opposite end.

The connector 100 in FIG. 2 is shaped so that the side of the one end of the belt member 94a including the connector 112 is interdigitated in the connector 100. The connector 102 in FIG. 2 is shaped so that the side of the opposite end of the belt member 94a including the connector 114 is interdigitated in the connector 102 (see FIG. 1). Under the interdigitation state in which both ends of the belt member 94a are interdigitated in the base member 92, one end of the partial coil 108a and one end of the partial coil 108b are electrically connected with each other by an electrode and the like (not shown) inside the connectors 100 and 112. Additionally, in this interdigitation state, the opposite end of the partial coil 108a and the opposite end of the partial coil 108b are electrically connected with each other by an electrode and the like (not shown) inside the connectors 102 and 114.

As to the configuration which provides the connectors 100, 102, 112, and 114 with the aforementioned function, it may be similar to the conventional art (refer to Patent Document 2, for example), and detailed explanation is abbreviated. Additionally, under the aforementioned interdigitation state in which the belt member 94a is interdigitated in the connectors 100 and 102, the partial coil 108a and 108b functions as one coil element.

The partial coils 108a and 108b are disposed in such a manner that the plane overlapping on the extending regions of the conductive wires of the partial coils 108a and 108b is orthogonal to both the underside surface and the anterior surface of the base board 96 under the above interdigitation state.

In order to achieve this, each part is configured as a stereoscopic shape, so that the extending regions of the partial coils 108a and 108b are planar and a semicircular transverse section of the belt member 94a is orthogonal to the underside surface and the anterior surface of the base board 96 under the above interdigitation state.

Thus, the plane overlapping on the entire loop of the coil element composed of the partial coils 108a and 108b and the plane overlapping on the entire loop of the coil element 106 are orthogonalized to each other, and their mutual coupling scarcely occurs. Similarly, the plane overlapping on the entire loop of the coil element composed of the partial coils 108a and 108b and the plane overlapping on the entire loop of the coil element 104 are orthogonalized to each other, and their mutual coupling scarcely occurs.

Next, the substance used for each part of the RF coil device 90A will be explained below. The RF coil device 90A in FIG. 1 is made of an insulating material except the cable 98, the coil element 104, 106, the partial coils 108a and 108b, an internal circuit (not shown) which connects these coils to the cable 98, and electrode parts (not shown) inside the connectors 100, 102, 112, and 114.

The base board 96 is made of an undeformable material. Note that, by covering its undeformable main body with, for example, a soft fiber material, the base board 96 may include cushioning characteristics when it is mounted. As examples of the aforementioned undeformable material, FRP (Fiber Reinforced Plastics), polyethylene and the like can be used.

The partial coil 108a and the coil elements 104 and 106 inside the base board 96 are constituted by arranging a conductive material such as copper on a solid circuit board made of the above FRP or the like.

The belt member 94a is made of an undeformable material. By covering its anterior surface with a soft material, the belt member 94a may include cushioning characteristics when the RF coil device 90A is mounted (this point applies to belt members, base members and the like which are made of an undeformable material in each of the after-mentioned embodiments). The partial coil 108b is similarly constituted by arranging a conductive material such as copper on a solid circuit board made of the above FRP or the like. The same applies to the coil elements 118, 120, 122, 124 and 134, and the like in FIG. 6 to FIG. 9.

Figure 4:
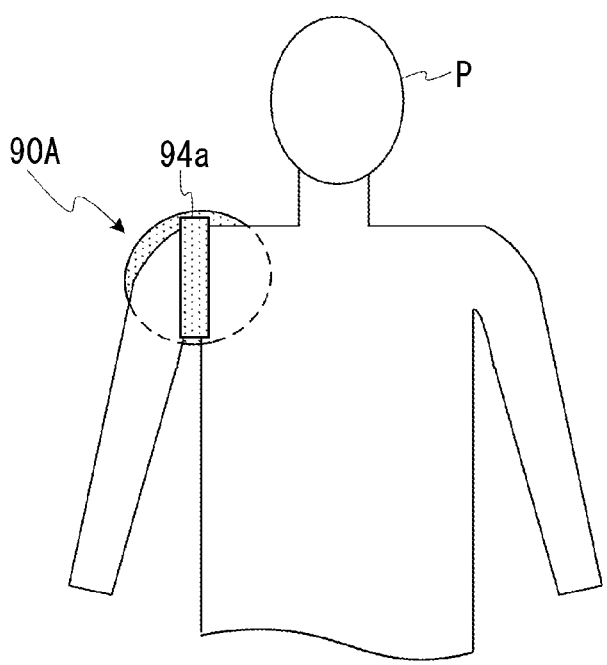
FIG. 4 is a schematic planimetric diagram showing an example of the mounting state of the RF coil device in FIG. 1 under the pose in which the arm of an object is put down.

FIG. 4 is a schematic planimetric diagram showing an example of the mounting state of the RF coil device 90A, under the pose in which the arm of an object P is put down. For the sake of simplicity, details of the connectors 100, 102 and the like are abbreviated in FIG. 4 (the same applies to other figures showing mounting state in each of the after-mentioned embodiments). As shown in FIG. 4, in the mounting state of the RF coil device 90A, the arm of the object P passes through the space between the belt member 94a and the base member 92.

As a method of setting (mounting), for example, in the state in which the base member 92 is arranged near the back side of the shoulder of the object P, the belt member 94a may be interdigitated in the base member 92 in such a manner that the belt member 94a covers over the root of the arm from above. Alternatively, under the state in which the belt member 94a is interdigitated in the base member 92, it may be set by letting the arm of the object P pass through the through-hole which is the airspace between the belt member 94a and the base member 92.

Here, as to the width W of the belt member 94a, it is preferable to be able to effortlessly pinch the belt member 94a in the underarm under the state in which the arm of the object P is put down. For example, the width W of the belt member 94a may be 2 centimeters to 6 centimeters (this point applies to the belt member 286a in the after-mentioned fifth embodiment, the belt member 404 in the seventh embodiment and the like).

Figure 5:
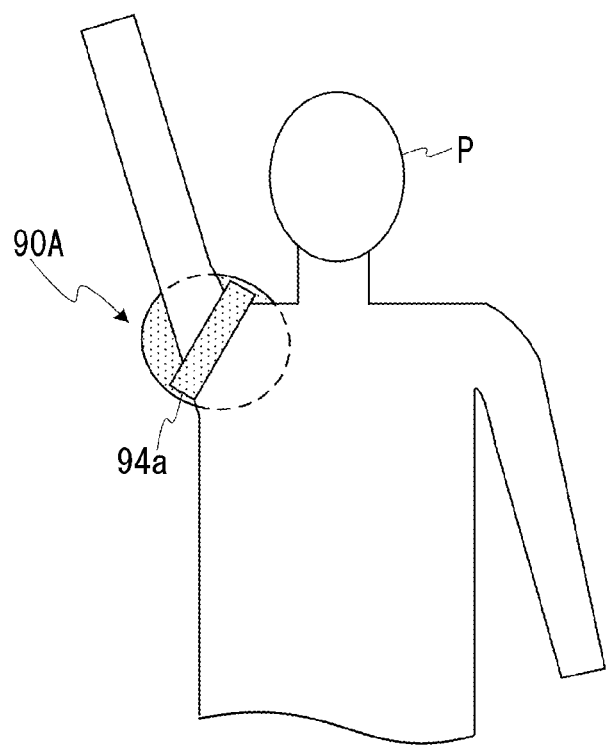
FIG. 5 is a schematic planimetric diagram showing an example of the mounting state of the RF coil device in FIG. 1 under the pose in which the arm of an object is raised.

FIG. 5 is a schematic planimetric diagram showing an example of the mounting state of the RF coil device 90A, under the pose in which the arm of an object P is raised. The arm of the object P is pinched by the belt member 94a whose width W is appropriately set as above stated, and other obstacle to arm's motion does not exist. Thus, the RF coil device 90A can be effortlessly set under both states with the arm raised and lowered.

Figure 6:
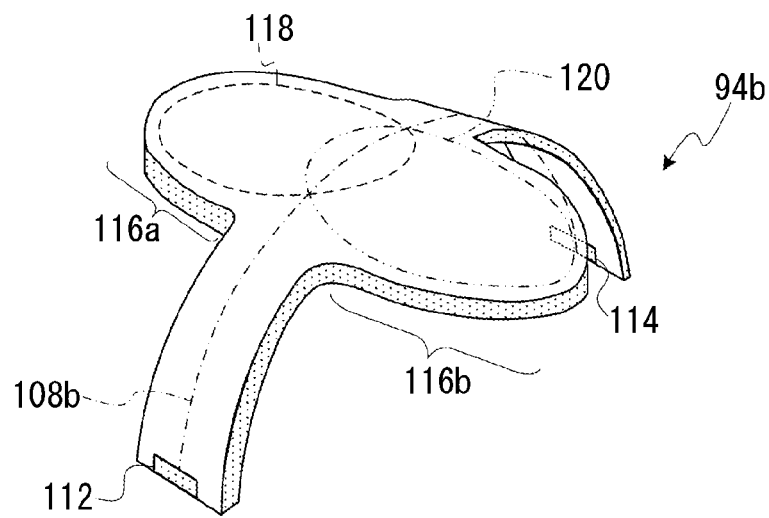
FIG. 6 is a schematic oblique perspective figure showing the structure of the second example of the belt member.

FIG. 6 is a schematic oblique perspective figure showing the structure of another example of the belt member. As shown in FIG. 6, the belt member 94b is obtained by integrally forming projecting parts 116a and 116b on both sides of the center of the belt member 94a in FIG. 3, respectively. The shape of the projecting parts 116a and 116b is an evenly bisected disk. Inside the projecting parts 116a and 116b, loop coil elements 118 and 120 are disposed respectively.

For the sake of obtaining a decoupling effect, the coil elements 118 and 120 are disposed in such a manner that the minimum plane including the coil element 118 and the minimum plane including the coil element 120 are partially facing each other, as before. By interdigitating this belt member 94b in the base member 92, the RF coil device 90A obtains a wide sensitivity region from the five coil elements.

Note that, the coil elements 118 and 120 are respectively connected to discrete hard-wirings inside the cable 98 via hard-wiring inside the belt member 94b, the connectors 100 and 112, and the aforementioned internal circuit inside the base member 92 (not shown). The same applies to the following coil elements 122, 124, and 134 in FIG. 7 to FIG. 9.

Figure 7:
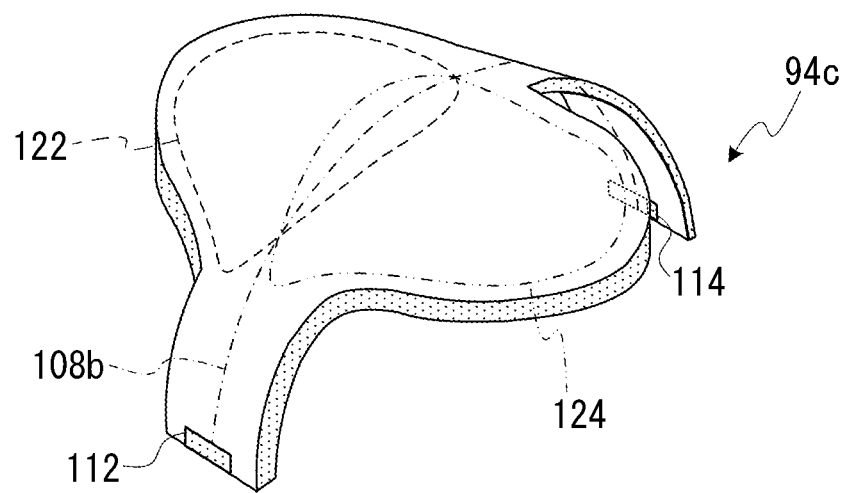
FIG. 7 is a schematic oblique perspective figure showing the structure of the third example of the belt member.

FIG. 7 is a schematic oblique perspective figure showing the structure of another example of the belt member. As shown in FIG. 7, the shape of the belt member 94c is obtained by further enlarging the projecting parts 116a and 116b of the belt member 94b in FIG. 6. Inside the ambilateral projecting parts, loop coil elements 122 and 124 are respectively disposed. Thereby, when the belt member 94c and the base member 92 are mounted on the object P in the way similar to FIG. 4, the sensitivity region becomes wider in the side of the anterior surface of the shoulder of the object P (opposite side of the back).

Figure 8:
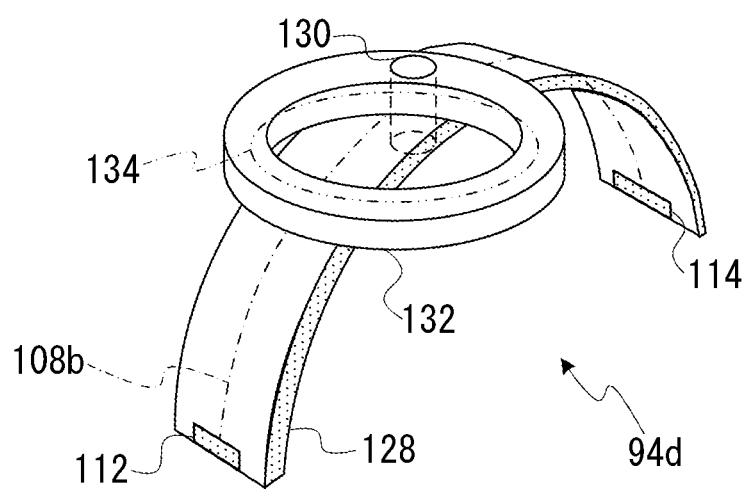
FIG. 8 is a schematic oblique perspective figure showing the structure of the fourth example of the belt member.

FIG. 8 is a schematic oblique perspective figure showing the structure of another example of the belt member. As shown in FIG. 8, in the structure of the belt member 94d, the ring member 132 is rotatably (pivotally) fixed to the semi-circular part 128, whose structure is similar to the belt member 94a in FIG. 3, by the rotational axis structure 130. Note that the ring member 132 is fixed in such a manner that it is rotatable in an identical (unaltered) plane. The rotational axis structure 130 and the ring member 132 are made of an undeformable material, as before. The ring member 132 is circular, and a loop coil element 134 is arranged inside the ring member 132 in such a manner that the coil element 134 extends over the entire loop of the inside of the ring member 132. Note that, in FIG. 8, the belt member 94d has a structure of including the rotational axis so that the rotational axis passes through the semicircular part 128 and the ring member 132. However, as to the structure of making the ring member 132 rotatable, the present embodiment is not limited to the above aspect.

Figure 9:
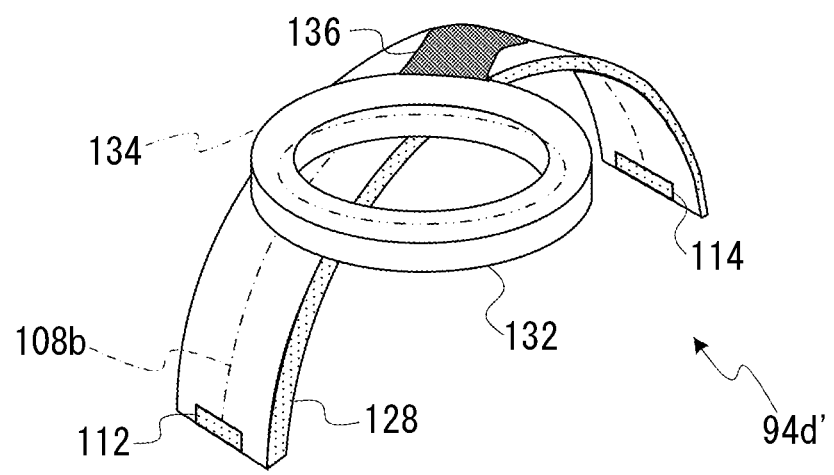
FIG. 9 is a schematic oblique perspective figure showing a modified example of the linking part of the belt member in FIG. 8.

FIG. 9 is a schematic oblique perspective figure showing a modified example of the belt member 94d in FIG. 8. The belt member 94d' in FIG. 9 is similar to the belt member 94d in FIG. 8 except that a flexible linking unit 136 is disposed instead of the rotational axis structure 130.

The flexible linking unit 136 connects the semicircular part 128 with the ring member 132, and is made of a deformable material. Materials such as FPC (Flexible Printed Circuit) can be used for this deformable part. A (flexible) conductive wire (not shown) is extending inside the flexible linking unit 136, and the coil element 134 is connected to the connector 112 via the flexible linking unit 136 and hard-wiring (not shown) inside the semicircular part 128.

Figure 10:
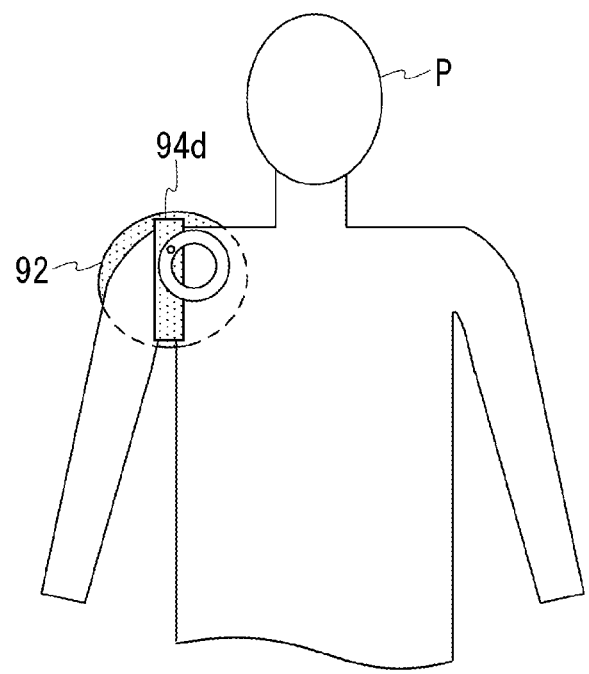
FIG. 10 is a schematic planimetric diagram showing an example of the mounting state of the RF coil device composed of the belt member in FIG. 8 and the base member in FIG. 2, under the pose in which the arm of an object is down.

FIG. 10 is a schematic planimetric diagram showing an example of the mounting state of the RF coil device 90A composed of the belt member 94d in FIG. 8 and the base member 92 in FIG. 2, under the pose in which the arm of the object P is down.

Figure 11:
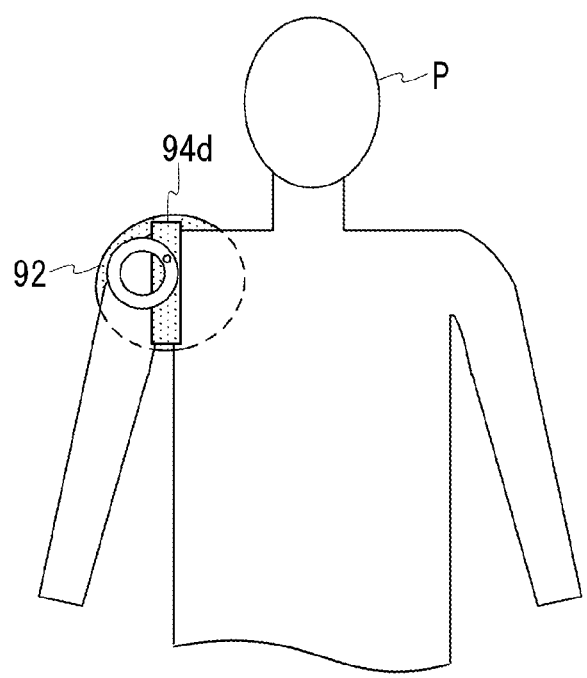
FIG. 11 a schematic planimetric diagram showing an example of the mounting state of the RF coil device, when the ring member is rotated from the position of the mounting state in FIG. 10.

FIG. 11 a schematic planimetric diagram showing an example of the mounting state of the RF coil device 90A, when the ring member 132 is rotated from the position of the mounting state in FIG. 10. By using the belt member 94d or 94d' and changing the position of the ring member 132, the sensitivity region of the coil element 134 to the object P can be appropriately changed under the state in which the RF coil device 90A is set, as shown in FIG. 10 and FIG. 11.

According to the RF coil device 90A of the first embodiment as just described, it has configuration suitable for both states in which the arm raised and the arm is put down, if any one of the belt members 94a to 94d' is used. That is, the RF coil device 90A can be effortlessly set under both poses in which the arm raised and the arm is put down.

Therefore, replacement of RF coil devices is unnecessary between imaging with the arm raised and imaging with the arm down. Thus, burden of an object can be relieved and time for replacing a plurality of RF coil devices can be abbreviated. Additionally, there is no necessity to purchase a plurality of RF coil devices as to shoulder imaging, and expense can be trimmed down.

Additionally, under the mounting state in which an object is placed supine on the bed, the anterior surface of the base member 92 is closely-attached to the back of the object, and a coil element winding around the arm of the object can be formed by connection of the partial coils 108a and 108b. That is, being different from hitherto known shoulder RF coil devices dented like a bowl, airspace between the base member 92 and the back of the object is scarcely formed, because the base member 92 is flatly-shaped. Therefore, satisfactory coil sensitivity can be obtained by the coil element composed of connection of the partial coils 108a and 108b and the coil elements 104 and 106, under both states with the arm raised and lowered.

Additionally, the base board 96 is made in the form of, for example, a flat plate, so that it can be easily placed between the bed and the back of an object under the mounting state in which the object is laid supinely on the bed. As long as it is flatly-shaped, the base board 96 does not prevent postural maintenance of an object on the bed or setting of the RF coil device 90A even if the base board 96 is largely formed. Thus, by forming the base board 96 with sufficient size and expanding the layout areas of the internal coil elements 104 and 106, insufficiency of coil sensitivity to the joint part in the case of an object with a large body frame can be prevented.

Moreover, by selecting one of the belt members 94a to 94d' according to an imaging purpose, the number of coil elements and a composite sensitivity region of coils can be changed.

According to the aforementioned first embodiment, as the RF coil device 90A for MRI, it can be effortlessly set on the shoulder under both poses in which the arm raised and lowered, and can keep sufficient coil sensitivity.

Note that, in the first embodiment, an example in which the base board 96 of the base member 92 is disk-shaped has been explained. However, this is only an example. The base board 96 may be a flat plate whose anterior surface (the frontal surface) and underside surface are rectangular or a regular tetragon. This point applies to the base board 248 of the RF coil device 90D of the fourth embodiment shown in after-mentioned FIG. 20 and the base board 96x of the RF coil device 90x shown in after-mentioned FIG. 66 and the like.

The Second Embodiment

Figure 12:
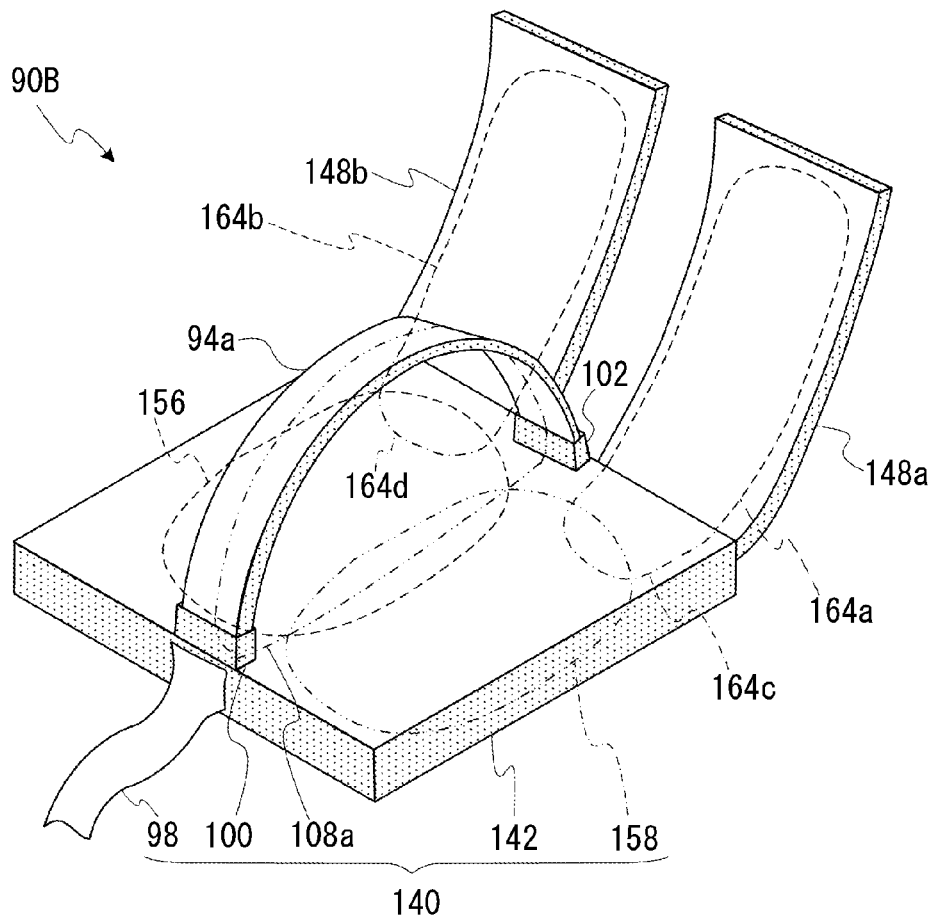
FIG. 12 is a schematic oblique perspective figure showing outline structure of the RF coil device of the second embodiment.

FIG. 12 is a schematic oblique perspective figure showing outline structure of the RF coil device 90B in the second embodiment. As shown in FIG. 12, the RF coil device 90B is composed by interdigitating (coupling) the aforementioned belt member 94a, overlay members 148a and 148b to a base member 140.

The base member 140 includes a rectangular parallelepiped base board 142, the connectors 100 and 102, and the cable 98. The underside surface and the anterior surface (the frontal surface) of the base board 142 are formed as regular tetragons. The connectors 100 and 102 are mutually separately disposed (emplaced) on the base board 142. The base board 142 is made of an undeformable material similar to the base board 96 in the first embodiment.

The connectors 100 and 102 are respectively arranged adjacent to the center of each one side of the anterior surface of the square-shaped base board 142 in such a manner that the connectors 100 and 102 are facing each other. The cable 98 is exposed from the lateral face of the connector 100 side of the base board 142.

Inside the base board 142, the partial coil 108a is disposed along the center line which evenly bisects the base board 142. One end of the partial coil 108a is connected to the connector 100, and the opposite end of the partial coil 108a is connected to the connector 102. As previously explained with FIG. 1 to FIG. 3, the partial coil 108a functions as a loop coil element by being electrically connected to the partial coil 108b inside the belt member 94a.

Additionally, loop coil elements 156 and 158 are planarly disposed inside the base board 142, so as to be in parallel with the underside surface and the anterior surface of the base board 142. For the sake of obtaining a decoupling effect, the coil elements 156 and 158 are disposed so that they partially face each other in the way similar to the coil elements 104 and 106 in the first embodiment.

In the way similar to the first embodiment, the partial coils 108a and 108b are disposed, in such a manner that "the plane overlapping on the extending regions of the conductive wires of the partial coils 108a and 108b" is orthogonal to both the underside surface and the anterior surface of the base board 142 under the interdigitation state in which both ends of the belt member 94a are interdigitated to the base board 142.

In order to achieve this, each part is configured as a stereoscopic shape, so that a semicircular transverse section of the belt member 94a is orthogonal to the underside surface and the anterior surface of the base board 142 under the above interdigitation state.

Thus, the plane overlapping on the entire loop of the coil element composed of the partial coils 108a and 108b and the plane overlapping on the entire loop of the coil element 156 or the coil element 158 are orthogonalized to each other, and their mutual coupling scarcely occurs.

Additionally, partial coils 164c and 164d indicated as chain lines in FIG. 12 are disposed inside the base board 142 on the side of the lateral face which is opposite to the exposed surface of the cable 98.

The partial coil 164c functions as a loop coil element by being electrically connected to the partial coil 164a (indicated as a dashed line in FIG. 12) arranged inside the overlay member 148a.

The partial coil 164d functions as a loop coil element by being electrically connected to the partial coil 164b (indicated as a dashed line in FIG. 12) arranged inside the overlay member 148b.

The partial coil 164c and the coil element 158 are arranged so as to partially overlap each other for obtaining a decoupling effect as shown in FIG. 12. The partial coil 164d and the coil element 156 are arranged so as to partially overlap each other for a decoupling effect as shown in FIG. 12 (this means both coils overlap each other if they are looked at from the thickness direction of the base board 142, and respective conductive wires of both coils are distantly arranged with an interval between them in the thickness direction of the base board 142. The same applies to the following explanation).

The coil elements 156 and 158, and the partial coils 108a, 164c, and 164d are electrically connected to individual hard-wirings inside the cable 98 by a circuit inside the base board 142, respectively (not shown).

The overlay members 148a and 148b are made of a flexible material so that they can deform such as axioversion. As a deformable part like this, for example, a flexible circuit board (Flexible Printed Circuit: FPC) described in Patent Document 1 can be used. That is, the partial coils 164a and 164b are composed, for example, by arranging a flexible hard-wiring such as a copper wire on a circuit board made of FPC.

Figure 13:
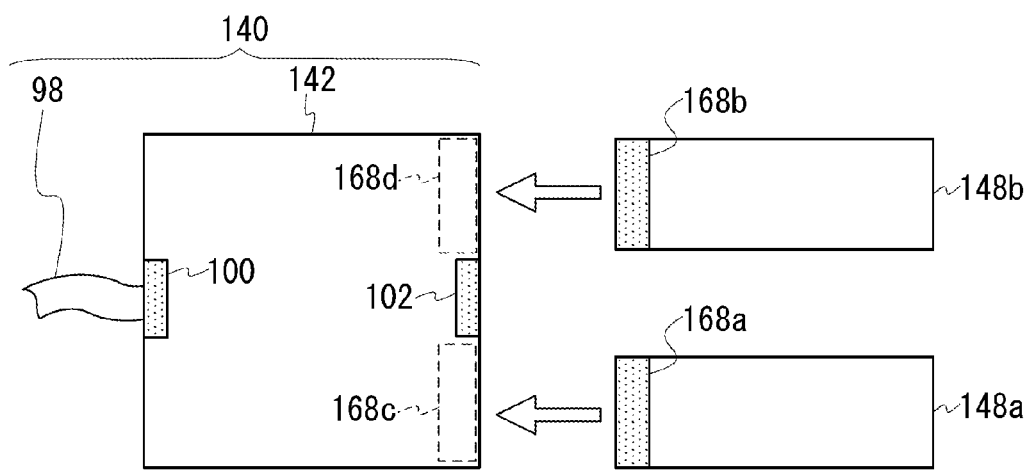
FIG. 13 is a schematic top view of the RF coil device of the second embodiment, under the state in which the belt member and the overlay member are dismounted.

FIG. 13 is a schematic top view of the RF coil device 90B, under the state in which the belt member 94a and the overlay member 148a are dismounted. The partial coils 108a, 164a, 164b, 164c and 164d, the coil elements 156 and 158, and the belt member 94a are abbreviated in FIG. 13 for simplicity.

Inside the base board 142, the connectors 168c and 168d are embedded on both sides of the connector 102 so as to be exposed on "the lateral face opposite to the exposed surface of the cable 98". Additionally, the connectors 168a and 168b are respectively disposed on the side of each one end of the overlay members 148a and 148b.

The connector 168c is shaped so as to interdigitate the side of one end including the connector 168a of the overlay member 148a. In this interdigitation state, both ends of each of the partial coils 164a and 164c in FIG. 12 are connected with each other via "electrode and the like (not shown) in the connectors 168a and 168c", and thereby the partial coils 164a and 164c function as a loop coil element.

In FIG. 13, the connector 168d is shaped so as to interdigitate the side of one end including the connector 168b of the overlay member 148b. In this interdigitation state, both ends of each of the partial coils 164b and 164d in FIG. 12 are connected with each other via "electrode and the like (not shown) in the connectors 168b and 168d", and thereby the partial coils 164b and 164d function as a loop coil element.

Figure 14:
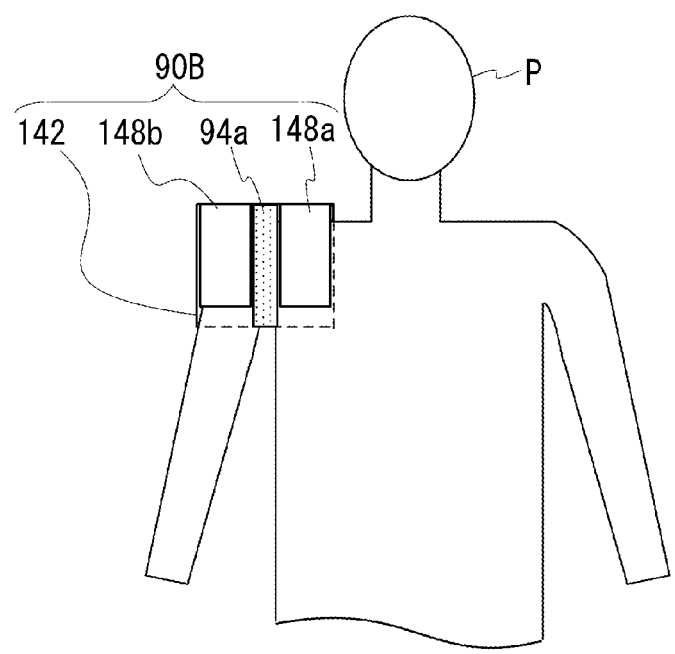
FIG. 14 is a schematic planimetric diagram showing an example of the mounting state of the RF coil device of the second embodiment, under the pose in which the arm of an object is put down.

FIG. 14 is a schematic planimetric diagram showing an example of the mounting state of the RF coil device 90B, under the pose in which the arm of the object P is put down. As shown in FIG. 14, under the state in which the RF coil device 90B is mounted, the arm of the object P is inserted to pass through the airspace (through-hole) between the belt member 94a and the base member 140.

For example, under the mounting state in which the base member 140 is attached to the back of the object P, the overlay members 148a and 148b can be arranged to overlap on the anterior surface of the object P, or they can be arranged so that they don't cover the object P. Additionally, under the mounting state in which the base member 140 is attached to the back of the object P, one or both of the overlay members 148a and 148 can be dismounted.

Figure 15:
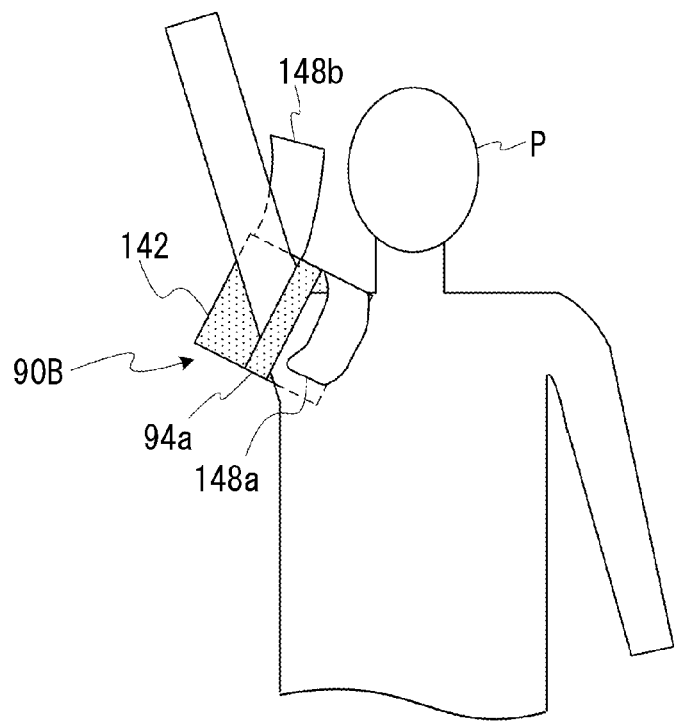
FIG. 15 is a schematic planimetric diagram showing an example of the mounting state of the RF coil device of the second embodiment, under the pose in which the arm of an object is raised.

FIG. 15 is a schematic planimetric diagram showing an example of the mounting state of the RF coil device 90B, under the pose in which the arm of the object P is raised. Here, the overlay members 148a and 148b do not prevent motion of the arm of the object P, because they are flexible. Thus, there is substantially no element which prevents the motion of the arm of the object P excluding the belt member 94a. Hence, the RF coil device 90A can be effortlessly set under both poses in which the arm is raised and lowered. Therefore, for example, as shown in FIG. 15, the overlay member 148b can be spread toward the side of the vertex of the head, and the anterior surface of the object P can be covered with the overlay member 148a.

As just described, in the second embodiment, one RF coil device 90B has a shape suitable for both poses in which the arm is raised and put down, in the way similar to the first embodiment. Therefore, replacement of an RF coil device is unnecessary between imaging with the arm raised and imaging with the arm lowered. Thus, time for replacing a plurality of RF coil devices can be abbreviated, and expense for purchasing a plurality of RF coil devices as to shoulder imaging can be saved.

Additionally, the anterior surface of the base member 140 can be closely-attached to the back of an object, and the overlay members 148a and 148b can be overlaid on the anterior surface of an object so as to be closely-attached to the anterior surface. Therefore, satisfactory coil sensitivity can be obtained by the three coil elements composed of connection of the partial coils 108a, 108b, the partial coils 164a to 164d, and the coil elements 156 and 158, under both poses in which the arm is raised and lowered.

Additionally, as long as the base board 142 is composed in the form of a flat plate, the base board 142 does not prevent postural maintenance of an object or mounting even if it is largely formed. Thus, by forming the base member 142 with sufficient size and expanding the layout areas of the internal coil elements 156 and 158, insufficiency of coil sensitivity to the joint part in the case of an object with large body frame can be prevented.

Note that, an example in which the belt member 94a is demountable and connected (coupled) to the base member 140 has been explained in the second embodiment, but this is only an example. The RF coil device may be configured by bonding the belt member 94a and the base member 140, and abbreviating the connectors 100 and 102, so that belt member 94a is nonremovable. As to the overlay members 148a and 148b, they may be similarly bonded to the base member 140 so as to become nonremovable, and similar effects can be obtained in this case. This is because the overlay members 148a and 148b is flexible, and they don't restrict motion of an object when the arm is raised and put down.

The Third Embodiment

Figure 16:
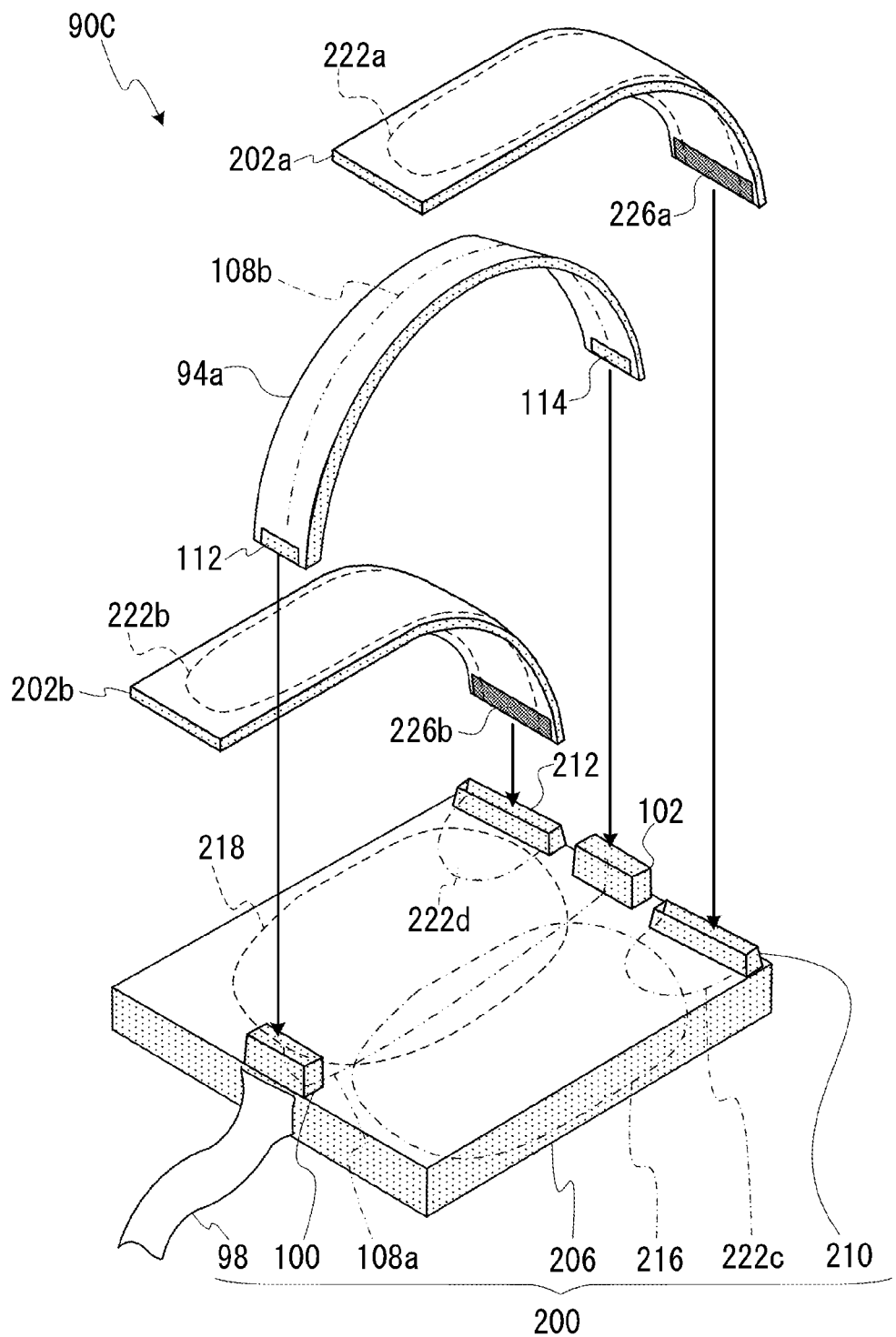
FIG. 16 is an exploded perspective view showing outline structure of the RF coil device of the third embodiment.

FIG. 16 is an exploded perspective view showing outline structure of the RF coil device 90C of the third embodiment. As shown in FIG. 16, the RF coil device 90C is composed of the base member 200, the belt member 94a, and the overlay members 202a and 202b.

The base member 200 includes a rectangular parallelopiped base board 206 whose underside surface and the anterior surface (the frontal surface) are configured in the form of a square, the cable 98, and the connectors 100, 102, 210, and 212 disposed on the base board 206. The base board 206 is made of an undeformable material such as the aforementioned FRP.

The connectors 100 and 102 are respectively arranged adjacent to the center of each one side of the square-shaped anterior surface of the base board 206, in such a manner that the connectors 100 and 102 are facing each other in the way similar to the second embodiment.

The cable 98 is exposed from the lateral face of the connector 100 side of the base board 206.

Inside the base board 206, the partial coil 108a is disposed along the center line which evenly bisects the base board 206. One end of the partial coil 108a is connected to the connector 100, and the opposite end of the partial coil 108a is connected to the connector 102. As previously explained, the partial coil 108a functions as a loop coil element by being connected to the partial coil 108b inside the belt member 94a.

Additionally, loop coil elements 216 and 218 are planarly disposed (emplaced) inside the base board 206, so as to be in parallel with the underside surface and the anterior surface of the base board 206. For the sake of obtaining a decoupling effect, the coil elements 216 and 218 are disposed, in such a manner that they partially overlap each other in the way similar to the second embodiment.

In the way similar to the second embodiment, the partial coils 108a and 108b are disposed, so that the plane overlapping on the extending regions of the conductive wires of the partial coils 108a and 108b is orthogonal to both of the underside surface and the anterior surface of the base board 206 under the interdigitation state in which both ends of the belt member 94a are interdigitated to the base board 206.

In order to achieve this, each part is configured as a stereoscopic shape, so that a semicircular transverse section of the belt member 94a is orthogonal to the underside surface and the anterior surface of the base board 206 under the above interdigitation state.

Thus, the plane overlapping on the entire loop of the coil element composed of the partial coils 108a and 108b and the plane overlapping on the entire loop of the coil element 216 or the coil element 218 are orthogonalized to each other, and their mutual coupling scarcely occurs.

Additionally, partial coils 222c and 222d indicated as chain lines in FIG. 16 are disposed inside the base board 206 on the side of the lateral face which is opposite to the exposed surface of the cable 98.

The partial coil 222c functions as a loop coil element by being connected to the partial coil 222a (indicated as a dashed line in FIG. 16) disposed inside the overlay member 202a.

The partial coil 222d functions as a loop coil element by being connected to the partial coil 222b (indicated as a dashed line in FIG. 16) disposed inside the overlay member 202b.

For the sake of obtaining a decoupling effect, the partial coil 222c and the coil element 216 are arranged so as to partially overlap each other, and the partial coil 222d and the coil element 218 are arranged so as to partially overlap each other.

The coil elements 216, 218, and the partial coils 108a, 222c and 222d are electrically connected to individual hard-wirings inside the cable 98 by a circuit inside the base board 206, respectively (not shown).

Each of the overlay members 202a and 202b has the mutually same structure, and their shape is obtained by bending a half in the side of one end of a plate in an arc while the remaining half of the plate is kept flat. The overlay members 202a and 202b are made of an undeformable material such as the aforementioned FRP.

The overlay member 202a includes the partial coil 222a disposed from the side of one end to the side of the opposite end inside it and the connector 226a disposed on the side of one end thereof.

Similarly, the overlay member 202b includes the partial coil 222b disposed from the side of one end to the side of the opposite end inside it and the connector 226b disposed on the side of one end thereof.

The connector 210 of the base member 200 is shaped so as to interdigitate the side of one end including the connector 226a of the overlay member 202a. In this interdigitation state, both ends of each of the partial coils 222a and 222c are connected with each other via electrode and the like (not shown) in the connectors 226a and 210, and thereby the partial coils 222a and 222c function as a loop coil element.

Similarly, the connector 212 of the base member 200 is shaped so as to interdigitate the side of one end including the connector 226b of the overlay member 202b. In this interdigitation state, both ends of each of the partial coils 222b and 222d are connected with each other via electrode and the like (not shown) in the connectors 226b and 212, and thereby the partial coils 222b and 222d function as a loop coil element.

Figure 17:
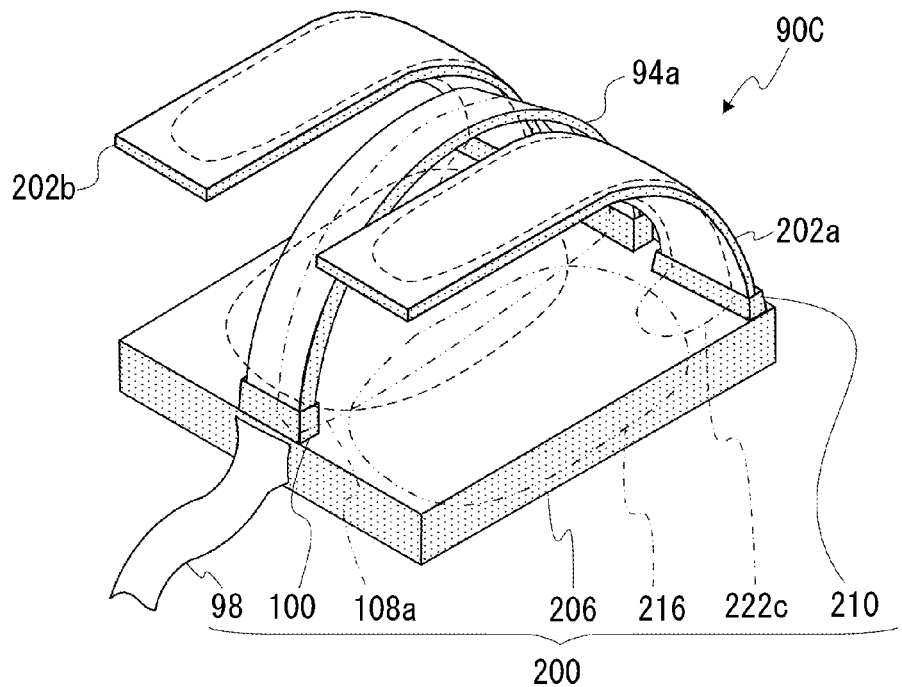
FIG. 17 is a schematic oblique perspective figure showing an overview when the respective parts of the RF coil device of the third embodiment are connected to each other.

FIG. 17 is a schematic oblique perspective figure showing an overview when the respective parts of the RF coil device 90C are connected to each other, as one of its mounting states. As shown in FIG. 17, in the RF coil device 90C, the belt member 94a and the overlay members 202a and 202b can be respectively interdigitated (coupled) to the base member 200. Additionally, the RF coil device 90C is constitutionally symmetric across the extending line of the partial coil 108a.

In the combined state, there is airspace between the base member 200 and the parts of the overlay members 202a and 202b located opposite to the connectors 226a and 226b (see FIG. 16). The RF coil device 90C can be set by letting the arm pass through this airspace and the airspace between the belt member 94a and the base member 200.

Figure 18:
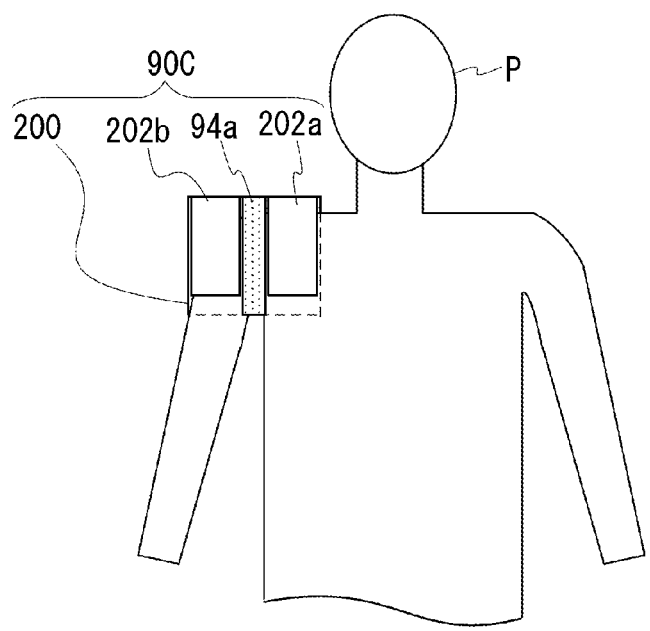
FIG. 18 is a schematic planimetric diagram showing an example of the mounting state of the RF coil device of the third embodiment, under the pose in which the arm of an object is put down.

FIG. 18 is a schematic planimetric diagram showing an example of the mounting state of the RF coil device 90C, under the pose in which the arm of the object P is put down. In this example, the base member 200 is closely-attached to the back of the object P. Under the pose in which the arm of the object P is put down, both of the overlay members 202a and 202b may be combined to the base member 200 as shown in FIG. 18. Alternatively, under the pose in which the arm is put down, both or one of the overlay members 202a and 202b may be dismounted.

Figure 19:
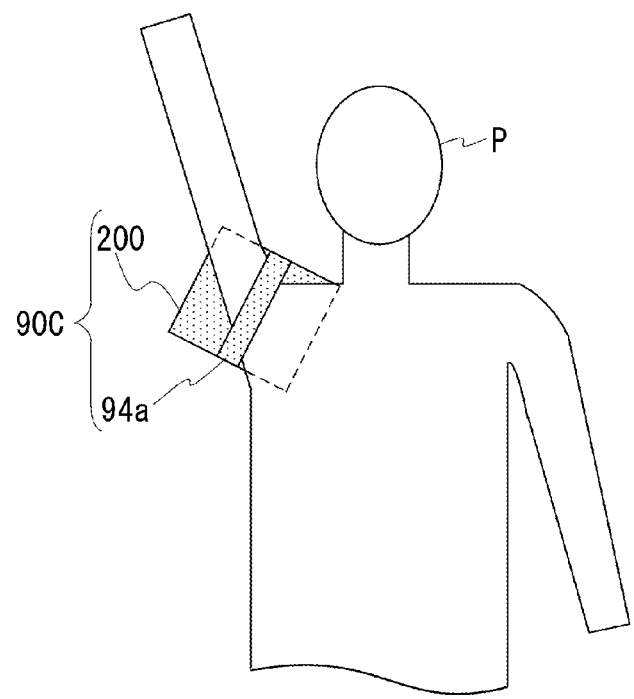
FIG. 19 is a schematic planimetric diagram showing an example of the mounting state of the RF coil device of the third embodiment, under the pose in which the arm of an object P is raised.

FIG. 19 is a schematic planimetric diagram showing an example of the mounting state of the RF coil device 90C, under the pose in which the arm of the object P is raised.

When the object P raises the arm from the pose in which the arm is put down and the RF coil device 90C is set on the shoulder, this motion can be achieved by dismounting the overlay members 202a and 202b. Thereby, nothing prevents the motion of the arm of the object P except the belt member 94a, and the RF coil device 90C can be effortlessly set under both poses in which the arm is raised and lowered, in the way similar to the second embodiment.

As just described, because the RF coil device 90C is functionally equal to the RF coil device 90A composed of the base member 92 and the belt member 94a in the first embodiment under the state without the overlay members 202a and 202b, similar effects can be obtained in the third embodiment.

Additionally, in the case of enhancing the coil sensitivity on the side of the anterior surface of object P in imaging under the pose with the arm down, this can be achieved by using one or both of the overlay members 202a and 202b.

Even if the overlay members 202a and 202b are combined to the RF coil device 90C, an object can shift the pose from the state with the arm raised to the state with the arm down without replacing the RF coil device 90C, and vice versa. This is because the overlay members 202a and 202b are demountable. Thus, effects similar to the second embodiment can be obtained.

Note that, in the third embodiment, an example in which the belt member 94a is connected to the base member 200 in a dismountable manner has been explained. However, this is only an example. The RF coil device may be configured by bonding the belt member 94a and the base member 200 omitting the connectors 100 and 102 and the like.

Additionally, an example in which both surfaces of the base member 200 are in the form of a regular tetragon has been explained, but this is only an example. For example, the base member may be configured in the form of a disk like in the first embodiment.

The Fourth Embodiment

The RF coil device 90D of the fourth embodiment is almost equal to the structure obtained by adding a hinge instead of the connectors 102 and 114 to the structure of the first embodiment, in such a manner that the side of one end of the belt member 94a is pivotally (rotatably) fixed to the base member 92.

Figure 20:
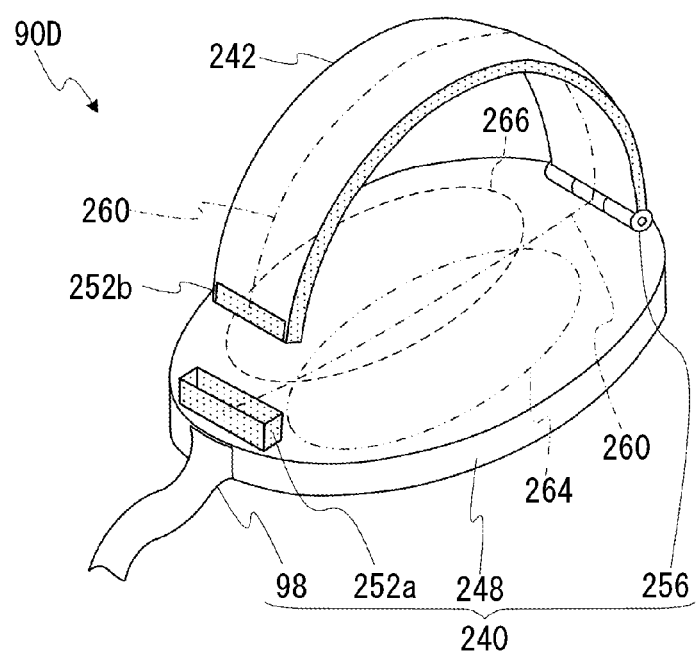
FIG. 20 is a schematic oblique perspective figure showing outline structure of the RF coil device of the fourth embodiment, under the state in which one end of the belt member is separated from the base member.
Figure 21:
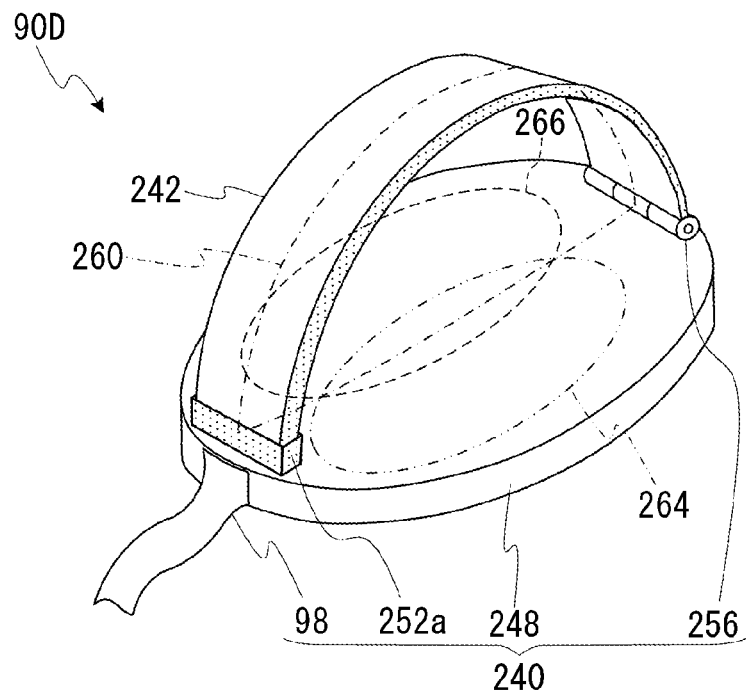
FIG. 21 is a schematic oblique perspective figure showing outline structure of the RF coil device of the fourth embodiment, under the state in which one end of the belt member is interdigitated to the base member.

FIG. 20 and FIG. 21 are schematic oblique perspective figures showing outline structure of the RF coil device 90D of the fourth embodiment. FIG. 20 shows the state in which one end of the belt member 94a is separated from the base member 240. FIG. 21 shows the state in which the one end of the belt member 94a is interdigitated to the base member 240 by rotation.

Figure 22:
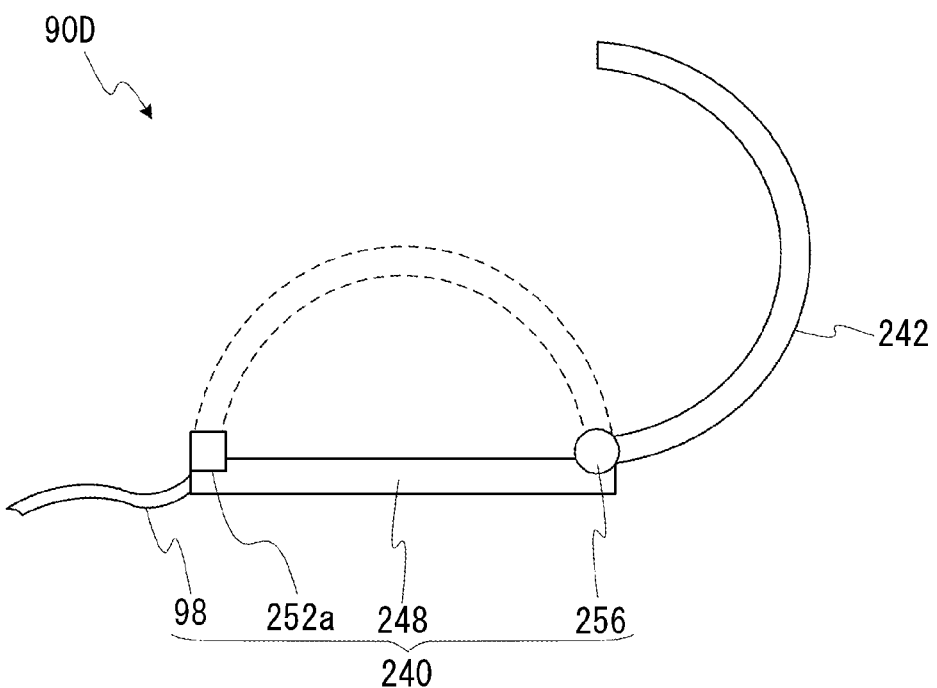
FIG. 22 is a schematic lateral view showing the rotational motion of the RF coil device of the fourth embodiment.

FIG. 22 is a schematic lateral view of the RF coil device 90D showing the rotational motion of the belt member 242.

As shown in these FIG. 20 to FIG. 22, the RF coil device 90D is composed of the base member 240 and the belt member 242 rotatably fixed to this base member 240.

As shown in FIG. 20, the base member 240 includes a disk-shaped base board 248, the cable 98, a connector 252a and a hinge structure 256. The connector 252a and the hinge structure 256 are disposed on the base board 248. The belt member 242 is in the shape of a semicircularly bent plate, similar to the belt member 94a in the first embodiment. The side of one end of the belt member 242 is fixed by the hinge structure 256, and the belt member 242 includes a connector 252b on the side of the opposite end. The base board 248 and the belt member 242 are made of an undeformable material such as aforementioned FRP. The cable 98 is exposed from the lateral face on the side of the connector 252a in the base board 248.

The hinge structure 256 is disposed on "the outer border of the anterior surface (the frontal surface) of the base member 240", opposite to the cable 98. As shown in FIG. 22, the hinge structure 256 holds the belt member 242 rotatable in one predetermined (unchanged) plane orthogonal to both surfaces of the disk-shaped base board 248. In FIG. 22, the dashed lines indicate the belt member 242, under the state in which the one end of the belt member 242 is interdigitated (coupled) to the base member 240.

As shown in FIG. 20, inside the base board 248, a part of the coil element 260 is disposed (emplaced) along the center line evenly bisecting the base board 248, and is indicated as a chain line. The rest of the coil element 260 is disposed from one end to the opposite end inside the belt member 242, extending (passing) inside of the hinge structure 256.

One end of the coil element 260 is connected to the connector 252a, and the opposite end of the coil element 260 is connected to the connector 252b in the belt member 242.

On the anterior surface of the base member 240, the connector 252a is located in the part opposite to the hinge structure 256. The connector 252a is shaped so that it interdigitates the side of the opposite end including the connector 252b of the belt member 242. In this interdigitation state, both ends of the coil element 260 are connected with each other via electrode and the like (not shown) in the connectors 252a and 252b, and thereby the coil element 260 functions as a loop coil element.

Additionally, loop coil elements 264 and 266 are disposed inside the base board 248 under the arrangement similar to the coil elements 104 and 106 in the first embodiment, in such a manner that each of the coil elements 264 and 266 becomes a loop which is in parallel with the underside surface and the anterior surface of the base board 248.

In FIG. 20, the coil element 264 is indicated as a two-dot chain line, the coil element 266 is indicated as a dashed line. For the sake of obtaining a decoupling effect, the coil element 264 and 266 are disposed, in such a manner that they partially overlap each other in the way similar to the aforementioned embodiments.

Additionally, though the above coil element 260 corresponds to the partial coils 108a and 108b in terms of arrangement, the cross-sectional area of the loop conductive wire of the coil element 260 is bigger than that of the coil elements 264 and 266. These coil elements 260, 264, and 266 are connected to individual hard-wirings inside the cable 98 by a circuit inside the base board 248, respectively (not shown).

Note that, like in the first embodiment, the coil element 260 is disposed, in such a manner that the plane overlapping on the extending region of the conductive wire of the coil element 260 is orthogonal to the underside surface and the anterior surface of the base board 248 under the state in which the belt member 242 is interdigitated to the connector 252a.

In order to achieve this, each part is configured as a stereoscopic shape, so that a semicircular transverse section of the belt member 242 is orthogonal to the underside surface and the anterior surface of the base board 248 under the above interdigitation state.

Thus, the plane overlapping on the entire loop of the coil element 260 and the plane overlapping on the entire loop of the coil element 264 or the coil element 266 are orthogonalized to each other, and their mutual coupling scarcely occurs.

As just described, the RF coil device 90D of the fourth embodiment is almost equal to the structure in which the side of one end of the belt member 94a is rotatably fixed to the base member 92 in the first embodiment. Thus, the mounting method of the RF coil device 90D is similar to the first embodiment. Therefore, in the fourth embodiment, the same effects as the RF coil device 90A composed of the belt member 94a and the base member 92 in the first embodiment can be obtained.

Additionally, in the fourth embodiment, the cross-sectional area of the conductive wire of the coil element 260 passing the entire loop composed of a part of the inside of the belt member 242 and a part of the inside of the base member 240 is large. Thus, coil sensitivity is improved near the coil element 260 arranged on both of the anterior surface and the back surface of an object, in the mounting state.

Figure 23:
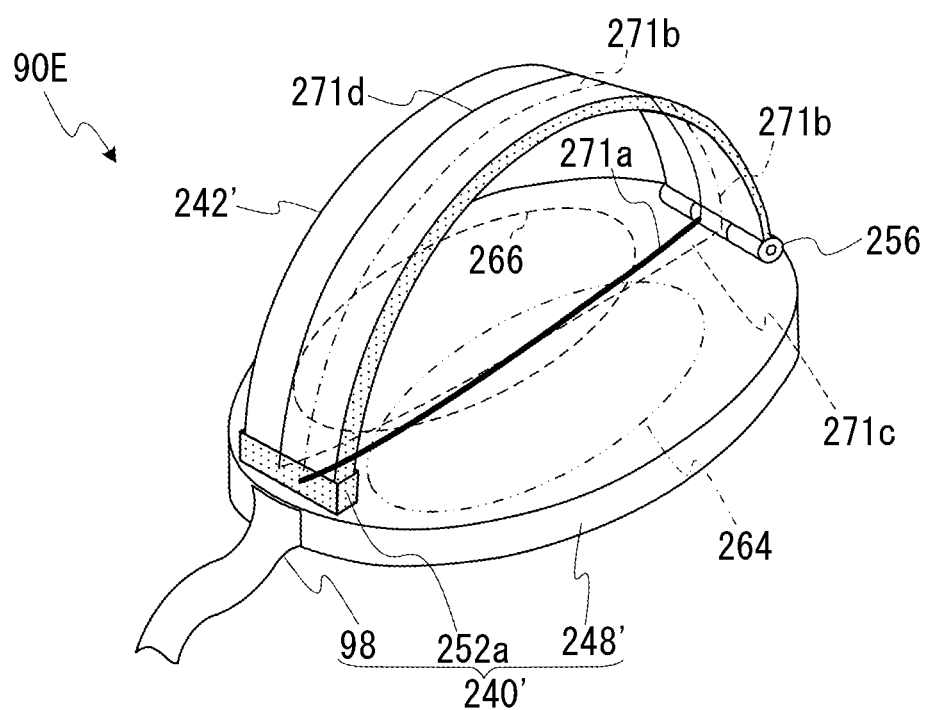
FIG. 23 is a schematic oblique perspective figure showing outline structure of an RF coil device as a supplementary embodiment of the fourth embodiment.

FIG. 23 is a schematic oblique perspective figure showing outline structure of the RF coil device 90a as a supplementary embodiment of the fourth embodiment.

The RF coil device 90E shown in FIG. 23 is the same as the above RF coil device 90D except that another coil element is emplaced instead of the coil element 260 whose conductive wire is large in the cross-sectional area in the arrangement similar to the coil element 260.

The aforementioned another coil element is coded as 271 for the sake of simplicity. Because this coil element 271 is the combination of the following sections 271a, 271b, 271c and 271d, symbol 271 is not shown in FIG. 23.

The coil element 271 is a coil element winded by two turns. In FIG. 23, in order for its hard-wiring to be understandable, the coil element 271 is divided into four sections 271a, 271b, 271c and 271d. These sections 271a, 271b, 271c and 271d are shown in FIG. 23.

The first section 271a indicated as a bold line in FIG. 23 is a section disposed inside the base board 248', and the second section 271b indicated as a chain line is a section disposed inside the belt member 242'. The third section 271c indicated as a dashed line is a section disposed inside the base board 248', and the fourth section 271d indicated as a solid line is a section disposed inside the belt member 242'.

The first section 271a and the third section 271c intersect with each other inside the base board 248'. The second section 271b and the fourth section 271d are separated with a uniform interval inside the belt member 242'.

Thereby, the current pathway of the coil element 271 has a trajectory obtained by folding the figure of eight in the way the folding line passes the intersection point (center) of the figure of eight.

If the current pathway is described from the place of the hinge structure 256 as an example, it becomes a loop passing the first section 271a, the second section 271b, the third section 271c, the fourth section 271d, and the first section 271a, in order. The coil element 271 is connected to a hard-wiring inside the cable 98 by a circuit inside the base board 248, individually (not shown).

As just described, coil sensitivity can be improved by increasing the number of turns of one coil element, instead of increasing the cross-sectional area of the conductive wire.

Note that, an example in which the base board 248 is disk-shaped has been explained in the fourth embodiment. However, this is only an example. For example, the base board 248 may be in the form of a flat plate whose underside surface and anterior surface are regular tetragons, rectangles or hexagons.

Additionally, an example in which the belt member 242 is semicircularly curved has been explained in the fourth embodiment. However, this is only an example. For example, the belt member 242 may be in the form of an angled-bracket.

The Fifth Embodiment

Figure 24:
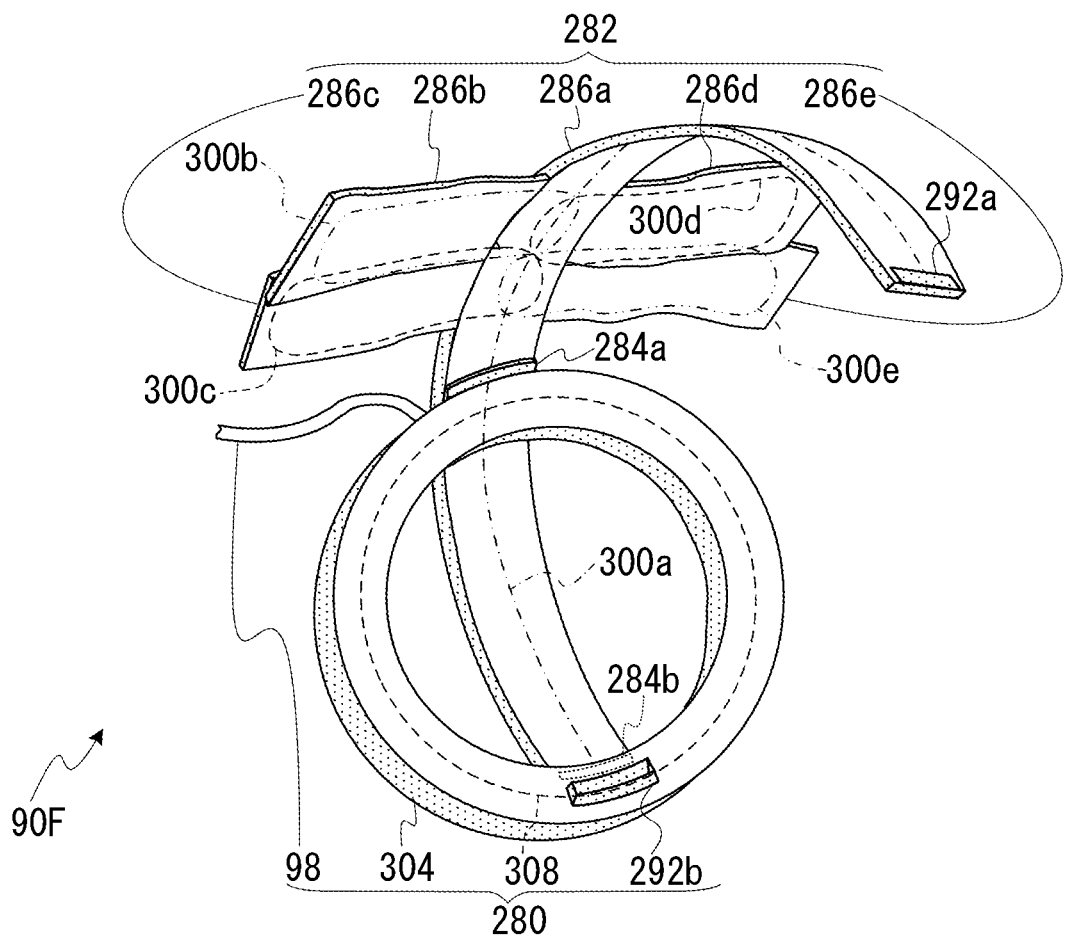
FIG. 24 is a schematic oblique perspective figure showing outline structure of the RF coil device of the fifth embodiment.

FIG. 24 is a schematic oblique perspective figure showing outline structure of the RF coil device 90F of the fifth embodiment. As shown in FIG. 24, the RF coil device 90F has a structure of fixing a band member 282 at two places of a ring-shaped base member 280 with bonding members 284a and 284b.

The band member 282 has a structure of forming the zonal belt member 286a, the flap members 286b, 286c, 286d, and 286 in an integrated fashion. The belt member 286a, the flap members 286b, 286c, 286d, and 286 are flexible, because these are made of the aforementioned FPC and the like.

The one end of the belt member 286a is fixed to the base member 280 with the bonding member 284b, and the belt member 286a includes the connector 292a on the side of its opposite end. "The part of the belt member 286a slightly closer to the side of the one end than its center" is fixed to the base member 280 with the bonding member 284a.

Inside the belt member 286a, a coil element 300a is disposed (emplaced) from its one end to the opposite end. One end of the coil element 300a is electrically connected to the connector 292a, and the opposite end of the coil element 300a is electrically connected to the connector 292b via the inside of the base member 280. Both ends of the coil element 300a are electrically connected to each other by the connection of the connectors 292a and 292b, and thereby the coil element 300a functions as a loop coil.

The loop coil elements 300b, 300c, 300d, and 300e are respectively arranged inside the flap members 286b, 286c, 286d, and 286e so as to extend over the inside of the belt member 286a. The flap members 286b and 286c are fixed to the belt member 286a, so that the flap members 286b and 286c partially overlap on each other. The flap members 286d and 286e are fixed to the belt member 286a, so that they partially overlap on each other. This is for the sake of obtaining a decoupling effect. That is, the coil elements 300b, 300c, 300d, and 300e partially overlap each other if they are planarly looked at (see after-mentioned FIG. 25).

The base member 280 includes a circular ring member 304, the connector 292b disposed on the ring member 304, and the cable 98 exposed from the lateral face of the ring member 304. The ring member 304 is made of an undeformable material such as the aforementioned FRP. Additionally, inside the ring member 304, a loop coil element 308 indicated as a dashed line in FIG. 24 is disposed.

The coil elements 300a, 300b, 300c, 300d, 300e, and 308 are connected to individual hard-wirings inside the cable 98 by a circuit (not shown) inside the belt member 286a and the ring member 304, respectively.

The connector 292b is shaped so as to interdigitate the side of one end including the connector 292a of the belt member 286a. In this interdigitation state, both ends of the coil element 300a are electrically connected to each other by electrode and the like inside the connectors 292a and 292b.

Figure 25:
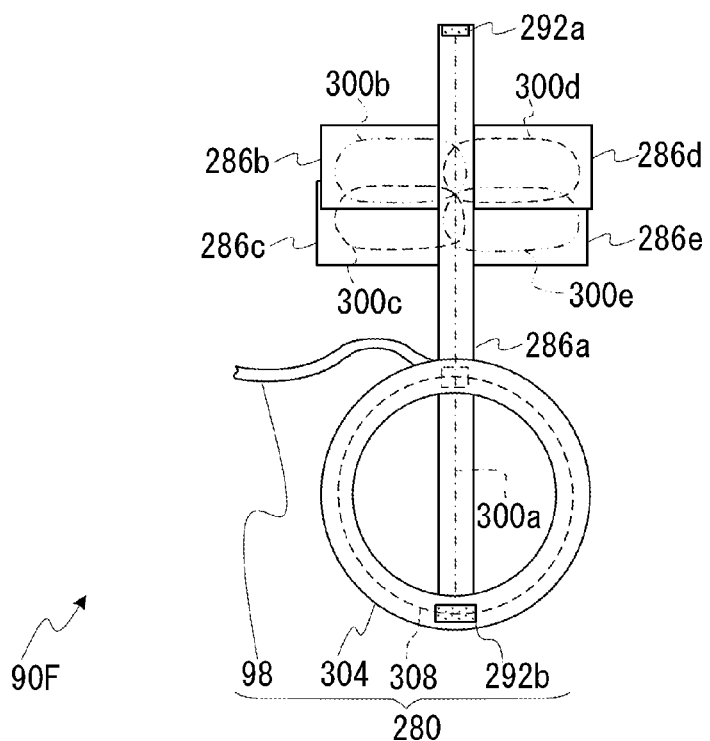
FIG. 25 is a schematic planimetric diagram of the RF coil device of the fifth embodiment showing the state in which the band member is unfolded.

FIG. 25 is a schematic planimetric diagram of the RF coil device 90F showing the state in which the band member 282 is spread. The coil elements 300b, 300c, 300d, and 300e are symmetrically disposed so that the extending line of the coil element 300a becomes a line-symmetric axis.

For the sake of obtaining a decoupling effect, the coil element 300b is arranged so as to partially overlap the coil elements 300c and 300d if they are planarly looked at. Similarly, the coil element 300e is arranged so as to partially overlap the coil elements 300c and 300d if they are planarly looked at.

Figure 26:
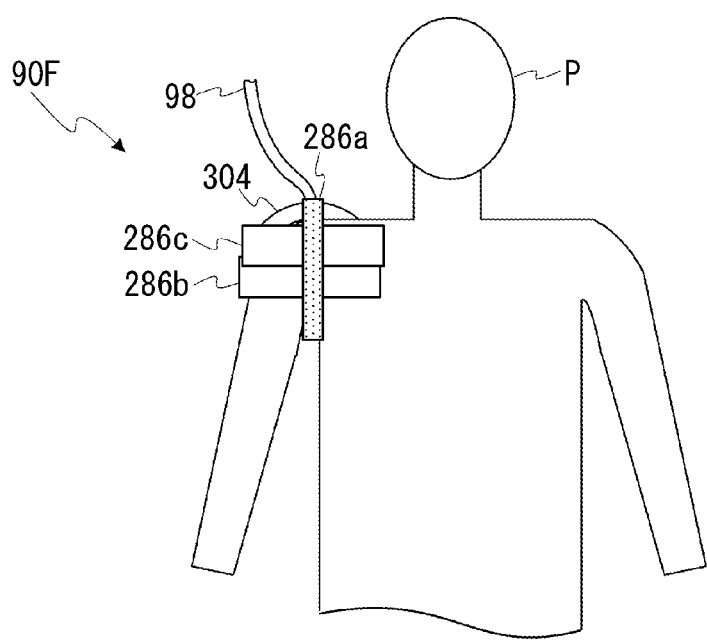
FIG. 26 is a schematic planimetric diagram showing an example of the mounting state of the RF coil device of the fifth embodiment, under the pose in which the arm of an object is put down.

FIG. 26 is a schematic planimetric diagram showing an example of the mounting state of the RF coil device 90F, under the pose in which the arm of the object P is put down. As an example of its mounting method, one end of the belt member 286a is interdigitated to the connector 292b of the base member 280 so as to wind the side of the root of the arm with the belt member 286a, under the state in which the base member 280 is closely-attached to the back of the shoulder of the object P.

As shown in FIG. 26, though the anterior surface of the object P is covered with the four flap members 286b, 286c, 286d and 286e, the flap members 286b, 286c, 286d and 286e hardly prevent the motion of the arm of the object P because they are flexible.

Figure 27:
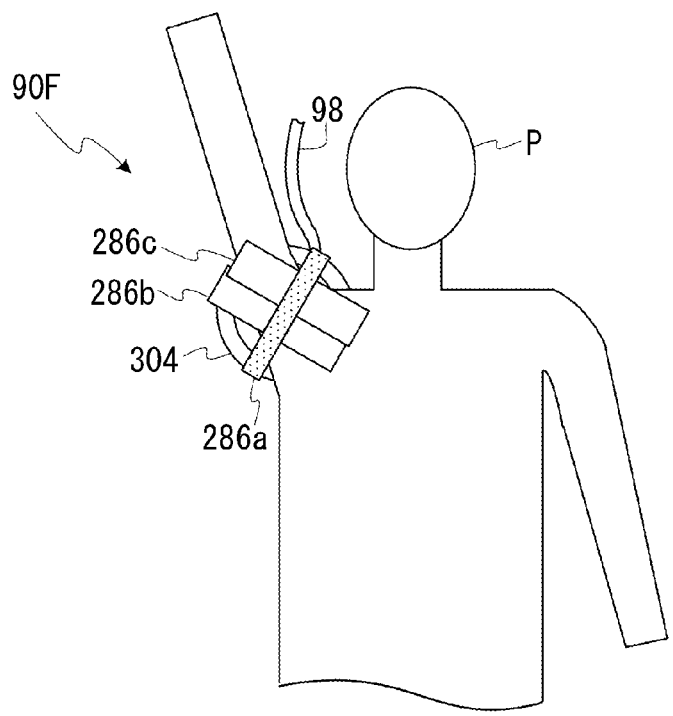
FIG. 27 is a schematic planimetric diagram showing an example of the mounting state of the RF coil device of the fifth embodiment, under the pose in which the arm of an object is raised.

FIG. 27 is a schematic planimetric diagram showing an example of the mounting state of the RF coil device 90F, under the pose in which the arm of the object P is raised. Here, there is substantially nothing to prevent the motion of the arm of the object P, except the belt member 286a mounted so as to wind the arm around. Thus, the object can effortlessly raise or put down the arm, with the RF coil device 90 mounted on the shoulder.

As just described, because one RF coil device 90F has a shape suitable for both poses in which the arm raised and lowered, the RF coil device 90F of the fifth embodiment can be effortlessly set on the shoulder under both poses with the arm raised and lowered.

Thus, the effects similar to the second embodiment can be obtained in the fifth embodiment. Additionally, the four loop coil elements 300b, 300c, 300d and 300e are closely-attached to the anterior surface of an object by the four flap members 286b, 286c, 286d and 286e in its mounting state. Therefore, wide and satisfactory coil sensitivity can be obtained especially on the side of the anterior surface of an object.

Note that, an example in which the base member 280 is made in the form of a ring (by the ring member 304) has been explained in the fifth embodiment. However, this is only an example. For example, the base member 280 may be disk-shaped like the one in the first embodiment or in the form of a thin plate whose surfaces are both approximately square like the one in the second embodiment.

The Sixth Embodiment

Figure 28:
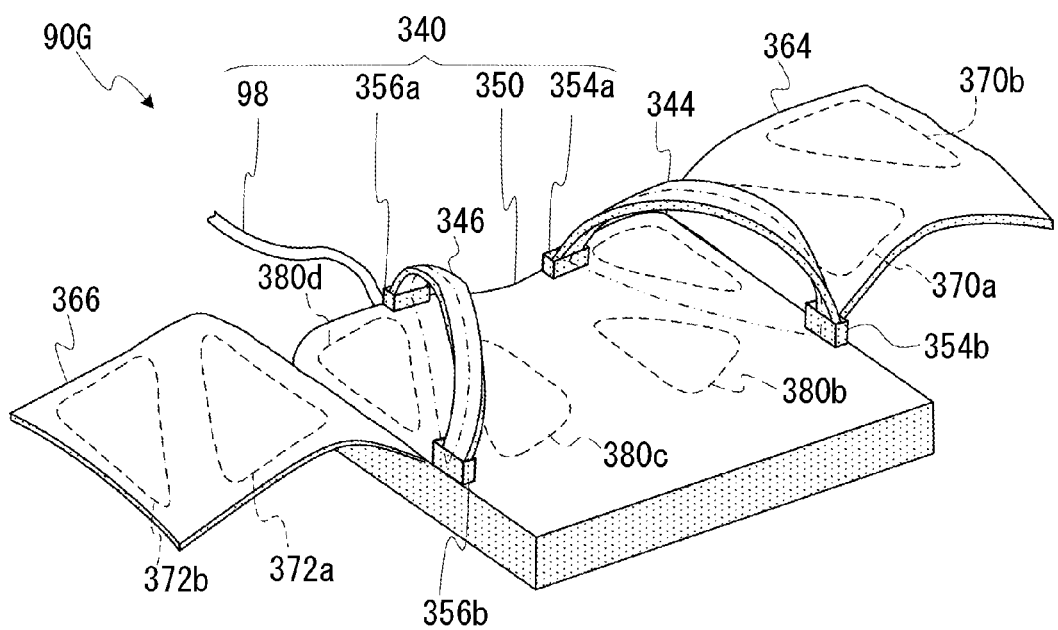
FIG. 28 is a schematic oblique perspective figure showing outline structure of the RF coil device of the sixth embodiment, under the state in which two belt members are combined.
Figure 29:
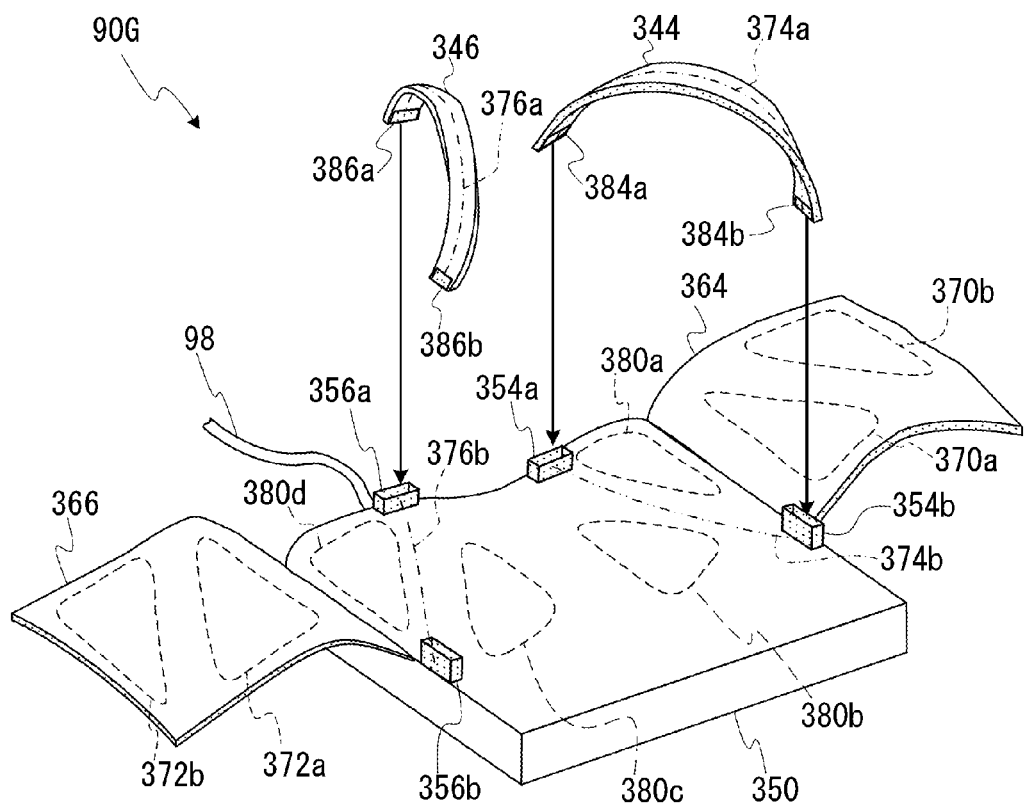
FIG. 29 is an exploded perspective view showing outline structure of the RF coil device of the sixth embodiment, under the state in which two belt members are dismounted.

FIG. 28 is a schematic oblique perspective figure showing outline structure of the RF coil device 90G of the sixth embodiment. FIG. 29 is an exploded perspective view showing the state in which two belt members are dismounted from the RF coil device 90G.

As shown in FIG. 28 and FIG. 29, the RF coil device 90G is composed by interdigitating (coupling) two belt members 344 and 346 to a base member 340. The belt members 344 and 346 include partial coils inside them as a part of a coil element.

The RF coil device 90G is constituted so as to overlay both shoulders from above with the two belt members 344 and 346. Alternatively, the RF coil device 90G is constituted so as to let both arms respectively pass through the airspace between the belt member 344 and the base member 340 and the airspace between the belt member 346 and the base member 340. Therefore, the RF coil device 90G has a bilaterally symmetric structure.

As shown in FIG. 28, the base member 340 includes a base board 350, connectors 354a, 354b, 356a and 356b, and the cable 98. The connectors 354a, 354b, 356a and 356b are disposed on the base board 350. The base board 350 is made in the form of a flat plate, both faces thereof are approximately rectangular (the base board 350 is an approximately rectangular parallelopiped, composed of the underside surface, the anterior surface, and four side surfaces). The base board 350 is made of an undeformable material such as the FRP.

On the anterior surface (frontal surface) of the base board 350, the connector 354a and 356a are mutually distantly disposed adjacent to the outer border on the side of the cable 98 with an interval which is, for example, approximately 30 cm.

Figure 30:
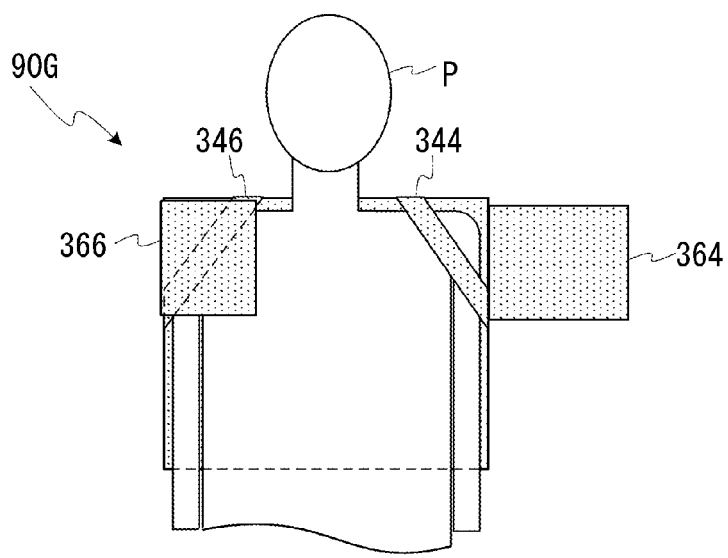
FIG. 30 is a schematic planimetric diagram showing an example of the mounting state of the RF coil device of the sixth embodiment, under the pose in which the arms of an object are put down.
Figure 31:
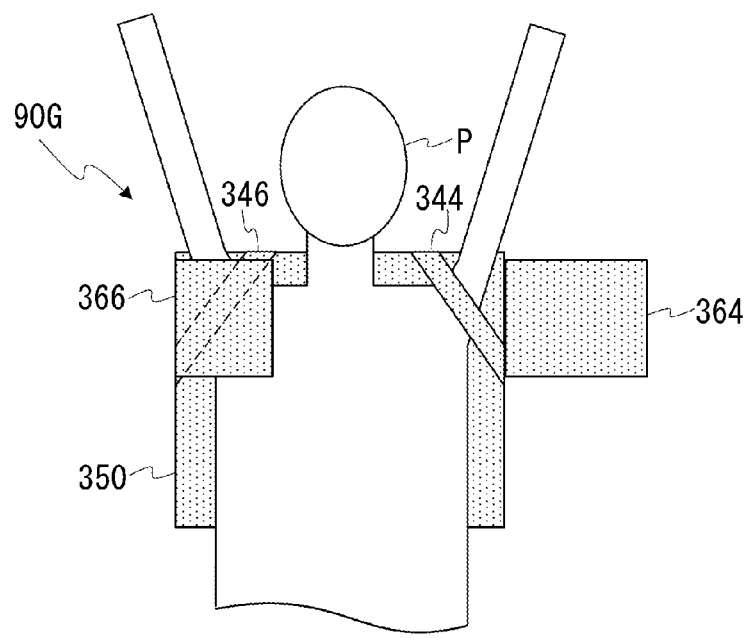
FIG. 31 is a schematic planimetric diagram showing an example of the mounting state of the RF coil device of the sixth embodiment, under the pose in which the arms of an object are raised.

This interval is set slightly narrower than the width between both shoulders of an average human body, considering the aforementioned mounting state of the RF coil device 90G to an object (see after-mentioned FIG. 30 and FIG. 31).

Additionally, the part of the anterior surface of the base board 350 between the connector 354a and the connector 356a is chamfered so as to become smoothly dent, because this part is closely-attached to the neck of an object.

On the base board 350, the overlay members 364 and 366 are respectively fixed to two lateral surfaces adjacent to the lateral surface from which the cable 98 is exposed.

On the exterior edge of the anterior surface of the base board 350, the connector 354b is located at the place which is separated from the interface between the overlay member 364 and the base board 350 by, for example, approximately 1 centimeter. On the outer rim of the anterior surface of the base board 350, the connector 356b is located at the place which is separated from the interface between the overlay member 366 and the base board 350 by, for example, approximately 1 centimeter.

On the outer rim of the anterior surface of the base board 350, the connector 356b is located at the place which is separated from "the interface between the overlay member 366 and the base board 350" by, for example, approximately 1 centimeter.

As shown in FIG. 29, inside the base board 350, the partial coil 374b is located (emplaced) at the region connecting the connector 354a with the connector 354b, and the partial coil 376b is located at the region connecting the connector 356a with the connector 356b.

Inside the base board 350, a coil element 380a is disposed (emplaced) on the side of the overlay member 364 and a coil element 380b is disposed on the opposite side, in such a manner that their arrangement is symmetric and the extending line of the partial coil 374b becomes its line-symmetric axis.

Similarly, inside the base board 350, a coil element 380d is disposed on the side of the overlay member 366 and a coil element 380c is disposed on the opposite side, in such a manner that their arrangement is symmetric and the extending line of the partial coil 376b becomes its line-symmetric axis.

The coil elements 380a to 380d are in the form of a loop obtained by rounding each vertex of outline of a right-angled triangle. Additionally, the coil elements 380a to 380d are planarly arranged, in such a manner that their conductive wire parts are in parallel with the underside surface and the anterior surface of the base board 350.

The overlay members 364 and 366 are made of a flexible material such as FPC, and foldable. Inside the overlay member 364, the coil element 370a is disposed on the side of the base board 350 and the coil element 370b is disposed on the opposite side.

Similarly, inside the overlay member 366, the coil element 372a is disposed on the side of the base board 350 and the coil element 372b is disposed on the opposite side. These coil elements 370a, 370b, 372a, and 372b are in the form of a loop obtained by rounding each vertex of outline of a right-angled triangle, and they are mutually separately disposed with an interval so that coupling effect scarsly occurs.

The partial coils 374b and 376b, the coil elements 380a, 380b, 380c and 380d, and the coil elements 370a, 370b, 372a, 372b are electrically connected to individual hard-wirings inside the cable 98 by a circuit inside the overlay members 364 and 366 and the base board 350, respectively (not shown).

As shown in FIG. 29, the belt members 344 and 346 have a shape obtained by bending and twisting a zonal plate to become semicircular. The belt members 344 and 346 have mutually similar structure except that they are mutually symmetric. The belt members 344 and 346 are made of an undeformable material such as the FRP.

The belt member 344 includes a connector 384a on the side of its one end and a connector 384b on the side of the opposite end. A partial coil 374a is disposed from the one end to the opposite end inside the belt member 344.

Similarly, the belt member 346 includes a connector 386a on the side of its one end and a connector 386b on the side of the opposite end. A partial coil 376a is disposed from one end to the opposite end inside the belt member 346.

The connector 354a on the base board 350 is shaped so as to interdigitate the side of one end including the connector 384a of the belt member 344. The connector 354b on the base board 350 is shaped so as to interdigitate the side of the opposite end including the connector 384b of the belt member 344.

When both ends of the belt member 344 are interdigitated to the connectors 354a and 354b, both ends of each of the partial coils 374a and 374b are connected with each other via "electrode and the like (not shown) in the connectors 354a, 354b, 384a and 384b", and thereby the partial coils 374a and 374b become a loop coil element.

In the way similar to the first embodiment, the partial coils 374a and 374b are disposed, so that the plane overlapping on the extending region of the conductive wire of the partial coils 374a and 374b is orthogonal to the underside surface and the anterior surface of the base board 350 under the state in which both ends of the belt member 344 are interdigitated to the base board 350.

In order to achieve this, each part is configured as a stereoscopic shape, in such a manner that an approximately semicircular transverse section of the belt member 344 is orthogonal to the underside surface and the anterior surface of the base board 350 under the above interdigitation state.

Thus, the plane overlapping on the entire loop of the coil element composed of the partial coils 374a and 374b and the plane overlapping on the entire loop of the coil element 380a or the coil element 380b are orthogonalized to each other, and their mutual coupling scarcely occurs.

Similarly, the connector 356a on the base board 350 is shaped so as to interdigitate the side of one end including the connector 386a of the belt member 346. The connector 356b on the base board 350 is shaped so as to interdigitate the side of the opposite end including the connector 386b of the belt member 346.

When both ends of the belt member 346 are interdigitated to the connectors 356a and 356b, both ends of each of the partial coils 376a and 376b are connected with each other via electrode and the like (not shown) in the connectors 356a, 356b, 386a and 386b, and thereby the partial coils 376a and 376b become a loop coil element.

In the way similar to the aforementioned manner, the partial coils 376a and 376b are disposed, so that the plane overlapping on the extending region of the conductive wire of the partial coils 376a and 376b is orthogonal to the underside surface and the anterior surface of the base board 350 under the state in which both ends of the belt member 346 are interdigitated to the base board 350.

In order to achieve this, each part is configured as a stereoscopic shape, in such a manner that an approximately semicircular transverse section of the belt member 346 is orthogonal to the underside surface and the anterior surface of the base board 350 under the above interdigitation state.

Thus, the plane overlapping on the entire loop of the coil element composed of the partial coils 376a and 376b and the plane overlapping on the entire loop of the coil element 380c or the coil element 380d are orthogonalized to each other, and their mutual coupling scarcely occurs.

FIG. 30 is a schematic planimetric diagram showing an example of the mounting state of the RF coil device 90G, under the pose in which the arms of the object P are put down. As an example of the mounting method, the belt members 344 and 346 are combined to the base member 340 so as to overlay both shoulders of the object P, under the state in which the base member 340 is arranged near the back of the shoulders of the object P after dismounting the belt members 344 and 346.

As an alternative mounting method, the RF coil device 90G may be mounted (lifted) onto the shoulders like a backpack. That is, the belt members 344 and 346 may be overlaid on the respective shoulders of the object P, under the state in which the belt members 344 and 346 are combined to the base member 340. Then, the side of the anterior surface of the object P may be covered with the overlay members 364 and 366. Note that, in order for the mounting state to be understandable, FIG. 30 shows the state in which one of the two overlay members (364) is not overlaid on the side of the anterior surface of the object P.

FIG. 31 is a schematic planimetric diagram showing an example of the mounting state of the RF coil device 90G, under the pose in which the arms of the object P are raised. In order to change the mounting state from the pose with the arms down shown in FIG. 30 to the pose with the arms raised shown in FIG. 31, the method may be, for example, as follows. That is, after dismounting the belt members 344 and 346, the belt members 344 and 346 may be interdigitated to the base board 350 so as to let both arms pass through the airspace between the base board 350 and the belt member 344 or 346. Then, overlay members 364 and 366 are overlaid on the side of the anterior surface of the object P. Here, the overlay members 364 and 366 don't restrict the motion of the arms of the object P, because they are flexible.

Note that, under the mounting state with the arms down shown in FIG. 30, each arm of the object P is not inserted into the airspace between the base board 350 and the belt member 344 or 346. However, the arm(s) of the object P may be inserted into this airspace.

As just described, the effects similar to the third embodiment can be obtained in the sixth embodiment.

Additionally, in the mounting state, the four coil elements 370a, 370b, 372a and 372b are closely-attached to the neighborhoods of both shoulders of the object P, because the two overlay members 364 and 366 are located at the side of the anterior surface of the object P. Additionally, the four coil elements 380a, 380b, 380c and 380d are closely-attached to the side of the back of both shoulders of the object P. Moreover, the two coil elements are formed by the partial coils 374a, 374b, 376a and 376b, so as to form loops on the plane orthogonal to these coil elements. Therefore, wide and satisfactory coil sensitivity can be obtained in the side of the anterior surface and the side of the back of an object. Moreover, one RF coil device can meet imaging of both shoulders.

Note that, though an example in which the overlay members 364 and 366 are arranged at both sides of the base board 350 so as to face each other has been explained in the sixth embodiment, this is only an example. The overlay members may be disposed at the side of the connectors 354a and 356a (the side of the head of an object in its mounting state), like the RF coil device 90H shown in FIG. 32 as a perspective view.

Figure 32:
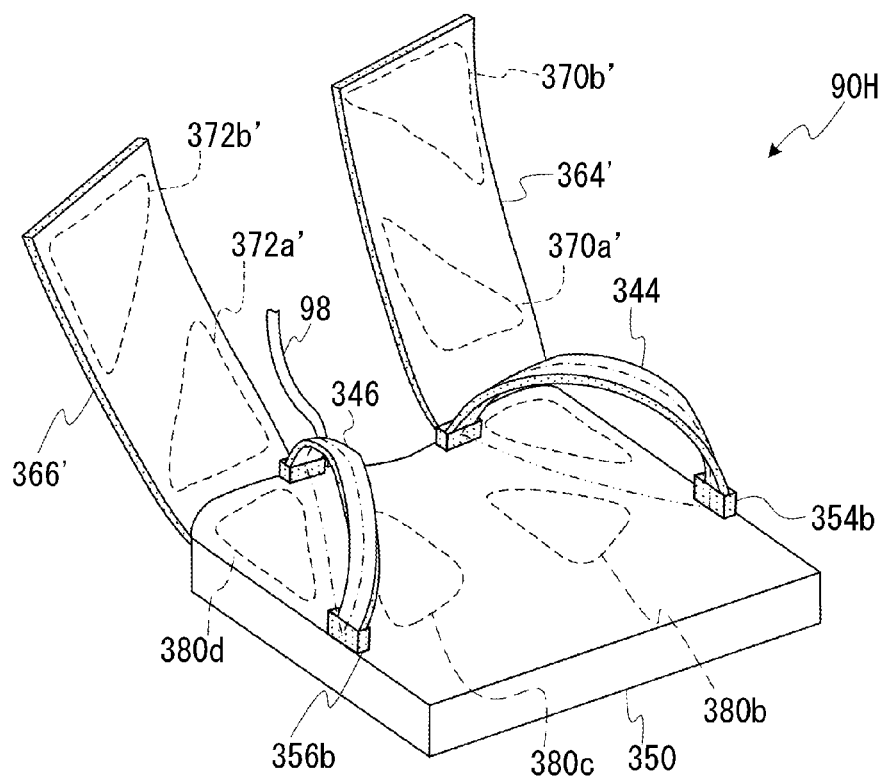
FIG. 32 is a schematic oblique perspective figure showing outline structure of an example of changed positions of two overlay members, as a supplementary embodiment of the RF coil device of the sixth embodiment.

The RF coil device 90H shown in FIG. 32 has the same structure as the aforementioned RF coil device 90G except its arrangement of overlay members 364' and 366'.

Inside the overlay member 364', coil elements 370a' and 370b' are disposed. Inside the overlay member 366', coil elements 372a' and 372b' are disposed. The same mounting method as the aforementioned RF coil device 90G is capable in this case, and the overlay members 364' are 366' can be overlaid on the shoulders of an object from above.

Additionally, as to the base board 350, it may have a stretchable structure in the shoulder-width direction so as to meet objects with different width between both shoulders (the base board 350 may composed so that the width between the overlay member 364 and overlay member 366 in FIG. 29 is stretchable).

The Seventh Embodiment

Figure 33:
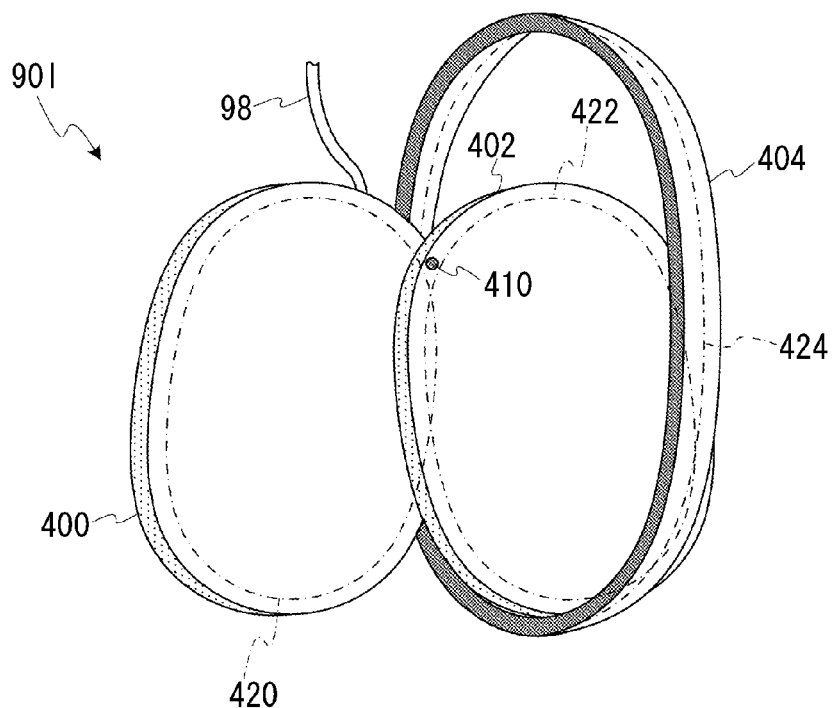
FIG. 33 is a schematic oblique perspective figure showing outline structure of the RF coil device of the seventh embodiment.

FIG. 33 is a schematic oblique perspective figure showing outline structure of the RF coil device 90I of the seventh embodiment. As shown in FIG. 33, the RF coil device 90I is composed by connecting a first base member 400 and a second base member 402, in such a manner that the first base member 400 and the second base member 402 can rotate (pivot) around a predetermined point of a belt member 404 by a rotational axis structure 410.

The first base member 400, the second base member 402, the belt member 404, and the rotational axis structure 410 are made of an undeformable material such as the FRP.

The first base member 400 and the second base member 402 are composed in the form of a flat plate consisting of both elliptical surfaces and a side surface. The first base member 400 and the second base member 402 are mutually equal in dimension and shape.

The belt member 404 has a shape obtained by circularly connecting both ends of a zonal plate. The first base member 400 and the second base member 402 are rotatably fixed so as to keep their frontal surfaces (and underside surfaces) in parallel with each other. A loop coil element 420 is planarly disposed (emplaced) inside the first base member 400, and a loop coil element 422 is planarly disposed (emplaced) inside the second base member 402.

As shown in FIG. 33, under the state in which the first base member 400 and the second base member 402 are rotatably connected (coupled) to each other, the coil elements 420 and 422 are arranged so as to partially overlap each other if they are planarly looked at. This is for the sake of obtaining a decoupling effect like in the aforementioned embodiments.

Additionally, inside the belt member 404, a circular coil element 424 is disposed (emplaced) along the extending plane of the belt member 404.

Thus, the plane overlapping on the entire loop of the coil element 424 and the plane overlapping on the entire loop of the coil element 420 are orthogonalized to each other, and the coupling effect between the coil elements 420 and 424 scarcely occurs.

Similarly, the plane overlapping on the entire loop of the coil element 424 and the plane overlapping on the entire loop of the coil element 422 are orthogonalized to each other, and the coupling effect between the coil elements 422 and 424 scarcely occurs.

Figure 34:
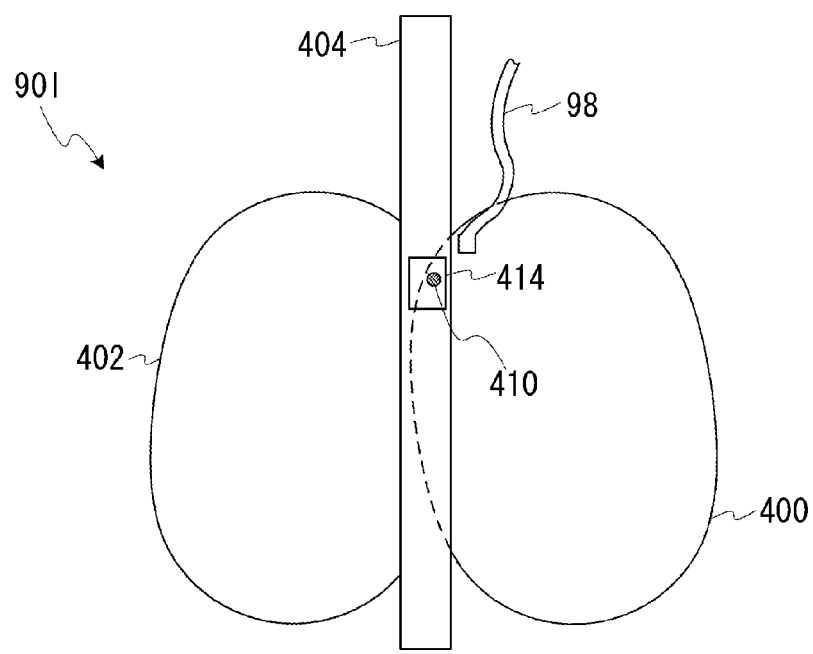
FIG. 34 is a schematic planimetric diagram of the RF coil device of the seventh embodiment, viewing from the side opposite to FIG. 33 (from the underside surface)

FIG. 34 is a schematic planimetric diagram of the RF coil device 90I viewing from the side opposite to FIG. 33 (from the underside surface).

As shown in FIG. 34, the cable 98 is exposed from the side of the underside surface of the first base member 400. The coil elements 420, 422 and 424 are electrically connected to individual hard-wirings inside the cable 98 by a circuit (not shown) inside the first base member 400, the second base member 402 and the rotational axis structure 410, respectively.

The rotational axis structure 410 includes a cylindrical rotational axis (not shown) passing through the first base member 400 and the second base member 402, and this rotational axis is fixed to one place of the belt member 404 with a fixing member 414.

Figure 35:
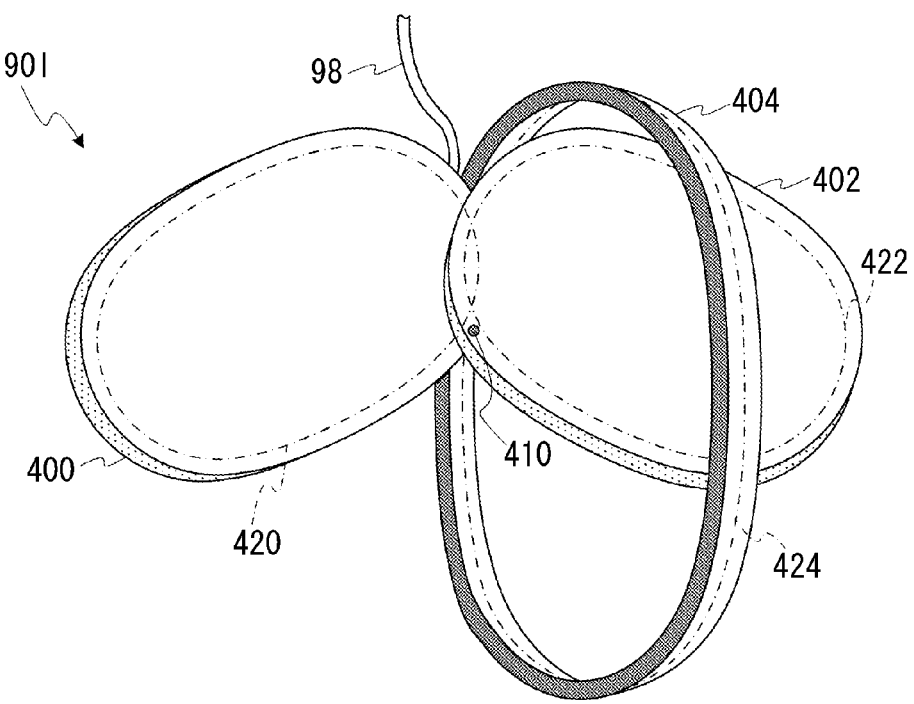
FIG. 35 is a schematic oblique perspective figure showing an overview of the RF coil device of the seventh embodiment, when the first base member and the second base member are spread out by rotation.

FIG. 35 is a schematic oblique perspective figure of the RF coil device 90I when the first base member 400 and the second base member 402 are spread out by rotation. As shown in FIG. 33 to FIG. 35, the first base member 400 and the second base member 402 are connected to each other, in such a manner that the first base member 400 and the second base member can rotate around the aforementioned rotational axis within the same (unaltered) plane by the rotational axis structure 410.

Figure 36:
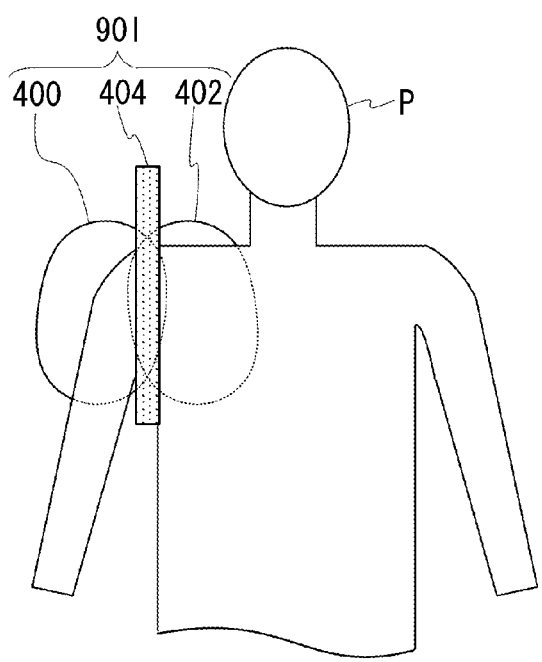
FIG. 36 is a schematic planimetric diagram showing an example of the mounting state of the RF coil device of the seventh embodiment, under the state in which the arm of an object is put down.

FIG. 36 is a schematic planimetric diagram showing an example of the mounting state of the RF coil device 90I, under the state in which the arm of the object P is put down. As an example of its mounting method, for example, the arm of the object are inserted into (the aperture of) the belt member 404, in such a manner that the first base member 400 and the second base member 402 are arranged on the back side of the object P.

Figure 37:
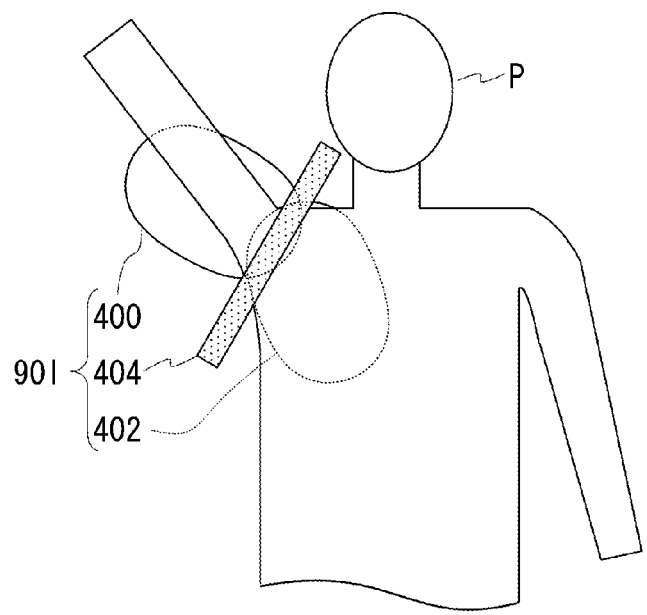
FIG. 37 is a schematic planimetric diagram showing an example of the mounting state of the RF coil device of the seventh embodiment, under the state in which the arm of an object is raised.

FIG. 37 is a schematic planimetric diagram showing an example of the mounting state of the RF coil device 90I, under the state in which the arm of the object P is raised. Because the first base member 400 and the second base member 402 are arranged on the back side of the object P and they are in the form of flat plates, they don't restrict the motion of raising and lowering the arm by the object P. Thus, only "the belt member 404 whose width is appropriate so as not to restrict the motion of the arm" is winded around the arm of the object P. Therefore, the RF coil device 90I can be effortlessly set, under both poses in which the arm is raised and lowered.

As just described, the effects similar to the fourth embodiment can be obtained in the seventh embodiment. Moreover, in the seventh embodiment, it is able to rotate the first base member 400 and the second base member 402 so that both are arranged directly beneath the root of the arm and the shoulder of the object P, when the object P raises or puts down the arm (see FIG. 36 and FIG. 37). Thereby, the coil sensitivity region can be appropriately changed according to the position of the arm of the object P.

The Eighth Embodiment

Figure 38:
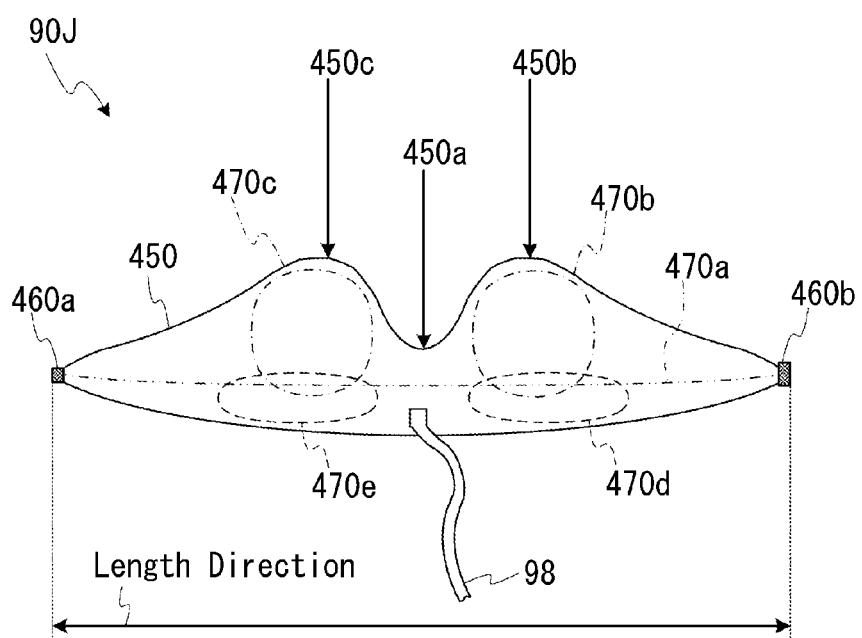
FIG. 38 is a schematic planimetric diagram showing an RF coil device of the eighth embodiment in an unfolded state.
Figure 39:
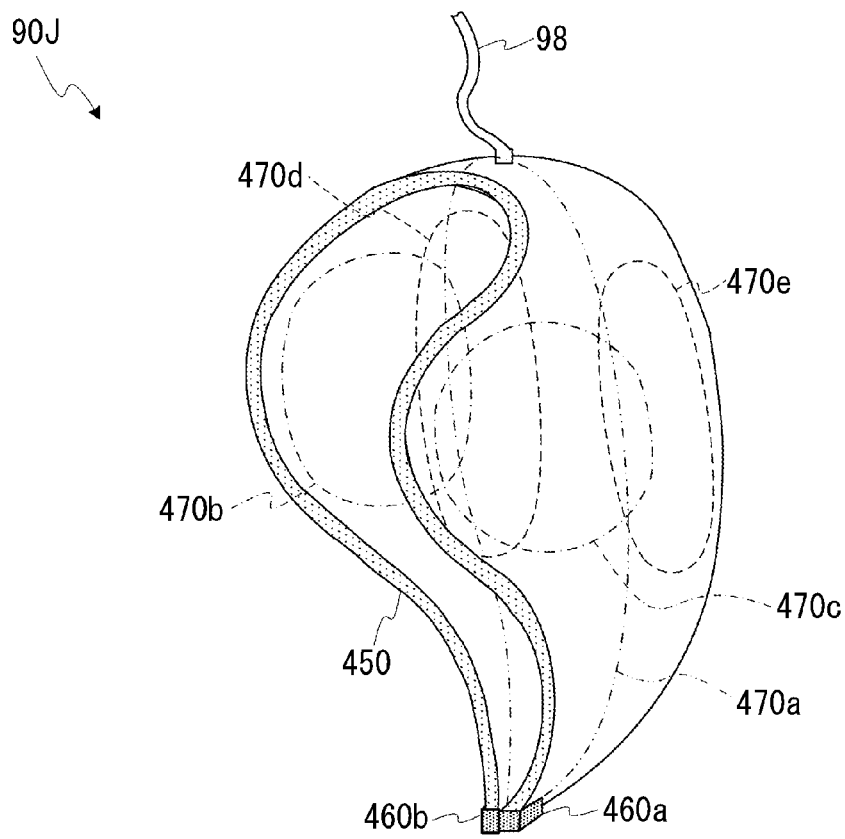
FIG. 39 is a schematic oblique drawing of the RF coil device of the eighth embodiment folded with both ends connected to each other.

FIG. 38 is a schematic planimetric diagram showing an RF coil device 90J of the eighth embodiment in an unfolded state. FIG. 39 is a schematic oblique drawing of the RF coil device 90J folded with both ends connected to each other. As shown in FIG. 38, the RF coil device 90J has a band member 450, a connector 460a disposed (emplaced) at one end of the band member 450, and a connector 460b disposed at the opposite end of the band member 450.

In order for the band member 450 to wrap around the base of the arm of the object in the mounting state, the band member 450 is made of a flexible material such as FPC and has an approximately band-like shape. The band member 450 narrows at its central part 450a in the length direction (indicated by an arrow in FIG. 38). The recessed (concave) central part 450a is intended to accommodate the arm raised in the mounting state, thereby facilitating mounting of the RF coil device 90J with the arm of the object raised.

The band member 450 ensures sensitivity regions of coil elements by covering a shoulder region of the object and, to this end, is widened on the ambilateral sides of the central part 450a to have protrusion parts 450b and 450c.

The band member 450 is tapered from the protrusion part 450c toward its one end (at which the connector 460a is disposed), and is tapered from the protrusion part 450b toward the other end (at which the connector 460b is disposed). This tapering facilitates an object to lower the arm, because both ends of the band member 450 are located under the axilla of the object in the mounting state.

The cable 98 is provided on the band member 450 in its central part. In the band member 450, a coil element 470a is provided and extends from one end to the opposite end.

As shown in FIG. 39, the connector 460b is configured to interdigitate the one end of the band member 450 including the connector 460a. In the interdigitation state, both ends of the coil element 470a are electrically connected to each other by electrodes or the like (not shown) in the connectors 460a and 460b, and the coil element 470a serves as a loop coil element.

As shown in FIG. 38, when the RF coil device 90J is divided in the length direction, the part on the one end side (the side of the connector 460a) and the part on the other end side (the side of the connector 460b) are substantially symmetric (except the difference in shape between the connectors 460a and 460b, one being of the male type, and the other being of the female type).

Specifically, as shown in FIG. 38, a loop-shaped (elliptic) coil element 470b is provided inside the band member 450 so as to cover a region including the protrusion part 450b across the line of the coil element 470a. Similarly, inside the band member 450, a loop-shaped (elliptic) coil element 470c is provided inside the band member 450 so as to cover a region including the protrusion part 450c across the line of the coil element 470a.

Inside the band member 450, a loop-shaped (elliptic) coil element 470d is also provided on the side opposite to the coil element 470b, so that the line of the coil element 470a passes approximately the center of their overlapping region.

Similarly, inside the band member 450, a loop-shaped (elliptic) coil element 470e is provided in the band member 450 on the side opposite to the coil element 470c, so that the line of the coil element 470a passes approximately the center of their overlapping region.

For the sake of obtaining a decoupling effect, the coil elements 470b and 470d are arranged so as to partially overlap each other in a plan view. Similarly, the coil elements 470c and 470e are arranged so as to overlap with each other in a plan view. The coil elements 470a to 470e are respectively connected to separate wires in the cable 98 by a circuit (not shown) in the band member 450.

Figure 40:
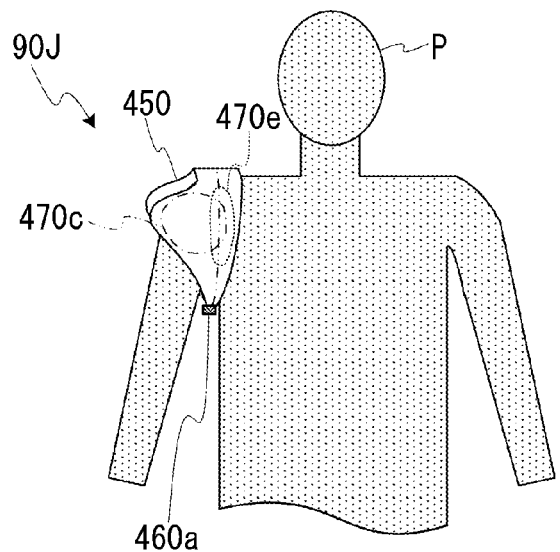
FIG. 40 is a schematic planimetric diagram showing an example of the mounting state of the RF coil device of the eighth embodiment on an object with the arm lowered, in such a manner that protrusion parts of its band member are located on the arm side.

FIG. 40 is a schematic planimetric diagram showing an example of the mounting state of the RF coil device 90J on the object P with the arm lowered, in such a manner that the protrusion parts 450b and 450c of the band member 450 are located on the arm side.

The RF coil device 90J can be mounted on the shoulder by placing the band member 450 on the shoulder of the object P and then making the connectors 460a and 460b interdigitate each other under the axilla of the object P.

Alternatively, the connectors 460a and 460b can be made to interdigitate each other in advance, and then, the object P can put the arm into the band member 450.

Figure 41:
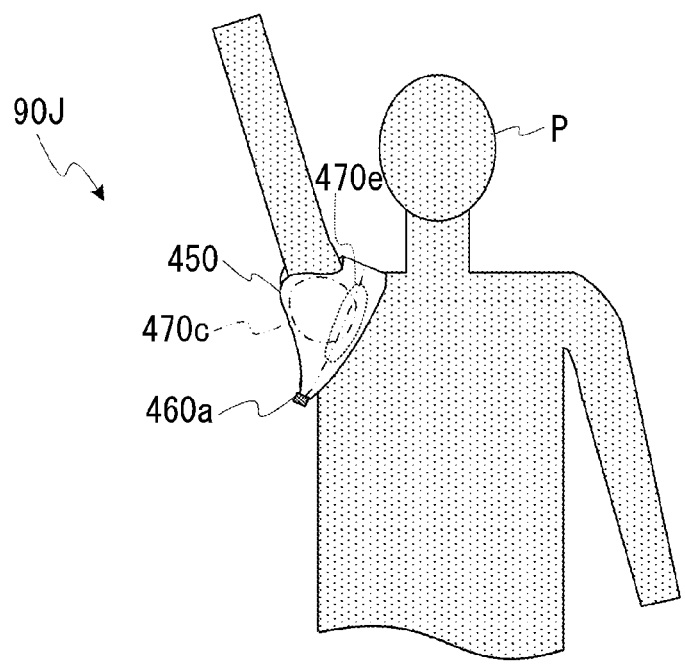
FIG. 41 is a schematic planimetric diagram showing an example of the mounting state of the RF coil device of the eighth embodiment, under the state in which the arm of an object is raised from the position shown in FIG. 40.

FIG. 41 is a schematic planimetric diagram showing an example of the mounting state of the RF coil device 90J on the object P with the arm raised from the position shown in FIG. 40. As can be seen from the FIG. 40 and FIG. 41, the central part 450a of the band member 450 is recessed. Since the arm raised can be accommodated in the recess (dent), the object P can easily wear the RF coil device 90J whether the arm is raised or lowered.

In the mounting state described above, the anterior surface of the shoulder is covered with the sensitivity regions of the coil elements 470c and 470e (see FIGS. 40 and 41), and the posterior surface of the shoulder is covered with the sensitivity regions of the coil elements 470b and 470d (not shown). The sensitivity region of the coil element 470a extends in the direction perpendicular to the sensitivity regions of the four coil elements 470b, 470c, 470d and 470e. This arrangement of the five coil elements 470a to 470e can ensure satisfactory coil sensitivity.

Figure 42:
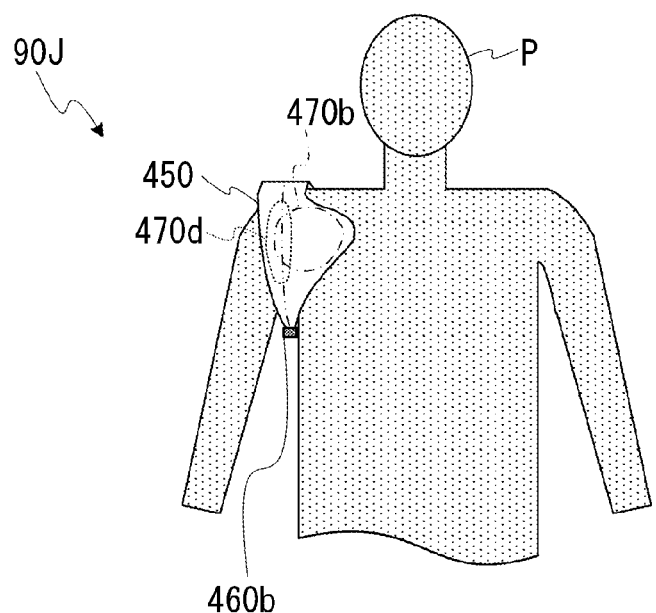
FIG. 42 is a schematic planimetric diagram showing an example of the mounting state of the RF coil device of the eighth embodiment on an object with the arm lowered, in such a manner that the protrusion parts of the band member are located on the chest side.

FIG. 42 is a schematic planimetric diagram showing an example of the mounting state of the RF coil device 90J on the object P with the arm lowered, in such a manner that the protrusion parts 450b and 450c of the band member 450 are located on the chest side.

Figure 43:
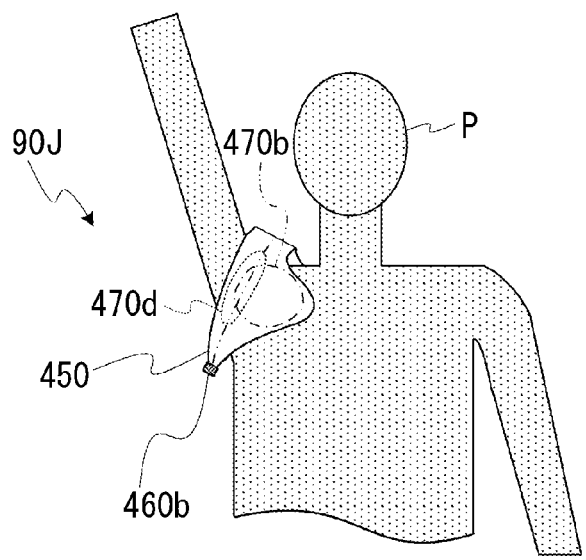
FIG. 43 is a schematic planimetric diagram showing an example of the mounting state of the RF coil device of the eighth embodiment, under the state in which the arm of an object is raised from the position shown in FIG. 42.

FIG. 43 is a schematic planimetric diagram showing an example of the mounting state of the RF coil device 90J on the object P with the arm raised from the position shown in FIG. 42.

The band member 450 is simply wrapped around the arm of the object P and is flexible. Therefore, as shown in FIG. 42 and FIG. 43, when the protrusion parts 450b and 450c of the band member 450 are located on the chest side of the object P, the RF coil device 90J can also be easily mounted whether the arm is raised or lowered. In the mounting state shown in FIGS. 42 and 43, the five coil elements 470a to 470e can ensure satisfactory coil sensitivity as in the mounting state shown in FIG. 40 and FIG. 41.

Although the connectors 460a and 460b are located under the axilla of the object P in the mounting state described above with reference to FIGS. 40 to 43, the RF coil device 90J can also be mounted with the connectors 460a and 460b located on the top of the shoulder of the object P.

Figure 44:
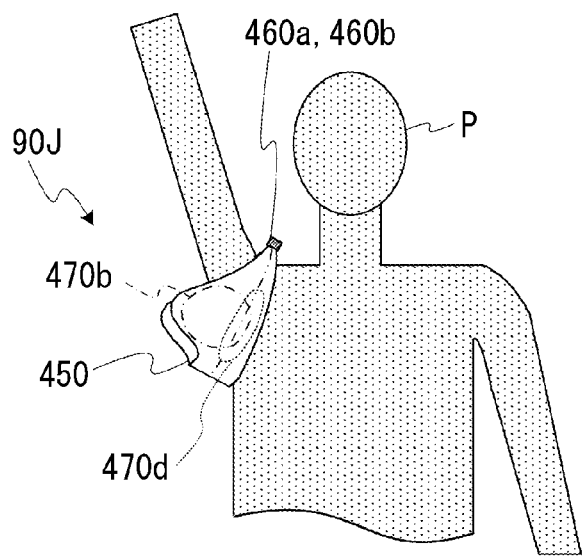
FIG. 44 is a schematic planimetric diagram showing an example of the mounting state of the RF coil device of the eighth embodiment on an object with the arm raised, in such a manner that its connectors are located on the top of the shoulder and the protrusion parts are located on the outer side of the object.
Figure 45:
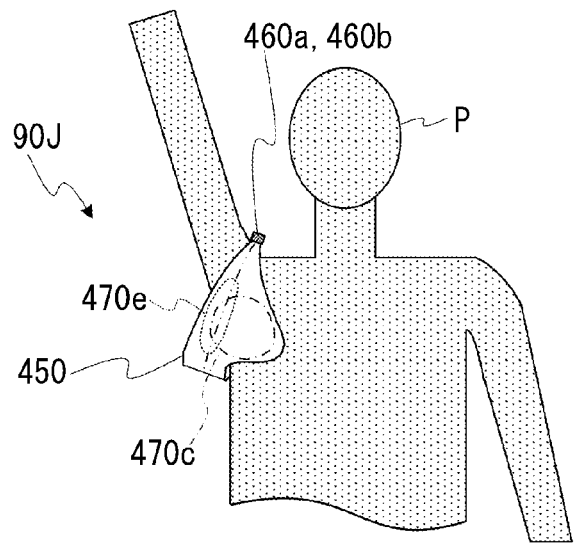
FIG. 45 is a schematic planimetric diagram showing an example of the mounting state of the RF coil device of the eighth embodiment on an object with the arm raised, in such a manner that the connectors are located on the top of the shoulder and the protrusion parts are located on the chest side.

FIG. 44 and FIG. 45 are schematic planimetric diagrams showing examples of the mounting state of the RF coil device 90J on the object P with the arm raised, in such a manner that the connectors 460a and 460b are located on the top of the shoulder. In the mounting state shown in FIG. 44, the protrusion parts 450b and 450c are located on the outer side of the object P. In the mounting state shown in FIG. 45, the protrusion parts 450b and 450c are located on the chest side of the object P.

Figure 46:
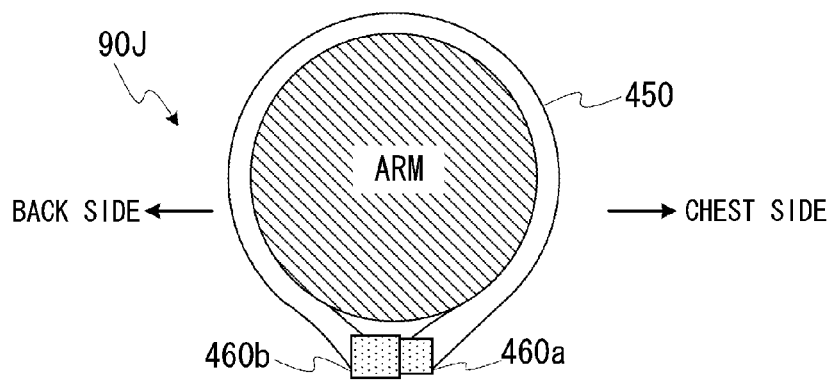
FIG. 46 is a schematic sagittal cross-sectional diagram, when the RF coil device of the eighth embodiment is set on an object with a thick arm in the manner shown in FIG. 40.
Figure 47:
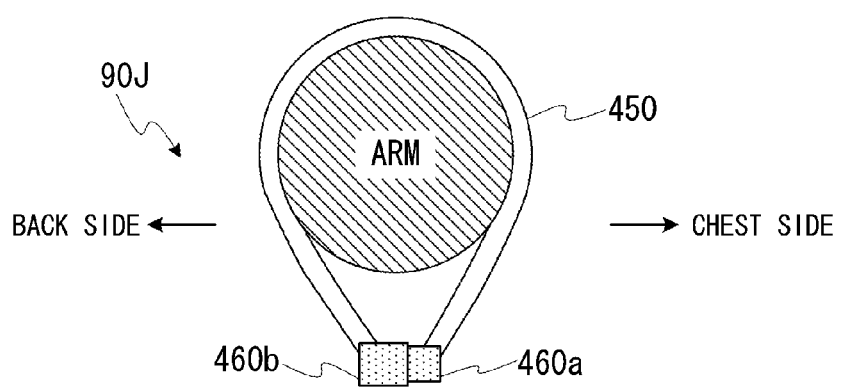
FIG. 47 is a schematic sagittal cross-sectional diagram, when the RF coil device of the eighth embodiment is set on an object with a slender arm in the manner shown in FIG. 40.

FIG. 46 and FIG. 47 are schematic cross-sectional diagrams showing sagittal cross-sections of the shoulder joint part in the mounting state shown in FIG. 40 in the human body coordinate system.

FIG. 46 shows the mounting state in the case where the arm of the object is big, and FIG. 47 shows the mounting state in the case where the arm of the object is slender.

The sagittal cross-sections described above are taken along the Y-Z plane of the following human body coordinate system. That is, the Y axis direction of the human body coordinate system corresponds to the anteroposterior direction of the body of the object P, on the assumption that the front side of the object P is the anterior side and the back side of the object P is the posterior side. The Z axis direction of the human body coordinate system corresponds to the vertical direction, on the assumption that the head is on the upper side and the legs are on the lower side in the direction of extension of the back bone.

In the case where the arm of the object is big, the gap between the band member 450 and the arm of the object is narrow as shown in FIG. 46. In the case where the arm of the object P is slender, the gap between the band member 450 and the arm of the object is wide as shown in FIG. 47.

As can be seen form FIG. 46 and FIG. 47, the RF coil device 90J can be mounted whether the arm of the object is big or slender, since the band member 450 is flexible. As described above, in the eighth embodiment, the same advantages as those in the fifth embodiment are provided.

Ninth Embodiment

Figure 48:
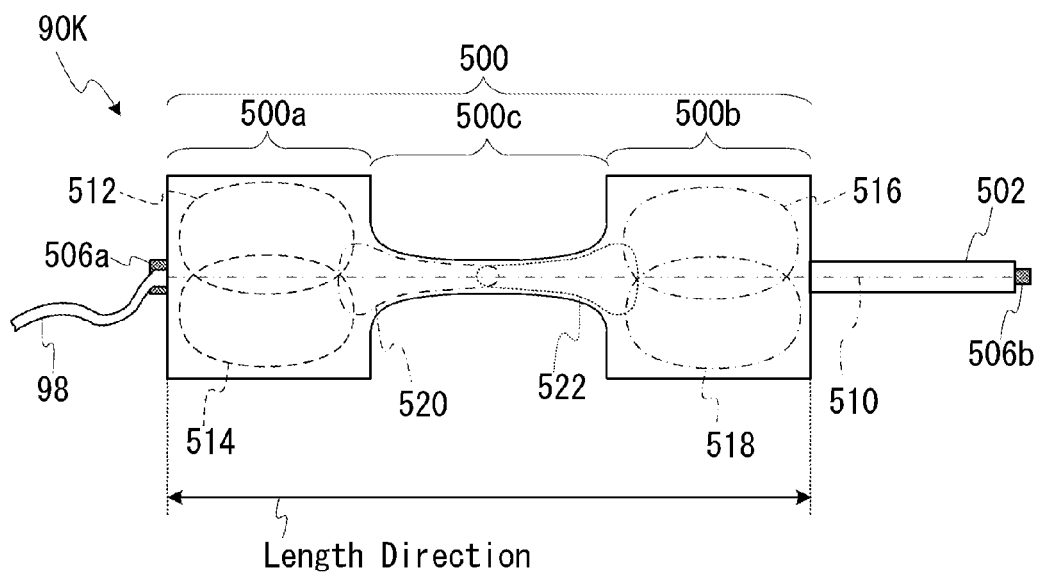
FIG. 48 is a schematic planimetric diagram showing an RF coil device of the ninth embodiment in an unfolded state.

FIG. 48 is a schematic planimetric diagram showing the RF coil device 90K of the ninth embodiment in an unfolded state.

Figure 49:
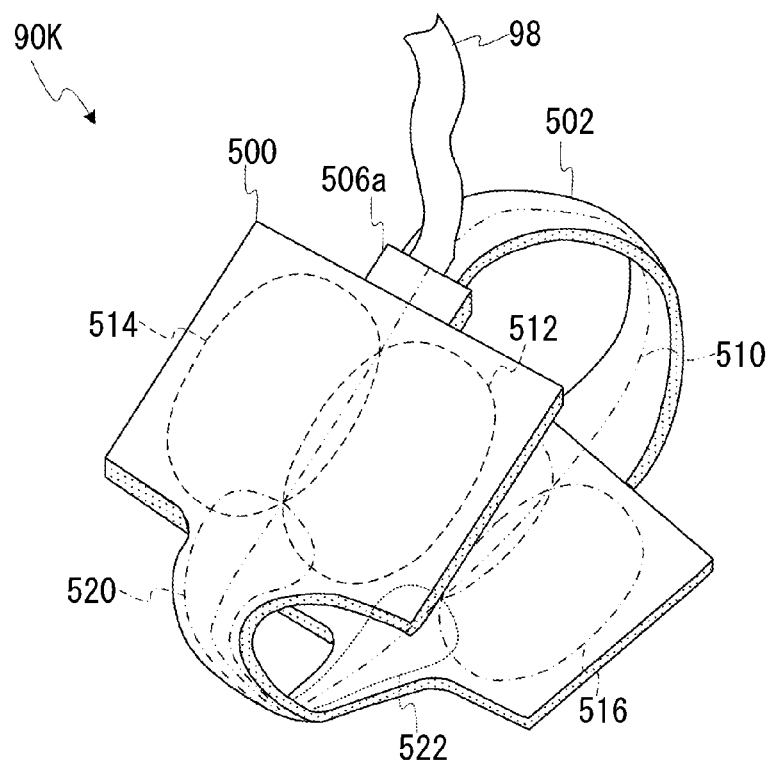
FIG. 49 is a schematic oblique drawing of the RF coil device of the ninth embodiment, under the state in which both ends thereof are connected to each other.

FIG. 49 is a schematic oblique drawing of the RF coil device 90K with both ends connected to each other. As shown in FIG. 48, the RF coil device 90K has a cover member 500 and a belt member 502.

The cover member 500 is connected to one end of the belt member 502 at one end. A connector 506a is disposed (emplaced) at the opposite end of the cover member 500, and a connector 506b is disposed at the opposite end of the belt member 502.

In the mounting state, the connectors 506a and 506b are connected (coupled) to each other, in such a manner that the cover member 500 and the belt member 502 cooperate to wrap around the root (base) of the arm of the object. To this end, the cover member 500 and the belt member 502 are made of a flexible material such as FPC.

The cover member 500 is made approximately in the form of a band, and is sectioned into three parts in the length direction (indicated by an arrow in FIG. 48). Specifically, the cover member 500 is sectioned into an overlay part 500a located at the one end, an overlay part 500b located at the opposite end, and a band part 500c that connects the overlay parts 500a and 500b each other.

One of the overlay parts 500a and 500b is to come into contact with the anterior surface of the shoulder of the object, and the other is to come into contact with the posterior surface. In order to ensure the sensitivity regions of the coils in this contact state by covering the shoulder region of the object, the overlay parts 500a and 500b are wider than the band part 500c. Another reason why the band part 500c is narrower than the overlay parts 500a and 500b is to ensure that the object can effortlessly hold the cover member 500 in the axilla in this contact state.

On the side of the opposite end of the cover member 500, the cable 98 is exposed from the position near the connector 506a. In addition, a coil element 510 is disposed so as to extend from the opposite end to the one end of the belt member 502 and from the one end to the opposite end of the cover member 500. This is so that the coil element 510 forms a straight line, when the cover member 500 and the belt member 502 are unfolded and laid flat.

The connector 506a is configured to interdigitate the opposite end of the belt member 502 including the connector 506b. In the interdigitation state, both ends of the coil element 510 are electrically connected to each other by electrodes or the like (not shown) in the connectors 506a and 506b, and the coil element 510 serves as a loop coil element.

When the RF coil device 90K is equally divided into upper and lower pats along the line of the coil element 510 shown in FIG. 48, the RF coil device 90K is symmetric.

Specifically, in the overlay part 500a of the cover member 500, two loop-shaped coil elements 512 and 514 are disposed symmetrically so that the line of the coil element 510 becomes their line-symmetric axis. For the sake of obtaining a decoupling effect, the coil elements 512 and 514 are arranged so as to partially overlap each other in a plan view.

Similarly, in the overlay part 500b of the cover member 500, two loop-shaped coil elements 516 and 518 are disposed symmetrically so that the line of the coil element 510 becomes their line-symmetric axis. For the sake of obtaining a decoupling effect, the coil elements 516 and 518 are arranged so as to partially overlap each other in a plan view.

As shown in FIG. 48, in the cover member 500, a coil element 520 is emplaced so as to cover substantially a left half of the band part 500c and a right part of the overlay part 500a, and a coil element 522 is emplaced so as to cover substantially a right half of the band part 500c and a left part of the overlay part 500b.

For the sake of obtaining a decoupling effect, the coil elements 520 and 522 are disposed so as to partially overlap each other in a plan view at the center of the band part 500c.

For the sake of obtaining a decoupling effect, the coil element 520 is also disposed so as to partially overlap on the coil elements 512 and 514 in a plan view.

For the sake of obtaining a decoupling effect, the coil element 522 is also disposed so as to partially overlap on the coil elements 516 and 518 in a plan view.

The coil elements 510, 512, 514, 516, 518, 520 and 522 are respectively connected to a separate wire in the cable 98 by a circuit (not shown) in the cover member 500.

Figure 50:
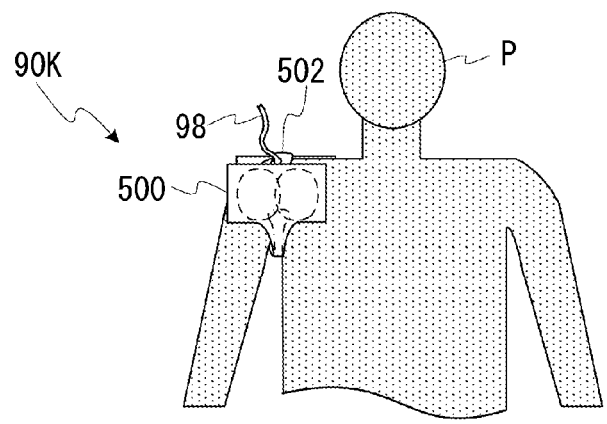
FIG. 50 is a schematic planimetric diagram showing an example of the mounting state of the RF coil device of the ninth embodiment mounted on an object with the arm lowered, in such a manner that a band part of its cover member is held in the axilla of the object.

FIG. 50 is a schematic planimetric diagram showing an example of the mounting state of the RF coil device 90K mounted on the object P with the arm lowered, in such a manner that the band part 500c of the cover member 500 held in the axilla of the object P.

For example, the RF coil device 90K can be mounted by placing the band part 500c under the axilla and the overlay parts 500a and 500b over the anterior surface and the posterior surface of the shoulder of the object P respectively and then making the connectors 506a and 506b interdigitate to each other. Alternatively, the connectors 506a and 506b can be made to interdigitate each other in advance, and then, the object P can put the arm into the RF coil device 90K.

Figure 51:
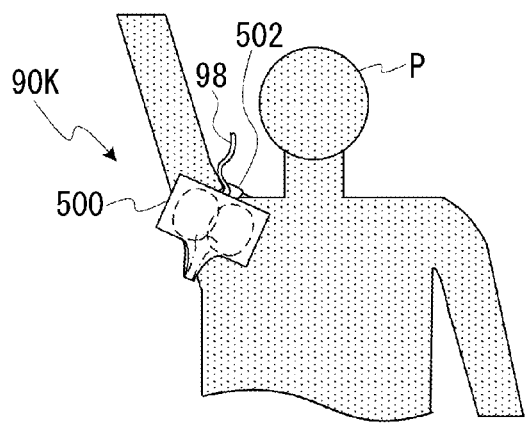
FIG. 51 is a schematic planimetric diagram showing an example of the mounting state of the RF coil device of the ninth embodiment, under the state in which the arm of the object is raised from the position shown in FIG. 50.

FIG. 51 is a schematic planimetric diagram showing an example of the mounting state of the RF coil device 90K mounted on the object P with the arm raised from the position shown in FIG. 50.

As can be seen from FIG. 50 and FIG. 51, though the anterior surface and the posterior surface of the shoulder of the object P are covered with the overlay parts 500a and 500b, the RF coil device 90K has no part that directly interferes with raising or lowering of the arm of the object P. In addition, since most parts of the RF coil device 90K (including the cover member 500 and the belt member 502) are flexible, the object P can easily raise or lower the arm even when the RF coil device 90J is mounted on the shoulder.

In the mounting state described above, the anterior surface and the posterior surface of the shoulder are covered with the sensitivity regions of the coil elements 512, 514 and 520 or the coil elements 516, 518 and 522 (see FIG. 48 and FIG. 49). The sensitivity region of the coil element 510 extends in the direction perpendicular to the sensitivity regions of the coil elements 512, 514, 516 and 518. This arrangement of the seven coil elements 510, 512, 514, 516, 518, 520 and 522 can ensure satisfactory coil sensitivity in the shoulder region.

Figure 52:
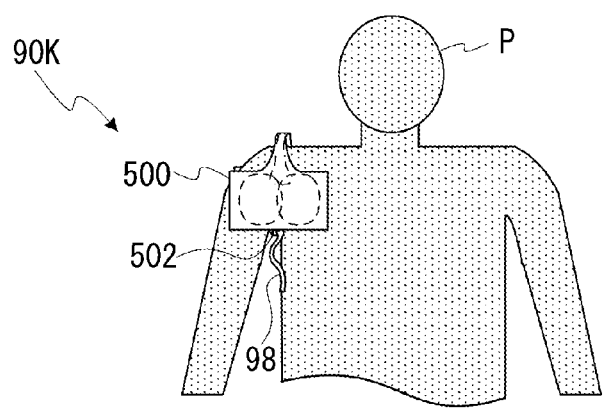
FIG. 52 is a schematic planimetric diagram showing an example of the mounting state of the RF coil device of the ninth embodiment on an object with the arm lowered, in such a manner that its belt member is held in the axilla of the object.

FIG. 52 is a schematic planimetric diagram showing an example of the mounting state of the RF coil device 90K on the object P with the arm lowered, in such a manner that the belt member 502 is held in the axilla of the object P.

Figure 53:
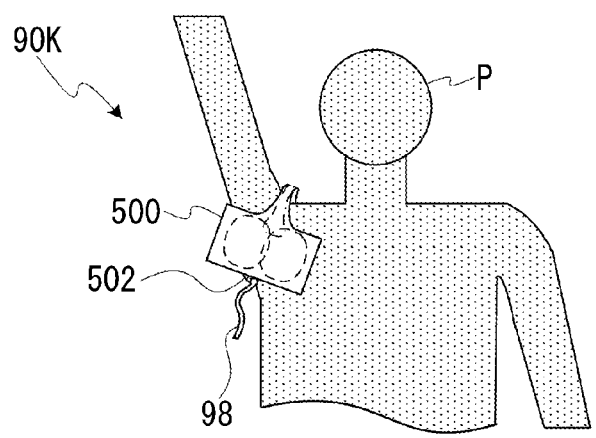
FIG. 53 is a schematic planimetric diagram showing an example of the mounting state of the RF coil device of the ninth embodiment, under the state in which the arm of the object is raised from the position shown in FIG. 52.

FIG. 53 is a schematic planimetric diagram showing an example of the mounting state of the RF coil device 90K on the object P with the arm raised from the position shown in FIG. 52.

In the mounting states shown in FIG. 52 and FIG. 53, as in the cases shown in FIG. 50 and FIG. 51, though the anterior surface and the posterior surface of the shoulder of the object P are covered with the overlay parts 500a and 500b, the RF coil device 90K has no part that directly interferes with raising or lowering of the arm of the object P.

Therefore, the object P can raise or lower the arm even when the RF coil device 90K is mounted on the shoulder. In the mounting states shown in FIG. 52 and FIG. 53, the seven coil elements 510, 512, 514, 516, 518, 520 and 522 can ensure satisfactory coil sensitivity in the shoulder region as in the cases shown in FIG. 50 and FIG. 51.

As described above, in the ninth embodiment, the same advantages as those in the fifth embodiment are provided.

Although the overlay parts 500a and 500b and the band part 500c form an integral cover member 500 in the embodiment described above, this is only an example. As an alternative, the cover member may be separable into a section including the overlay part 500a and a section including the overlay part 500b, as shown in FIG. 54.

Figure 54:
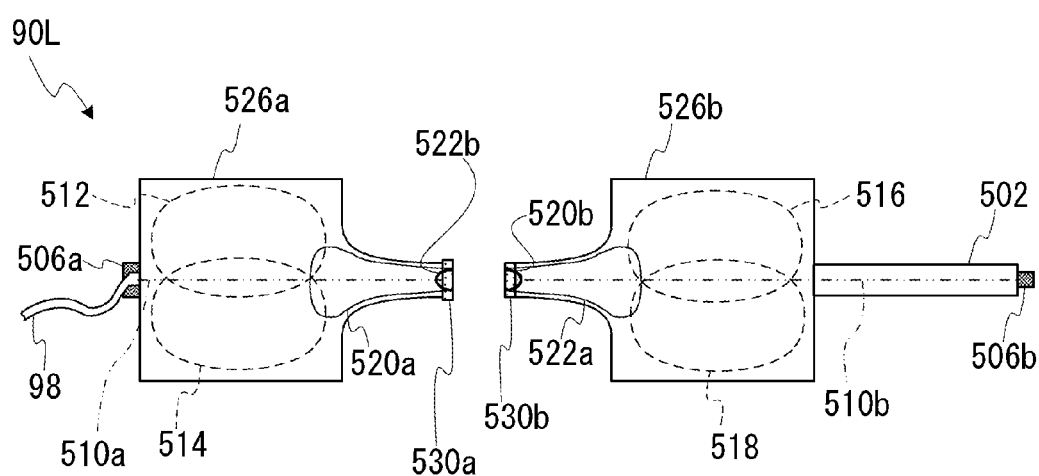
FIG. 54 is a schematic planimetric diagram showing a general configuration of a modification of the ninth embodiment.

FIG. 54 is a schematic planimetric diagram showing outline structure of a modification of the ninth embodiment. As shown in FIG. 54, an RF coil device 90L has the same structure as the RF coil device 90K described above except that the cover member 500 is replaced with a first cover member 526a and a second cover member 526b that can be detachably connected to each other. In the following, only the difference will be described.

Specifically, the first cover member 526a has a connector 530a disposed at one end thereof, and the second cover member 526b has a connector 530b disposed at one end thereof.

Inside the first cover member 526a, a partial coil 510a corresponding to a half of the coil element 510 of the RF coil device 90K described above is disposed. Inside the second cover member 526b, a partial coil 510b corresponding to the remaining half of the coil element 510 described above is disposed.

Inside the first cover member 526a, a partial coil 520a corresponding to a main part of the coil element 520 of the RF coil device 90K described above is disposed. Inside the second cover member 526b, a partial coil 522a corresponding to a main part of the coil element 522 of the RF coil device 90K described above is disposed.

Inside the first cover member 526a, a partial coil 522b corresponding to the remaining part of the coil element 522 described above is also disposed. Inside the second cover member 526b, a partial coil 520b corresponding to the remaining part of the coil element 520 described above is also disposed.

The connector 530a is configured to interdigitate the one end of the second cover member 526b including the connector 530b. In the interdigitation state, both ends of the partial coil 520a are connected to the corresponding ends of the partial coil 520b by electrodes or the like (not shown) in the connectors 530a and 530b, and the partial coils 520a and 520b serve as one loop-shaped coil element.

Similarly, in the interdigitation state, both ends of the partial coil 522a are connected to the corresponding ends of the partial coil 522b, and the partial coils 522a and 522b serve as one loop-shaped coil element.

In the interdigitation state, the partial coils 510a and 510b are also electrically connected to each other. The RF coil device 90L described above can also have the same advantages as the RF coil device 90K, since the entire shape and the arrangement of each coil element in the RF coil device 90L are the same as those of the RF coil device 90K in the interdigitation (connection) state.

Tenth Embodiment

Figure 55:
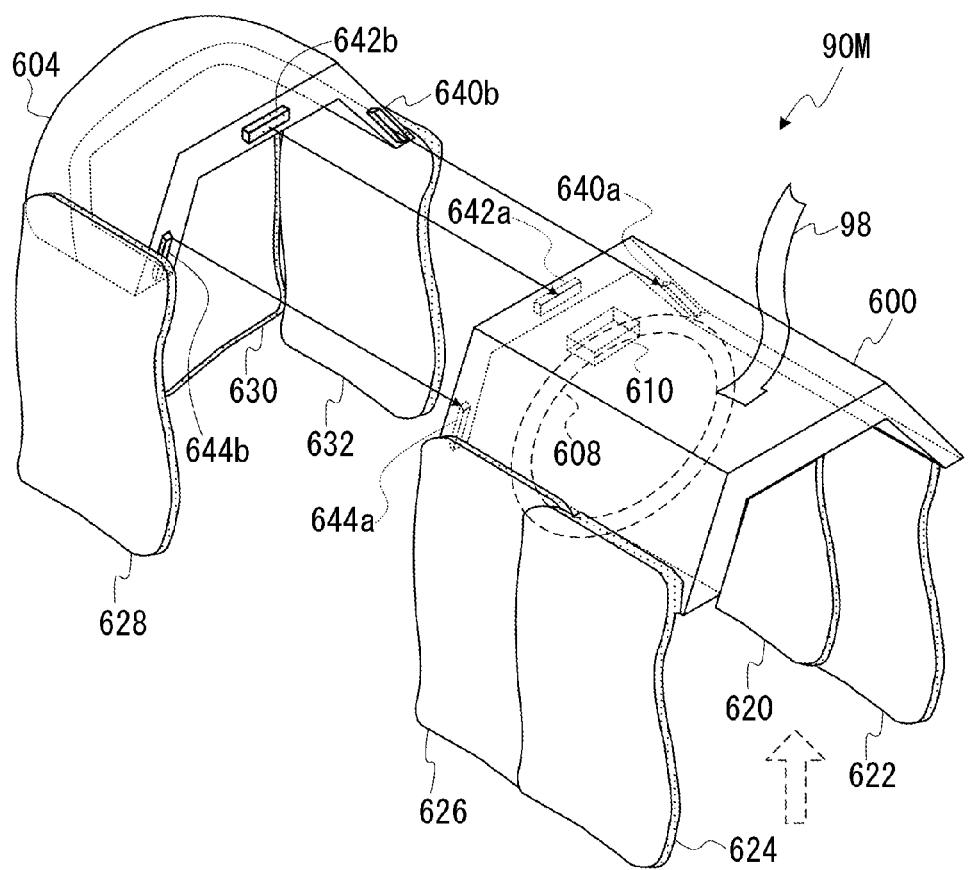
FIG. 55 is a schematic exploded perspective view of an RF coil device of the tenth embodiment.

FIG. 55 is a schematic exploded perspective view of an RF coil device 90M of the tenth embodiment. As shown in FIG. 55, the RF coil device 90M has a cover member 600 and an option member 604 connected (coupled) to each other. In FIG. 55, three solid line arrows indicate the directions in which connectors on the cover member 600 and connectors on the option member 604 are connected (interdigitated) to each other. Each of these solid line three arrows indicates the same direction.

Figure 56:
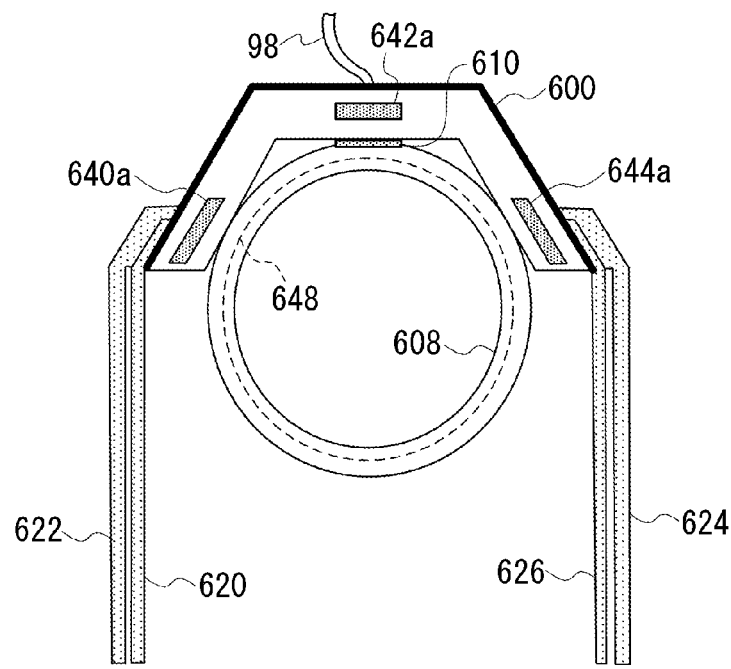
FIG. 56 is a schematic side view of its cover member of the RF coil device of the tenth embodiment, viewed in the direction indicated by the three solid line arrows in FIG. 55.

FIG. 56 is a schematic side view of the cover member 600 viewed in the direction indicated by the three solid line arrows in FIG. 55.

Figure 57:
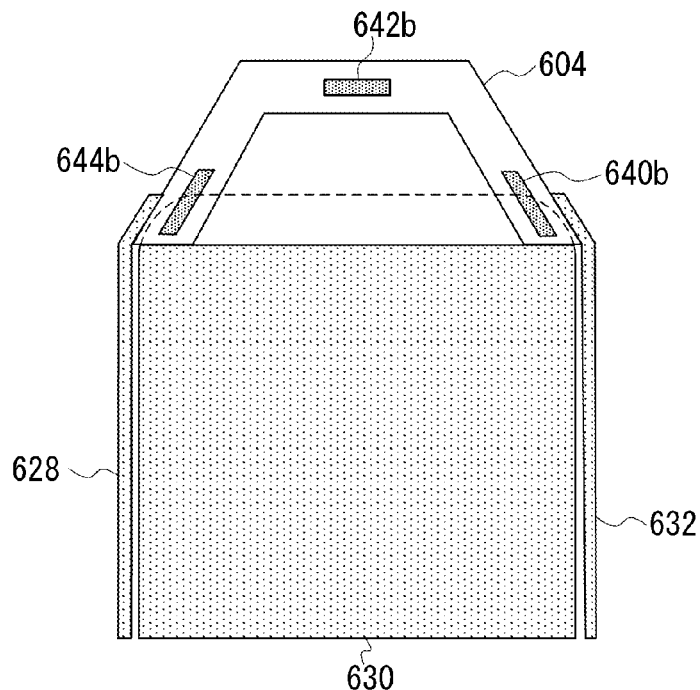
FIG. 57 is a schematic side view of its option member of the RF coil device of the tenth embodiment, viewed in the direction opposite to the direction indicated by the three solid line arrows in FIG. 55.

FIG. 57 is a schematic side view of the option member 604 viewed in the direction opposite to the direction indicated by the three solid line arrows in FIG. 55.

Figure 58:
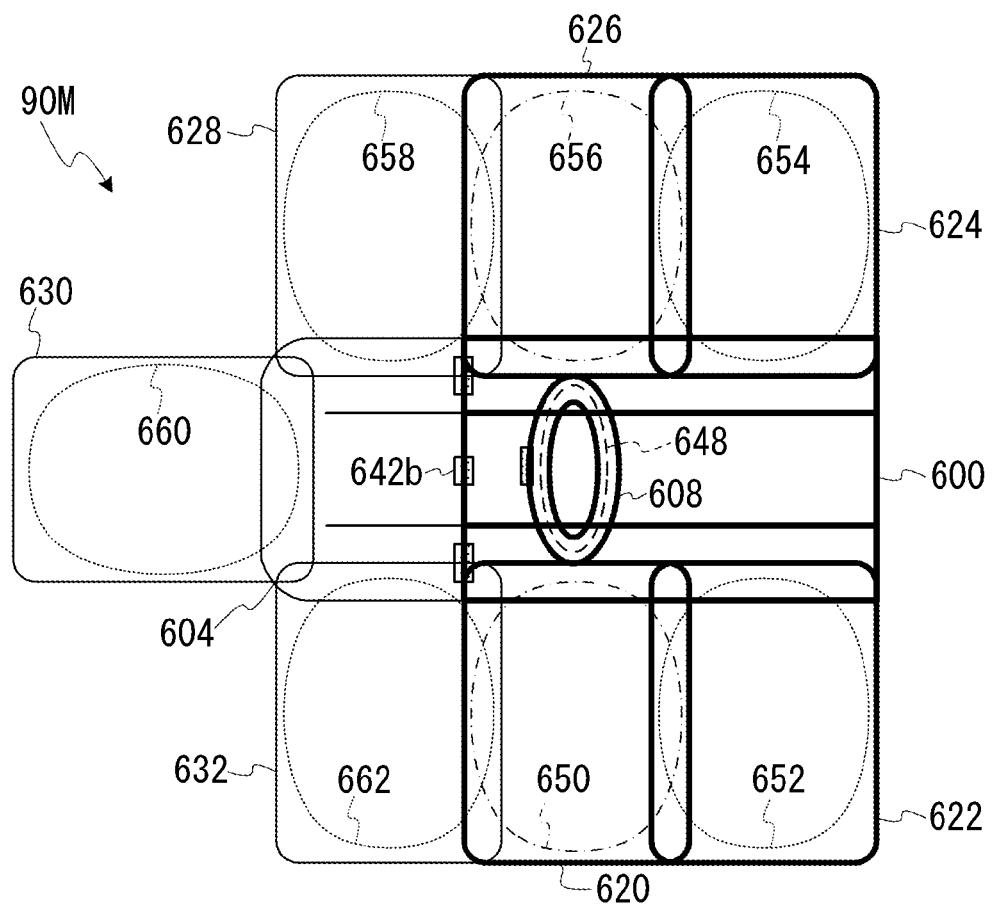
FIG. 58 is a schematic planimetric diagram showing an internal arrangement of coil elements, when the cover member and the option member of the RF coil device of the tenth embodiment are connected to each other.

FIG. 58 is a schematic planimetric diagram showing an arrangement of internal coil elements under the state in which the cover member 600 and the option member 604 are connected to each other, viewed in the direction indicated by a dashed line arrow in FIG. 55.

In FIG. 58, to make the arrangement of the coil elements easier to see, flap members 620, 622, 624, 626, 628, 630 and 632 are shown in developed view (in which they are shown as being laid flat), and only a ring member 608 and a coil element 648 in the ring member 608 are shown in perspective view.

In addition, in FIG. 58, to make discrimination easier, the cover member 600 and the elements fixed thereto are indicated by a thick solid line, the option member 604 and the elements fixed thereto are indicated by a thin solid line, and the coil elements are indicated by a dotted line, an alternate long and short dash line, or an alternate long and two short dash line.

In the following, structure of each part of the RF coil device 90M will be described with reference to FIGS. 55 to 58.

As shown in FIG. 55, the cover member 600 has a shape obtained by bending a flat plate in such a manner that "its ambilateral surfaces" and "its transverse section in parallel with these ambilateral sides" are both angled-bracket-shaped. The cover member 600 is made of a non-deformable material such as FRP.

The cable 98 is provided on the top surface of the cover member 600.

As shown in FIGS. 55 and 56, the ring member 608 is fixed to the inner surface of the cover member 600 by a connector 610. The ring member 608 is made of a non-deformable material such as FRP, has an annular shape so that the arm of the object can pass through the aperture (opening) of the ring member 608, and serves as a supporting member.

The flap members 620, 622, 624 and 626 are fixed to the anterior surface (the surface that is opposite to the surface to which the ring member 608 is fixed and is indicated by the thick solid line in FIG. 56) of the cover member 600.

The flap members 620, 622, 624 and 626 are made of a flexible material such as FPC, have a rounded rectangular flap-like shape and substantially the same size, and are fixed to the cover member 600 at one end side.

The cover member 600 is generally symmetric with respect to the normal to the aperture of the ring member 608.

Specifically, the flap members 620 and 626 are attached to the cover member 600 at positions closer to the coupling surface (one of the angled-bracket-shaped surface thereof), at which the cover member 600 is connected to the option member 604, so as to face each other with the ring member 608 interposed therebetween.

The flap members 622 and 624 are attached to the cover member 600 at positions closer to the opposite angled-bracket-shaped surface so as to face each other.

For decoupling of the coil element provided therein (see FIG. 58 described later), the flap member 622 is partially overlaid on the flap member 626. Similarly, the flap member 624 is partially overlaid on the flap member 626.

As shown in FIG. 55 and FIG. 56, connectors 640a, 642a and 644a for achieving interdigitation with the option member 604 are disposed on the coupling surface of the cover member 600.

As shown in FIGS. 55 and 57, the coupling surface of the option member 604, at which the option member 604 is connected (interdigitated) to the cover member 600, has the same size and shape as the angled-bracket-shaped surface of the cover member 600 (except for the difference in shape between the male-type connectors and the female-type connectors). The surface of the option member 604 opposite to the coupling surface is semi-spherical with the recess facing downward.

Connectors 640b, 642b and 644b respectively shaped to interdigitate with the connectors 640a, 642a and 644a are disposed on the coupling surface of the option member 604 at positions corresponding to the connectors 640a, 642a and 644a, respectively.

As indicated by the three arrows pointing in the same direction in FIG. 55, the option member 604 is fixed to the surface of the cover member 600 by the connectors 640a and 640b interdigitating with each other, the connectors 642a and 642b interdigitating with each other, and the connectors 644a and 644b interdigitating with each other. The option member 604 is made of a non-deformable material such as FRP.

As shown in FIG. 55, a flap member 630 is disposed on the surface opposite to the coupling surface of the option member 604. Flap members 628 and 632 are disposed on the ambilateral sides of the flap member 630 so as to face each other.

The flap members 628, 630 and 632 are made of a flexible material such as FPC, have a rounded rectangular shape and are fixed to the option member 604 at one end. The direction of extension of the flap members 628 and 632 on the side of the option member 604 is aligned with the direction of extension of the flap members 620, 622, 624 and 626 on the side of the cover member 600.

The flap member 632 is disposed to extend beyond the coupling surface of the option member 604 in such a manner that the flap member 632 is partially overlaid on the flap member 620 when the cover member 600 is connected to the option member 604 (see FIG. 55). This is intended to obtain a decoupling effect.

Similarly, the flap member 628 is disposed to extend beyond the coupling surface of the option member 604 in such a manner that the flap member 628 is partially overlaid on the flap member 626 when the cover member 600 is connected to the option member 604.

In the following, an arrangement of the coil elements in the RF coil device 90M will be described with reference to FIG. 58.

As shown by a dotted line in the drawing, the loop-shaped coil element 648 is provided to make a circuit in the annular interior of the ring member 608.

Loop-shaped (elliptic) coil elements 650, 652, 654, 656, 658, 660 and 662 are disposed in the flap members 620, 622, 624, 626, 628, 630 and 632. For the sake of discrimination, the coil element 650 in the flap member 620 and the coil element 656 in the flap member 626 are shown by an alternate long and short dash line, and the other five coil elements 652, 654, 658, 660 and 662 are shown by a dashed line.

As shown in FIG. 58, in the state where the cover member 600 and the option member 604 are connected to each other, the coil element 650 is disposed to overlap on the coil element 662 in a part closer to the option member 604 in a plan view. This is intended to obtain a decoupling effect. The coil element 650 is also disposed to overlap on the coil element 652 in a part opposite to the option member 604 in a plan view.

Similarly, the coil element 656 is disposed to overlap on the coil element 658 in a part closer to the option member 604 in a plan view, and is disposed to overlap on the coil element 654 in a part opposite to the option member 604 in a plan view.

The coil element 648 in the ring member 608 is electrically connected to a separate wire in the cable 98 by electrodes or the like in the connector 610 and a circuit or the like in the cover member 600.

The coil element 658 in the flap member 628 is electrically connected to a separate wire in the cable 98 by a circuit in the option member 604, electrodes or the like in the connectors 644*a* and 644*b* (see FIG. 55) and a circuit or the like in the cover member 600.

The coil element 660 in the flap member 630 is electrically connected to a separate wire in the cable 98 by the circuit in the option member 604, electrodes or the like in the connectors 642*a* and 642*b* and the circuit in the cover member 600.

The coil element 662 in the flap member 632 is electrically connected to a separate wire in the cable 98 by the circuit in the option member 604, electrodes or the like in the connectors 640*a* and 640*b* and the circuit in the cover member 600.

Note that illustration of the circuit in the option member 604, the electrodes in the connectors and the circuit in the cover member 600 is omitted for the sake of simplicity.

The coil elements 650, 652, 654 and 656 are also electrically connected to a separate wire in the cable 98 by the circuit or the like in the cover member 600, respectively.

Figure 59:
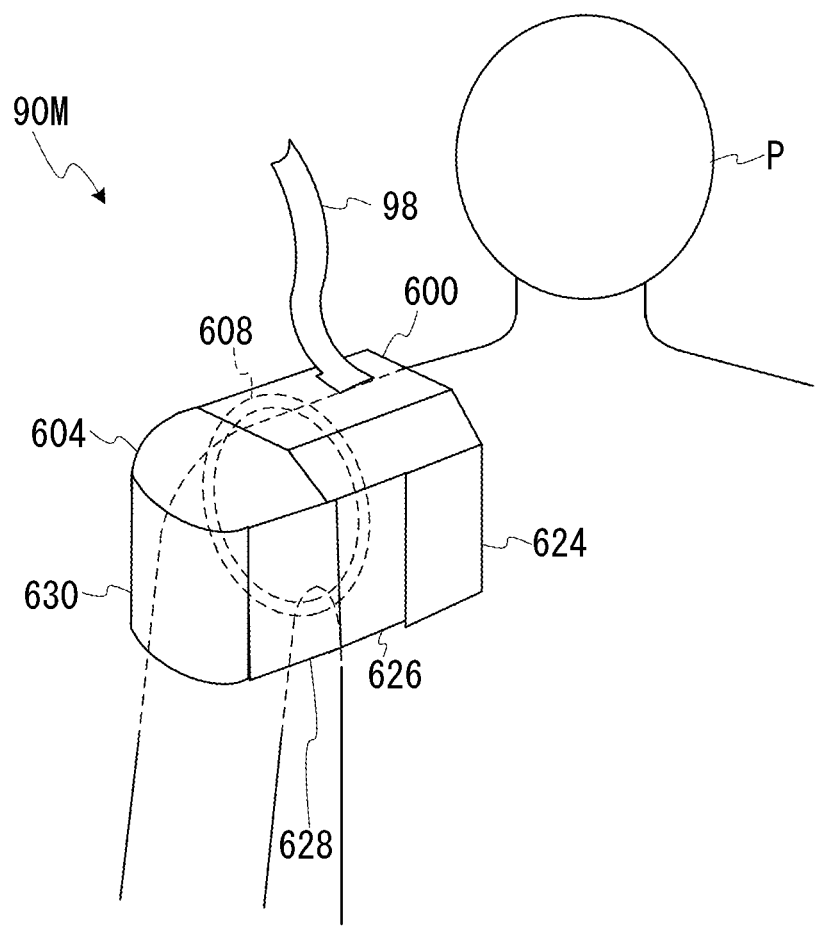
FIG. 59 is a schematic oblique drawing showing an example of the mounting state of the RF coil device of the tenth embodiment on an object with the arm lowered, in such a manner that the cover member and the option member are connected to each other.

FIG. 59 is a schematic oblique drawing showing an example of the mounting state of the RF coil device 90M on the object P with the arm lowered, in such a manner that the cover member 600 and the option member 604 connected to each other.

For example, the RF coil device 90M can be mounted by putting the arm of the object P into the ring member 608, placing the cover member 600 over the anterior surface and the posterior surface of the shoulder of the object P, and then coupling the option member 604 to the cover member 600.

Figure 60:
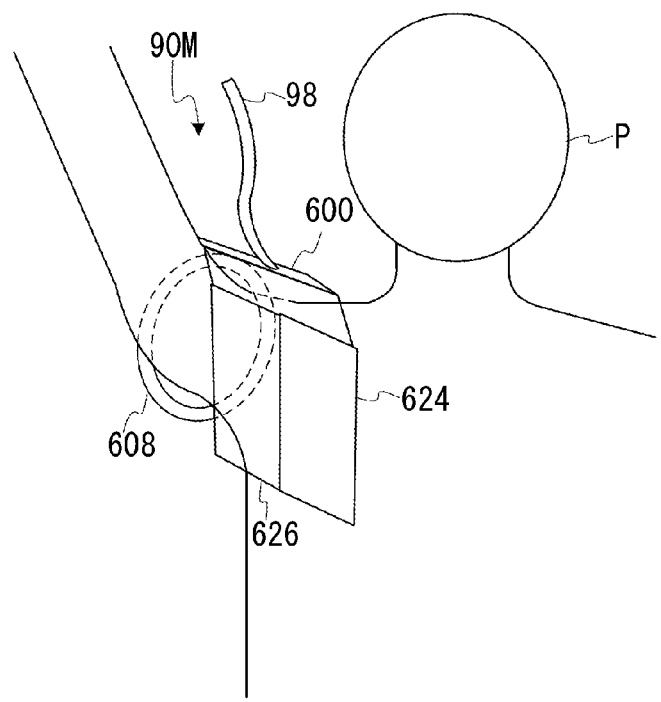
FIG. 60 is a schematic oblique drawing showing an example of the mounting state of the RF coil device of the tenth embodiment, under the state in which the option member is removed and the arm of the object is raised from the position shown in FIG. 59.

FIG. 60 is a schematic oblique drawing showing an example of the mounting state of the RF coil device 90M, under the state in which the option member 604 is removed and the arm of the object P is raised from the position shown in FIG. 59.

In the mounting states of the RF coil device 90M, the coil elements 654 and 656 ensure satisfactory coil sensitivity regions on the anterior side of the shoulder, the coil elements 650 and 652 ensure satisfactory coil sensitivity regions on the posterior side of the shoulder, and the coil elements 658, 660 and 662 ensure satisfactory coil sensitivity regions around the root (base) of the arm of the object P. In addition, the sensitivity region of the coil element 648 extends around the arm in the direction perpendicular to the sensitivity regions of the coil elements 650, 652, 654 and 656. This arrangement ensures a satisfactory coil sensitivity region during imaging with the arm lowered.

Note that the option member 604 is an auxiliary member intended to increase the coil sensitivity region during imaging with the arm lowered and thus is not essential. Whether the arm is raised or lowered, the five coil elements 648, 650, 652, 654 and 656 of the cover member 600 ensure a satisfactory coil sensitivity region by themselves.

The ring member 608 is fixed to the inner surface of the cover member 600 at a position closer to the coupling surface (see FIGS. 55 and 58). Therefore, in the mounting state, the cover member 600 hardly extends beyond the apex of the shoulder of the object P. In other words, the cover member 600 hardly interferes with raising of the arm of the object P. In addition, the flap members 620, 622, 624 and 626 of the cover member 600 do not interfere with any movement of the arm of the object P, since the flap members are flexible.

As described above, the option member 604 is only an auxiliary member. Therefore, whether the arm is raised or lowered, the RF coil device 90M can be easily mounted depending on the mounting state of the cover member 600 alone. Even if the option member 604 is connected to the cover member 600, simply removing the option member 604 allows the object P to raise and lower the arm.

In this way, in the tenth embodiment, the same advantages as those in the third embodiment can be provided.

Figure 61:
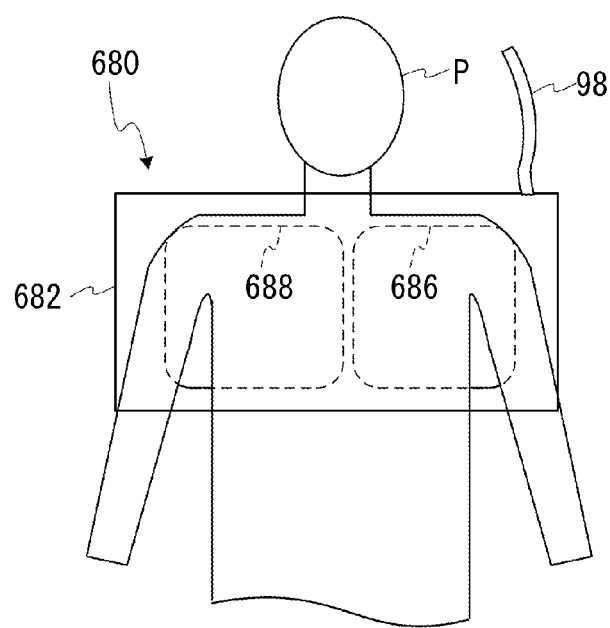
FIG. 61 is a schematic planimetric diagram of an RF coil device for a human back, which is used in combination with the RF coil device of the tenth embodiment in order to widen the sensitivity region on the posterior side of an object.

In the case where the RF coil device 90M according to the tenth embodiment is used, an RF coil device 680 shown in the schematic planimetric diagram of FIG. 61 can be used in combination in order to widen the coil sensitivity region on the posterior side of the object P.

The RF coil device 680 has a base board 682 and loop-shaped coil elements 686 and 688 disposed in the base board 682 and each connected to a separate wire in the cable 98 by a circuit (not shown). The two coil elements 686 and 688 are sized to cover the upper half of the back of the object P in cooperation, for example.

Although the cover member 600 is angled-bracket-shaped according to the tenth embodiment described above, this is only an example. As an alternative, the cover member 600 may be U-shaped, like a bent flat plate, for example. In this case, the coupling surface of the option member 604 preferably has the same shape and dimensions as the coupling surface of the cover member 600.

Figure 62:
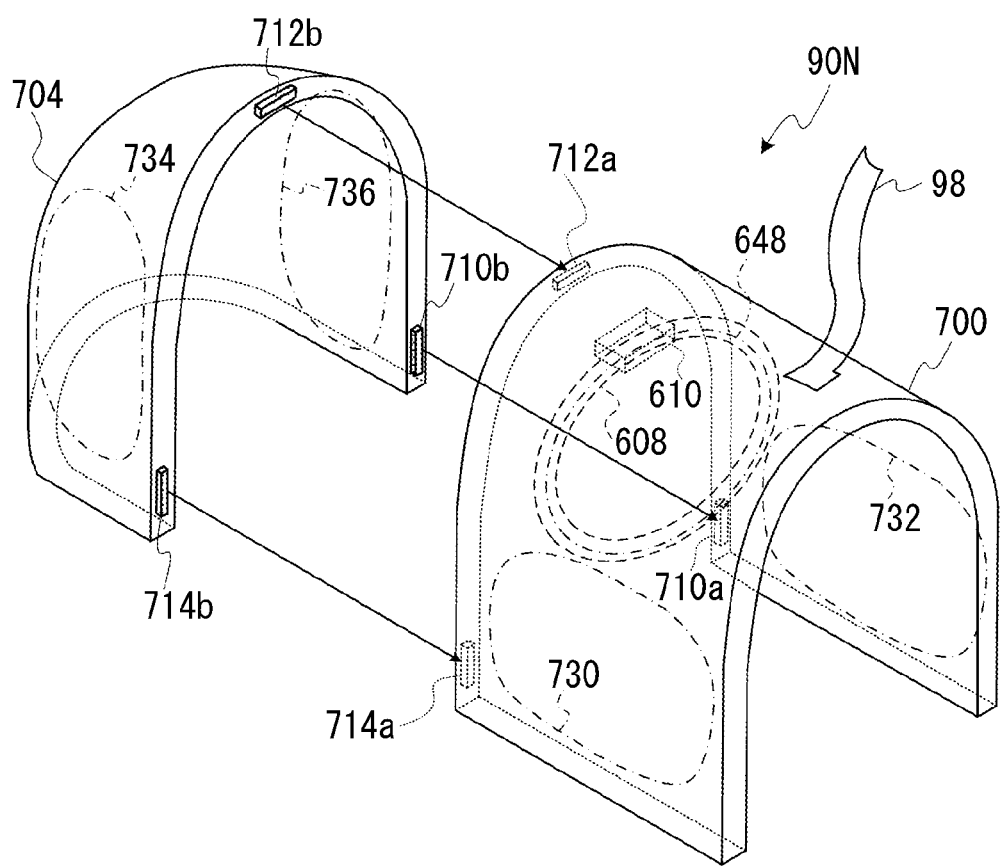
FIG. 62 is a schematic exploded perspective view showing a schematic configuration of an RF coil device according to a modification of the tenth embodiment.

FIG. 62 is a schematic exploded perspective view showing a schematic configuration of an RF coil device 90N according to a modification of the tenth embodiment in which the flap members are omitted. As shown in FIG. 62, the RF coil device 90N has a cover member 700 and an option member 704 connected to the cover member 700. The three solid line arrows in FIG. 62 are identical to each other, and indicate the directions of coupling between connectors on the cover member 700 and connectors on the option member 704.

The cover member 700 has a shape obtained by bending a flat plate so as to become U-shaped in its ambilateral surfaces and transverse section. The cover member 700 is made of a non-deformable material such as FRP. The cable 98 is disposed on the top surface of the cover member 700.

The ring member 608 described above is fixed to the inner surface of the cover member 700 by the connector 610. Connectors 710*a*, 712*a* and 714*a* for achieving interdigitation with the option member 704 are disposed on the coupling surface of the cover member 700, at which the cover member 700 is connected to the option member 704.

The coupling surface of the option member 704, at which the option member 704 is connected to the cover member 700, has the same size and shape as the U-shaped coupling surface of the cover member 700 (except for the difference between the male-type connectors and the female-type connectors). As with the option member 604 of the RF coil device 90M, the option member 704 is made of a non-deformable material such as FRP and has a recessed shape.

Connectors 710*b*, 712*b* and 714*b* shaped to interdigitate with the connectors 710*a*, 712*a* and 714*a* are disposed on the coupling surface of the option member 704 at positions corresponding to the connectors 710*a*, 712*a* and 714*a*, respectively. The option member 704 is fixed to the coupling surface of the cover member 700 by the connectors 710*a* and 710*b* interdigitating with each other, the connectors 712*a* and 712*b* interdigitating with each other, and the connectors 714*a* and 714*b* interdigitating with each other.

Additionally, as shown by alternate long and short dash lines in FIG. 62, in the cover member 700, a loop-shaped coil element 730 is disposed at a position close to the connector 714*a*, and a loop-shaped coil element 732 is disposed at a position close to the connector 710*a*. Similarly, in the option member 704, loop-shaped coil elements 734 and 736 are disposed at positions to face each other.

Figure 63:
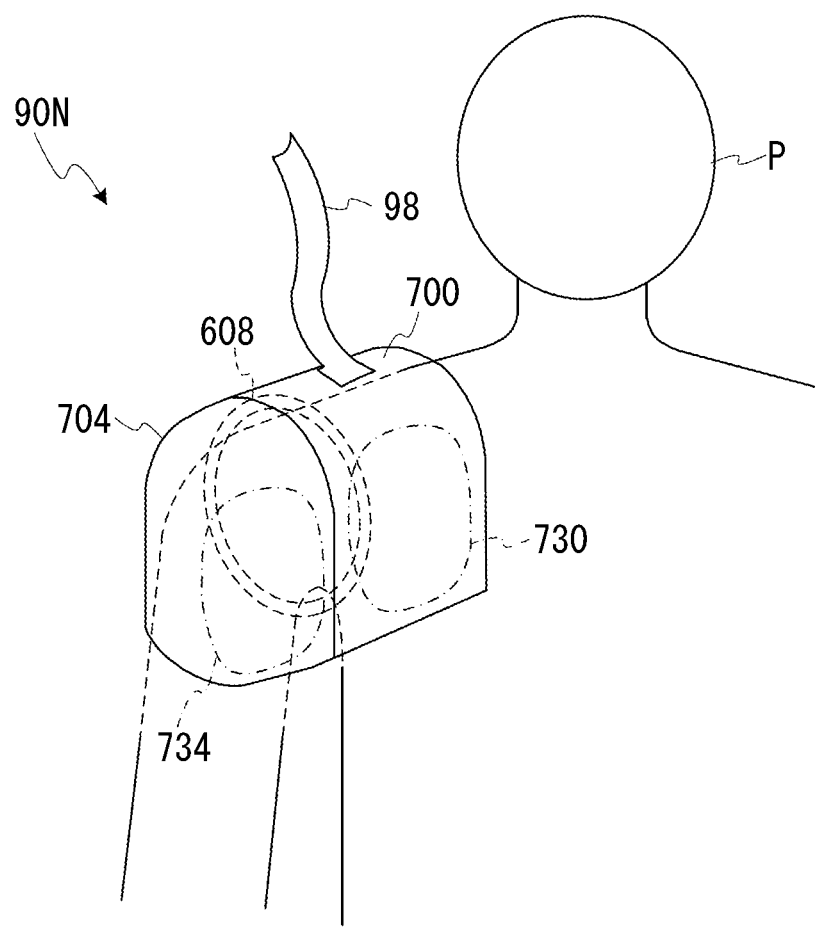
FIG. 63 is a schematic oblique drawing showing an example of the mounting state of the RF coil device of the modification of the tenth embodiment on an object with the arm lowered, in such a manner that its cover member and option member are connected to each other.

FIG. 63 is a schematic oblique drawing showing an example of the mounting state of the RF coil device 90N with the cover member 700 and the option member 704 connected to each other on the object P with the arm lowered. The RF coil device 90N described above can be mounted in the same way as the RF coil device 90M.

Figure 64:
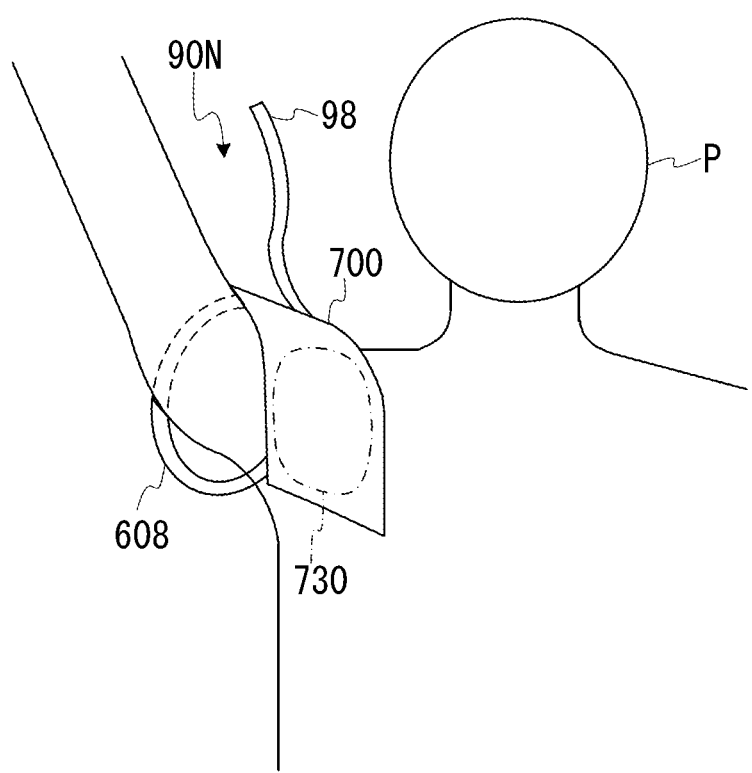
FIG. 64 is a schematic oblique drawing showing an example of the mounting state of the RF coil device of the modification of the tenth embodiment, under the state in which the option member is removed and the arm of the object is raised from the position shown in FIG. 63.

FIG. 64 is a schematic oblique drawing showing an example of the mounting state of the RF coil device 90N in which the option member 704 is removed and the arm of the object P is raised from the position shown in FIG. 63.

In the mounting states of the RF coil device 90N, the coil elements 730 and 734 ensure satisfactory coil sensitivity regions on the anterior side of the shoulder, and the coil elements 732 and 736 ensure satisfactory coil sensitivity regions on the posterior side of the shoulder.

In addition, the sensitivity region of the coil element 648 extends around the arm in the direction perpendicular to the sensitivity regions of the coil elements 730 and 732. This arrangement ensures a satisfactory coil sensitivity region during imaging with the arm lowered.

As in the case of the RF coil device 90M, the option member 704 is an auxiliary member and thus is not essential. Whether the arm is raised or lowered, the three coil elements 648, 730 and 732 of the cover member 700 can ensure a satisfactory coil sensitivity region by themselves.

With the RF coil device 90N also, since the ring member 608 is fixed to the inner surface of the cover member 700 at a position closer to the coupling surface (see FIG. 62), the cover member 700 hardly extends beyond the apex of the shoulder of the object P in the mounting state. Therefore, as with the RF coil device 90M, the RF coil device 90N can be mounted whether the arm is raised or lowered, and the same advantages as those of the third embodiment can be provided.

The Eleventh Embodiment

Figure 65:
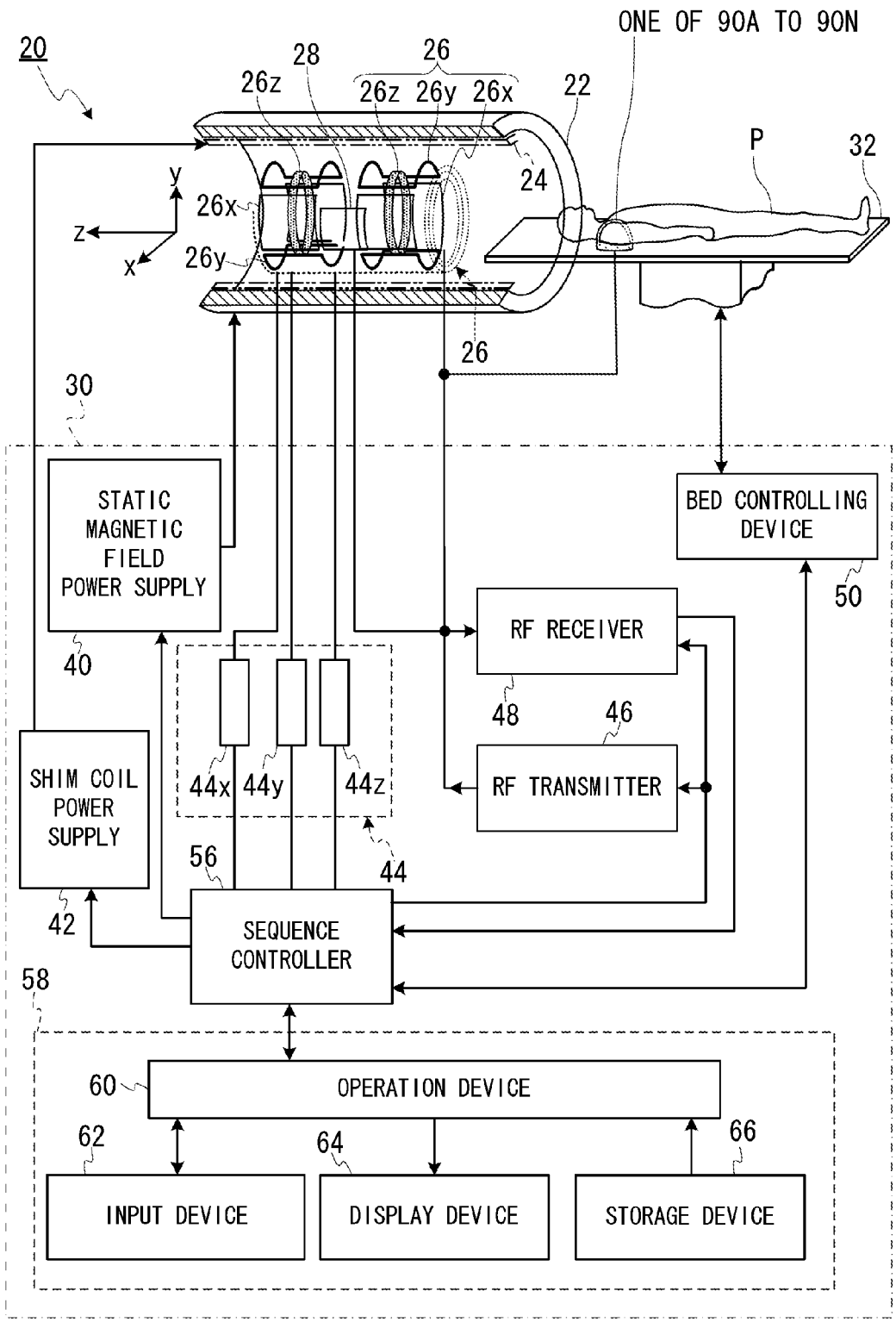
FIG. 65 is a block diagram showing general structure of the MRI apparatus of the eleventh embodiment.

FIG. 65 is a block diagram showing general structure of the MRI apparatus 20 according to the eleventh embodiment. As shown in FIG. 65, the MRI apparatus 20 includes a cylinder-shaped static magnetic field magnet 22 for generating a static magnetic field, a cylinder-shaped shim coil 24 coaxially-arranged inside the static magnetic field magnet 22, a gradient coil 26 (gradient magnetic field coil 26), RF coils 28, a control system 30, and a bed 32 for placing an object P on it. Moreover, the MRI apparatus 20 includes the RF coil devices 90A to 90N, and one of them is used in imaging.

Here, as one example, an apparatus coordinate system, whose X axis, a Y axis and a Z axis are perpendicular to each other, is defined as follows.

Firstly, the direction of an axis of the static magnetic field magnet 22 and the shim coil 24 is aligned with the direction which is perpendicular to the vertical direction, and the direction of the axis of the static magnetic field magnet 22 and the shim coil 24 is defined as the Z axis direction.

Additionally, it is assumed that the vertical direction is the same as the Y axis direction. Moreover, the bed 32 is disposed in such a position that the direction of the normal line of the table plane thereof on which an object is put is the same as the Y axis direction.

The control system 30 includes a static magnetic field power supply 40, a shim coil power supply 42, a gradient magnetic field power supply 44, an RF transmitter 46, an RF receiver 48, a bed controlling device 50, a sequence controller 56 and a computer 58.

The gradient magnetic field power supply 44 includes an X-axis gradient magnetic field power supply 44x, a Y-axis gradient magnetic field power supply 44y and a Z-axis gradient magnetic field power supply 44z.

Additionally, the computer 58 includes an operation device 60, an input device 62, a display device 64 and a storage device 66.

The static magnetic field magnet 22 is electrically connected to the static magnetic field power supply 40 and generates a static magnetic field in an imaging space by using electric current supplied from the static magnetic field power supply 40.

The aforementioned "imaging space" means, for example, a space in a gantry in which an object P is placed and to which a static magnetic field is applied. The term "gantry" refers to a structure having a cylindrical shape, for example, which includes the static magnetic field magnet 22, the shim coil 24, the gradient magnetic field coil 26, and the RF coils 28. For simplicity, FIG. 65 does not show the gantry itself, but shows the components of the gantry such as the static magnetic field magnet 22.

The "imaging region" means, for example, a region set as a part of the imaging space and is a range of acquisition of MR signals used to generate one image or one set of images.

The shim coil 24 is electrically connected to the shim coil power supply 42 and uniforms the static magnetic field with the electric current supplied from the shim coil power supply 42.

The static magnetic field magnet 22 includes a superconductivity coil in many cases. The static magnetic field magnet 22 gets electric current from the static magnetic field power supply 40 at excitation. However, once excitation has been made, the static magnetic field magnet 22 is usually isolated from the static magnetic field power supply 40. The static magnetic field magnet 22 may include a permanent magnet which makes the static magnetic field power supply 40 unnecessary.

The gradient coil 26 includes an X-axis gradient coil 26x, a Y-axis gradient coil 26y and a Z-axis gradient coil 26z. Each of the X-axis gradient coil 26x, the Y-axis gradient coil 26y and the Z-axis gradient coil 26z is cylinder-shaped and arranged inside the static magnetic field magnet 22.

The X-axis gradient coil 26x, the Y-axis gradient coil 26y and the Z-axis gradient coil 26z are electrically connected to the X-axis gradient magnetic field power supply 44x, the Y-axis gradient magnetic field power supply 44y and the Z-axis gradient magnetic field power supply 44z, respectively.

The X-axis gradient magnetic field power supply 44x, the Y-axis gradient magnetic field power supply 44y and the Z-axis gradient magnetic field power supply 44z supply electric current to the X-axis gradient coil 26x, the Y-axis gradient coil 26y and the Z-axis gradient coil 26z respectively so as to generate a gradient magnetic field Gx in the X-axis direction, a gradient magnetic field Gy in the Y-axis direction and a gradient magnetic field Gz in the Z-axis direction in the imaging region.

That is, directions of a gradient magnetic field Gss in a slice selection direction, a gradient magnetic field Gpe in a phase encoding direction and a gradient magnetic field Gro in a readout (frequency encoding) direction can be arbitrarily set as logical axises, by combining the gradient magnetic fields Gx, Gy and Gz in the X-axis, Y-axis and Z-axis directions as three physical axises of the apparatus coordinate system.

The gradient magnetic fields Gss, Gpe and Gro in the slice selection direction, the phase encoding direction and the readout direction are superimposed on the static magnetic field.

The RF transmitter 46 generates RF signals (RF current pulses) in accordance with control information provided from the sequence controller 56, and outputs the generated RF signals to the transmission RF coil 28.

The RF coils 28 include a whole body coil (not shown in figure) built in the gantry for transmission and reception of RF signals and local coils arranged around the bed 32 or the object P for reception of RF pulses.

In this embodiment, as an example of the local coils, one of the RF coil devices 90A to 90N is connected to the RE receiver 48.

The transmission RF coil 28 transmits an RF signal given from the RF transmitter 46 to the object P.

The reception RF coil 28, which includes one of the RF coil devices 90A to 90N, receives an MR signal (an echo signal as a nuclear magnetic resonance signal) generated due to excited nuclear spin inside the object P by the RF signal and this MR signal is detected by the RF receiver 48.

The RF receiver 48 generates raw data which are digitized complex number data obtained by performing A/D (analogue to digital) conversion after performing various types of signal processing such as preamplification, intermediate-frequency conversion, phase detection, low-frequency amplification and filtering to the detected MR signal. The RF receiver 48 inputs the generated raw data to the sequence controller 56. Although the RF receiver 48 is arranged outside the aforementioned gantry, the RF receiver 48 may be arranged inside the gantry.

The operation device 60 performs system control of the entirety of the MRI apparatus 20.

The sequence controller 56 storages control information needed in order to make the gradient magnetic field power supply 44, the RF transmitter 46 and the RF receiver 48 drive. The aforementioned control information includes, for example, sequence information describing operation control information such as intensity, impression period and impression timing of the pulse electric current which should be impressed to the gradient magnetic field power supply 44.

The sequence controller 56 generates the gradient magnetic fields Gx, Gy and Gz in the X-axis, Y-axis and Z-axis directions and RF signals (RF pulses) by driving the gradient magnetic field power supply 44, the RF transmitter 46 and the RF receiver according to a predetermined sequence stored. Additionally, the sequence controller 56 receives raw data of an MR signal inputted from the RF receiver 48, and input the raw data to the operation device 60.

Hereinafter, a flow of operation of imaging which includes a shoulder as the imaging region and is performed by the aforementioned MRI apparatus 20 will be described.

One of the RF coil devices 90A to 90N is set (mounted) on the shoulder of an object, the object P is set on the bed 32, and a static magnetic field is formed in the imaging space by the static magnetic field magnet 22 excited by the static magnetic field power supply 40. In addition, electric current is supplied from the shim coil power supply 42 to the shim coil 24, thereby the static magnetic field formed in the imaging space is uniformed.

Then, when the operation device 60 receives a command of start of imaging from the input device 62, the operation device 60 inputs imaging conditions including a pulse sequence into the sequence controller 56. Then, the sequence controller 56 drives the gradient magnetic field power supply 44, the RF transmitter 46 and the RF receiver 48 according to the inputted pulse sequence, thereby a gradient magnetic field is formed in the imaging region and RF signals are generated from the RF coil 28.

Therefore, MR signals generated by nuclear magnetic resonance inside the object P are received by the RF coil 28 (including one of the RF coil devices 90A to 90N) and detected by the RF receiver 48. The RF receiver 48 performs predetermined signal processing on the detected MR signals and then performs A/D conversion on the MR signals to generate raw data, which are digital data of the MR signals. The RF receiver 48 inputs the generated raw data to the sequence controller 56.

The sequence controller 56 inputs the raw data to the operation device 60. The operation device 60 arranges the raw data in the k-space formed inside it as k-space data.

The operation device 60 reconstructs image data by performing image reconstruction processing including Fourier transformation on the k-space data, stores the reconstructed image data, generates image data for display by performing predetermined image processing on the reconstructed image data, and stores the image data for display in the storage device 66.

As just described, because one of the RF coil devices 90A to 90N is used for shoulder imaging in this embodiment, one RF coil device (one of the RF coil devices 90A to 90N) can meet both of the shoulder imaging under the pose in which the arm raised and lowered.

Because one of the RF coil devices 90A to 90N is used, sensitivity of coil elements can be sufficiently kept in wide dimension in shoulder imaging. That is, similar effects in the first to tenth embodiments can be obtained.

Supplementary Notes on Embodiments

[1] In the aforementioned embodiments, functions, effects and the like in the case of applying the RF coil devices 90A to 90N to a shoulder of an object. However, embodiments of the present invention are not limited to such an aspect. The RF coil devices 90A to 90N can be applied to other parts of an object such as an ankle, for example, for reception or transmission of RF signals.

[2] In the first embodiment, there has been described an example in which the belt members 94a, 94b, 94c, 94d, and 94d' are semicircularly curved. However, this is only an example. For example, the belt members may be folded to become angled-bracket-shaped. This point applies to the second to the fourth embodiments and the sixth embodiment. The aforementioned "curve" means that a transverse section of the curved part is shaped like a curved line. The aforementioned "folded" means a state in which a transverse section of the folded part can be separated into a straight line and another straight line.

[3] Examples in which the belt members 94a, 94b, 94c, 94d, 94d', 242, 286a, 344, 346, 404, and 502 are in the form of bands (their transverse sections are rectangular) have been explained. However, embodiments of the present invention are not limited to such an aspect. For example, the belt member may be shaped so that its transverse section is circular or elliptical (ropelike).

[4] In the first embodiment, the connectors 100 and 102 are shown as an example of "the connecting unit" which electrically connects the partial coil 108b inside the belt member 94a with the partial coil 108a inside the base member 92 in order for them to function as one loop coil element. This is only an example of "the connecting unit".

Figure 66:
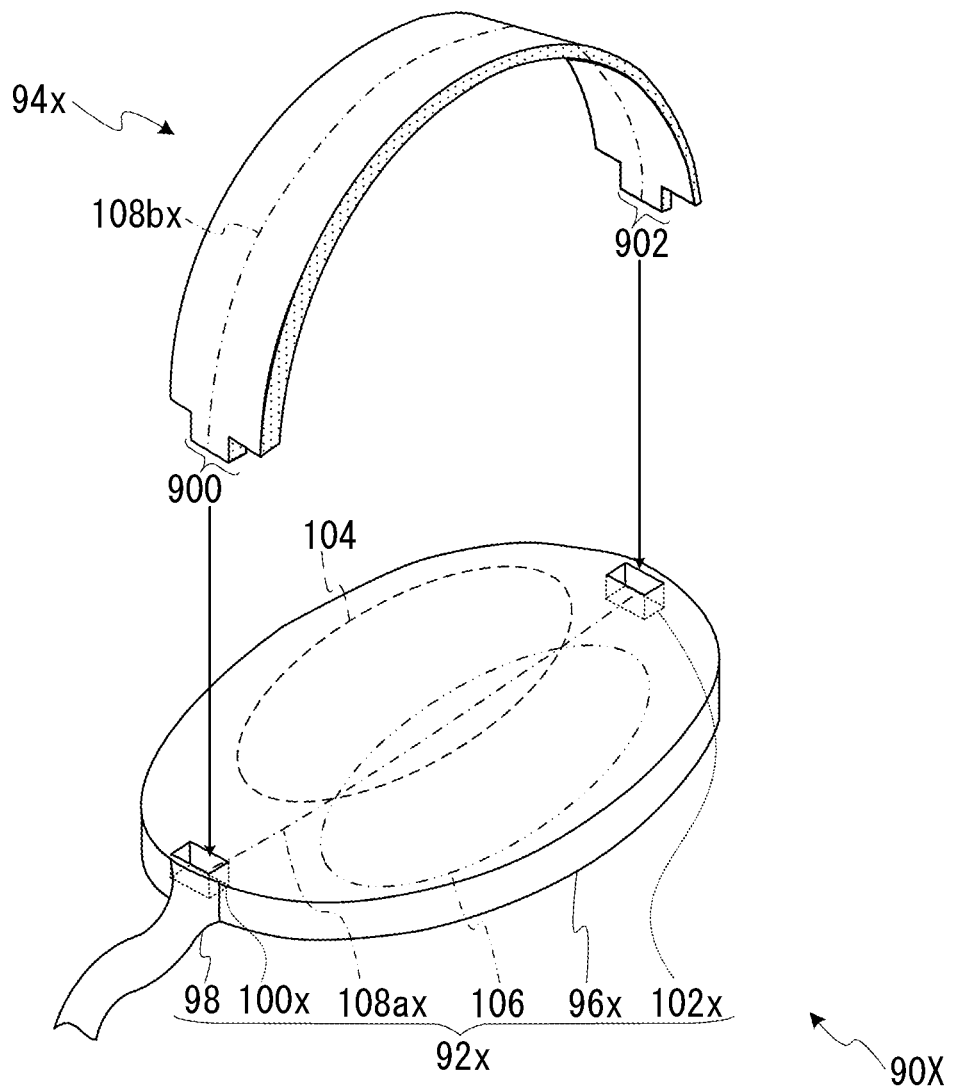
FIG. 66 is an exploded perspective view showing the outline structure of the supplementary embodiment of the first embodiment.

As shown in FIG. 66, the first and second partial coils may be electrically connected to each other with two dents, which are formed in the base board and respectively shaped to interdigitate one end and the opposite end of the belt member. This point applies to the connectors in the second to the sixth embodiments, and details will be explained below.

FIG. 66 is an exploded perspective view showing outline structure of an RF coil device 90x as the supplementary embodiment of the first embodiment. The structure of the RF coil device 90x is similar to that of the RF coil device 90A of the first embodiment shown in FIG. 1 to FIG. 3 except "the connecting unit". Therefore, it will be explained focusing on the difference.

The side of one end of the belt member 94x is composed as a convex part 900, and the opposite end of the belt member 94x is composed as a convex part 902. A partial coil 108bx is disposed from the tail end of the convex part 900 to the tail end of the convex part 902 inside the belt member 94x.

The base member 92x includes a disk-shaped base board 96x and the cable 98. Coil elements 104, 106, and a partial coil 108ax are disposed inside the base board 96x. Moreover, rectangular parallelopiped holes are respectively formed in the sides of one end and the opposite end of the anterior surface (the frontal surface) of the base board 96x. These holes function as concave connecting units 100x and 102x.

The concave connecting units 100x and 102x are shaped so that they respectively interdigitate the convex parts 900 and 902.

Inside the concave connecting units 100x and 102x, the partial coil 108ax extends up to the exposure position of the partial coil 108bx (each end of the convex part 900 and 902) in the interdigitation state between the belt member 94x and the base board 96x, and the partial coil 108ax is exposed at the exposure position.

Thus, by interdigitating the convex part 900 and 902 as both ends of the belt member 94x to the concave connecting units 100x and 102x respectively, both ends of the partial coil 108ax and both ends of the partial coil 108bx are mutually electrically connected to each other, and they function as a loop coil element.

The similar effects in the first embodiment can be obtained in the aforementioned RF coil device 90X as the supplementary embodiment. Additionally, the RF coil device 90x may be added to one of the components of the MRI apparatus in the eleventh embodiment, and similar effects can be obtained in this case.

[5] Correspondences between terms used in the claims and terms used in the embodiment described above will be described. Note that the correspondences described below are just some of possible interpretations for reference and should not be construed as limiting the present invention.

The functions of the entire structure including the static magnetic field magnet 22, the shim coil 24, the gradient coil 26, the RF coils 28 and the control device 30 (see FIG. 65) that receive MR signals from the object P under imaging with application of a static magnetic field and gradient magnetic fields and transmission of RF signals are an example of a signal acquisition unit described in the claims.

The function of the operation device 60 that reconstructs image data of the object P based on the acquired MR signals (nuclear magnetic resonance signals, i.e. echo signals) is an example of an image generation unit described in the claim.

[6] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An RF coil device which is configured to be set on a shoulder of an object and to receive an echo signal in magnetic resonance imaging, said RF coil device comprising:
   a base board that has a thickness between an anterior surface and an underside surface opposite to the anterior surface, and is to come into contact with the object at the anterior surface;
   a belt member that has a band-like shape with two ends, is connected at each end to the base board at different positions spaced apart from each other with a central part of the belt member being located on a side of the anterior surface of the base board, and is bent to form a space for disposing an arm of the object between the central part and the anterior surface when the base board and the belt member are connected to each other;
   a first coil element that includes a first partial coil disposed in the belt member and a second partial coil disposed in the base board and forms a loop coil when the first partial coil and the second partial coil are electrically connected to each other;
   a second coil element disposed in the base board; and
   a plurality of connecting units that are disposed on the anterior surface of the base board at one end and another end of the second partial coil, detachably connects the base board and the belt member to each other, and electrically connects the first partial coil and the second partial coil to each other when the base board and the belt member are connected to each other.

2. The RF coil device according to claim 1, wherein the base board is configured in a form of a flat plate.

3. The RF coil device according to claim 2, wherein the first and second coil elements are arranged in such a manner that each extending region of each wire of the first and second coil elements is planar and a plane overlapping an entire loop of the first coil element is perpendicular to a plane overlapping an entire loop of the second coil element, when the belt member and the base board are connected to each other.

4. An RF coil device which is configured to be set on a shoulder of an object and to receive an echo signal in magnetic resonance imaging, said RF coil device comprising:
   a base board that has a thickness between an anterior surface and an underside surface opposite to the anterior surface, and is to come into contact with the object at the anterior surface;
   a belt member that has a band-like shape with two ends, is connected at each end to the base board at different positions spaced apart from each other with a central part of the belt member being located on a side of the anterior surface of the base board, and is bent to form a space for disposing an arm of the object between the central part and the anterior surface when the base board and the belt member are connected to each other;
   a first coil element that has a part disposed in the belt member to extend from one end to another end and a remaining part disposed in the base board so as to form a loop coil;

a second coil element disposed in the base board;
an overlay member that is detachably connected to the base board to partially cover the anterior surface of the base board; and
a third coil element at least a part of which is disposed in the overlay member.

5. The RF coil device according to claim 4,
wherein the overlay member is made of a flexible material.

6. The RF coil device according to claim 4,
wherein the base board is configured in a form of a flat plate.

7. The RF coil device according to claim 4,
wherein the first and second coil elements are arranged in such a manner that each extending region of each wire of the first and second coil elements is planar and a plane overlapping an entire loop of the first coil element is perpendicular to a plane overlapping an entire loop of the second coil element, when the belt member and the base board are connected to each other.

8. An RF coil device which is configured to be set on a shoulder of an object and to receive an echo signal in magnetic resonance imaging, said RF coil device comprising:
a base board that has a thickness between an anterior surface and an underside surface opposite to the anterior surface and is to come into contact with the object at the anterior surface;
a belt member that has a band-like shape, is pivotally fixed to the base board at one end, is detachably connected to the base board at another end with a central part of the belt member being located on a side of the anterior surface of the base board when the belt member is connected to the base board, and is bent to form a space for disposing an arm of the object between the central part and the anterior surface when the base board and the belt member are connected to each other;
a first coil element that has a part disposed in the belt member to extend from one end to another end and a remaining part disposed in the base board, and forms a loop coil when the base board and the belt member are connected to each other;
a connecting unit that is disposed on the base board at one end of the first coil element, detachably connects another end of the belt member to the base board, and electrically connects the part and the remaining part of the first coil element to each other when the belt member and the base board are connected to each other; and
a second coil element disposed in the base board.

9. The RF coil device according to claim 8,
wherein the base board is configured in a form of a flat plate.

10. The RF coil device according to claim 9,
wherein the first and second coil elements are arranged in such a manner that each extending region of each wire of the first and second coil elements is planar and a plane overlapping an entire loop of the first coil element is perpendicular to a plane overlapping an entire loop of the second coil element, when the belt member and the base board are connected to each other.

11. An RF coil device which is configured to be set on a shoulder of an object and to receive an echo signal in magnetic resonance imaging, said RF coil device comprising:
a base member that has a first coil element disposed therein and is to come into contact with the shoulder of the object;
a belt member that is made of a flexible material in a form of a band, is partially fixed to the base member, and wraps around an arm of the object when one end and an opposite end thereof are connected to each other;
a second coil element that is disposed in the belt member to extend from said one end to said opposite end, and forms a loop coil when both ends of the belt member are connected to each other;
a connecting unit that is disposed at said one end or said opposite end of the belt member, detachably connects both ends of the belt member to each other, and electrically connects both ends of the second coil element to each other when both ends of the belt member are connected to each other;
a flap member that is made of a flexible material and is partially fixed to the belt member; and
a loop-shaped third coil element at least a part of which is disposed in the flap member.

12. An RF coil device which is configured to be set on shoulders of an object and to receive an echo signal in magnetic resonance imaging, said RF coil device comprising:
a base board that has a thickness between an anterior surface and an underside surface opposite to the anterior surface and is to come into contact with a back of the object including the shoulders at the anterior surface;
a first belt member and a second belt member each of which has a band-like shape with two ends, is connected at both ends of the respective first and second belt members to the base board at different positions with a central part thereof being located on a side of the anterior surface of the base board, and is bent to form a space for disposing a different arm of the object between the central part and the anterior surface when the first and second belt members are connected to the base board;
a first coil element that has a part disposed in the first belt member to extend from one end to another end and a remaining part disposed in the base board, so as to form a loop coil;
a second coil element that has a part disposed in the second belt member to extend from one end to another end and a remaining part disposed in the base board, so as to form a loop coil; and
a third coil element disposed in the base board.

13. The RF coil device according to claim 12,
wherein the first, second and third coil elements are arranged in such a manner that each extending region of each wire of the first, second and third coil elements is planar, when both ends of the first belt member and both ends of the second belt member are connected to the base board;
the first and third coil elements are arranged in such a manner that a plane overlapping an entire loop of the first coil element is perpendicular to a plane overlapping an entire loop of the third coil element, when both ends of the first belt member is connected to the base board; and
the second and third coil elements are arranged in such a manner that a plane overlapping an entire loop of the second coil element is perpendicular to a plane overlapping an entire loop of the third coil element, when both ends of the second belt member is connected to the base board.

14. An RF coil device which is configured to be set on a shoulder of an object and to receive an echo signal in magnetic resonance imaging, said RF coil device comprising:
   a first base member configured in a form of a flat plate;
   a second base member configured to be in a form of a flat plate, and disposed so that at least a part of the second base member overlaps on the first base member;
   a belt member configured to be circularly shaped so as to let an arm of the object pass through the belt member, and an outer periphery of the belt member being partially fixed to the first base member;
   a rotational axis structure configured to include a rotational axis passing through the first and second base members, and rotatably fix the first and second base members to the belt member;
   a first coil element disposed in the first base member;
   a second coil element disposed in the second base member; and
   a third coil element disposed in the belt member.

15. The RF coil device according to claim 14,
   wherein the first and second base members are rotatably fixed so that respective frontal surfaces of the first and second base members keep in parallel with each other; and
   the first, second and third coil elements are arranged in such a manner that each extending region of each wire of the first to third coil elements is planar, a plane overlapping an entire loop of the first coil element is perpendicular to a plane overlapping an entire loop of the third coil element, and the plane overlapping an entire loop of the first coil element is in parallel with a plane overlapping an entire loop of the second coil element.

16. An RF coil device which is configured to be set on a shoulder of an object and to receive an echo signal in magnetic resonance imaging, said RF coil device comprising:
   a band member that is made of a flexible material in a form of a band so as to wrap around an arm of the object, has a central part having a smaller width than ambilateral parts of the central part, and is tapered at one end and another end;
   a first coil element that is disposed in the band member to extend from said one end to said another end, and forms a loop coil when said one end and said another end are connected to each other;
   a connecting unit that is disposed at said one end or said another end of the band member, detachably connects said one end and said another end to each other, and electrically connects both ends of the first coil element each other when both ends of the band member are connected to each other;
   a second coil element disposed in the band member at a position closer to said one end than the central part; and
   a third coil element disposed in the band member at a position closer to said another end than the central part.

17. An RF coil device which is configured to be set on a shoulder of an object and to receive an echo signal in magnetic resonance imaging, said RF coil device comprising:
   a cover member that is made of a flexible material in a form of a band so as to cover an anterior surface and a posterior surface of the shoulder of the object with a part at one end and a part at another end by being bent at a middle part in a length direction thereof, width of a central part of the cover member being narrower than remaining parts thereof;
   a belt member that is made of a flexible material, connected at one end with one end of the cover member, and detachably connected at another end with another end of the cover member;
   a first coil element that has a part disposed in the belt member to extend from one end to another end and a remaining part disposed in the cover member to extend from one end to another end, and forms a loop coil when said another end of the cover member and another end of the belt member are connected to each other; and
   a connecting unit that is disposed at said another end of the cover member, detachably connects said another end of the cover member with said another end of the belt member each other, and electrically connects both ends of the first coil element each other when the cover member and the belt member are connected with each other;
   a second coil element disposed in the cover member at a position closer to said one end of the cover member than the central part; and
   a third coil element disposed in the cover member at a position closer to said another end of the cover member than the central part.

18. An RF coil device which is configured to be set on a shoulder of an object and to receive an echo signal in magnetic resonance imaging, said RF coil device comprising:
   a cover member that has an anterior surface and an underside surface opposite to each other, and is bent with the underside surface being positioned inside to have a U-shaped or angled-bracket-shaped transverse section in a plane perpendicular to the anterior surface and the underside surface so as to cover the shoulder of the object;
   a supporting member that has an aperture for letting an arm of the object pass and is partially fixed to the underside surface of the cover member so that an aperture plane thereof is oriented in parallel with said transverse section;
   a first flap member and a second flap member that are made of a flexible material in a form of a flap, and are partially fixed to the cover member at positions to face each other with the supporting member interposed therebetween so as to cover a part of an anterior surface or a posterior surface of the shoulder of the object;
   a first coil element disposed in the first flap member;
   a second coil element disposed in the second flap member; and
   a third coil element disposed in the supporting member so as to make a circuit on an outer side of the aperture.

19. The RF coil device according to claim 18, further comprising:
   an option member that is detachably connected to a lateral side of the cover member that is in parallel with said transverse section and has a recessed shape to cover an apex of the shoulder of the object when the cover member covers the shoulder of the object with the arm lowered;
   a third flap member that is made of a flexible material in a form of a flap, and is partially fixed to the option member to cover a part of the base of the arm of the object when the cover member and the option member cover the shoulder of the object; and a fourth coil element disposed in the third flap member.

20. A magnetic resonance imaging apparatus including a signal acquisition unit and an image generation unit, the signal acquisition unit being configured to apply a gradient magnetic field to an imaging region, transmit an RF signal for causing nuclear magnetic resonance to the imaging region, and receive an echo signal generated due to nuclear magnetic resonance as a nuclear magnetic resonance signal, the signal acquisition unit being configured to reconstruct image data of an object based on the nuclear magnetic resonance signal;

wherein the signal acquisition unit includes the RF coil device according to claim 1 which receives the echo signal.

* * * * *